(12) United States Patent
Berglund et al.

(10) Patent No.: US 10,336,725 B2
(45) Date of Patent: Jul. 2, 2019

(54) CHEMICAL COMPOUNDS

(71) Applicant: AstraZeneca AB, Sodertalje (SE)

(72) Inventors: Susanne Elisabeth Berglund, Mölndal (SE); Stephen Connolly, Macclesfield (GB); Martin Hemmerling, Mölndal (SE); Nafizal Hossain, Mölndal (SE); Anna Kristoffersson, Macclesfield (GB); Johan Rune Michael Lundkvist, Macclesfield (GB); Grigorios Nikitidis, Mölndal (SE); Lena Elisabeth Ripa, Mölndal (SE); Igor Shamovsky, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/840,339

(22) Filed: Dec. 13, 2017

(65) Prior Publication Data

US 2018/0162838 A1 Jun. 14, 2018

Related U.S. Application Data

(62) Division of application No. 15/124,393, filed as application No. PCT/GB2015/050765 on Mar. 17, 2015, now Pat. No. 9,873,678.

(60) Provisional application No. 61/954,674, filed on Mar. 18, 2014.

(51) Int. Cl.
| | |
|---|---|
| *C07D 401/12* | (2006.01) |
| *C07D 241/26* | (2006.01) |
| *A61K 31/4965* | (2006.01) |
| *A61K 45/06* | (2006.01) |
| *A61K 31/497* | (2006.01) |
| *C07D 401/06* | (2006.01) |
| *C07D 241/28* | (2006.01) |

(52) U.S. Cl.
CPC .......... *C07D 401/12* (2013.01); *A61K 31/497* (2013.01); *A61K 31/4965* (2013.01); *A61K 45/06* (2013.01); *C07D 241/26* (2013.01); *C07D 241/28* (2013.01); *C07D 401/06* (2013.01)

(58) Field of Classification Search
None
See application file for complete search history.

(56) References Cited

U.S. PATENT DOCUMENTS

| | | |
|---|---|---|
| 3,573,306 A | 3/1971 | Shepard et al. |
| 3,577,418 A | 5/1971 | Cragoe, Jr. et al. |
| 4,803,206 A | 2/1989 | Magatti et al. |
| 7,803,804 B2 | 9/2010 | Collingwood et al. |
| 7,820,678 B2 | 10/2010 | Johnson |
| 2004/0087571 A1 | 5/2004 | Brown et al. |
| 2007/0149495 A1 | 6/2007 | Bressi et al. |
| 2009/0163545 A1 | 6/2009 | Goldfarb |
| 2009/0227530 A1 | 9/2009 | Johnson |
| 2010/0130506 A1 | 5/2010 | Bhalay et al. |
| 2014/0171447 A1 | 6/2014 | Johnson |

FOREIGN PATENT DOCUMENTS

| | | |
|---|---|---|
| EP | 0057572 B1 | 7/1985 |
| EP | 0086564 B1 | 11/1985 |
| EP | 0293170 A1 | 11/1988 |
| EP | 0343865 A1 | 11/1989 |
| EP | 0343866 A1 | 11/1989 |
| WO | 1998/38167 A1 | 9/1998 |
| WO | 2001/047862 A1 | 7/2001 |
| WO | 2001/087849 A2 | 11/2001 |
| WO | 2003/040096 A2 | 5/2003 |
| WO | 2004/056775 A1 | 7/2004 |
| WO | 2006/044381 A2 | 4/2006 |
| WO | 2006/128674 A2 | 12/2006 |
| WO | 2007/071396 A2 | 6/2007 |
| WO | 2007/071400 A1 | 6/2007 |
| WO | 2008/106692 A1 | 9/2008 |
| WO | 2008/135557 A1 | 11/2008 |
| WO | 2009/074575 A2 | 6/2009 |
| WO | 2009/138378 A1 | 11/2009 |
| WO | 2009/150137 A2 | 12/2009 |
| WO | 2011/028740 A1 | 3/2011 |

(Continued)

OTHER PUBLICATIONS

Brown et al; Novel CCR1 antagonists with improved metabolic stability; BMCL; 2004, 14 (9), 2175-2179.

(Continued)

*Primary Examiner* — Ernst V Arnold
*Assistant Examiner* — Kyung S Chang

(57) ABSTRACT

The present invention provides a compound of a formula (I):

(I)

or a pharmaceutically acceptable salt thereof; a process for preparing such a compound; and to the use of such a compound in the treatment of an ENaC mediated disease state (such as asthma, CF or COPD).

3 Claims, No Drawings

Specification includes a Sequence Listing.

(56) References Cited

FOREIGN PATENT DOCUMENTS

| WO | 2011/079087 A1 | 6/2011 |
| WO | 2012/035158 A1 | 3/2012 |
| WO | 2012/064715 A1 | 5/2012 |
| WO | 2013/003386 A1 | 1/2013 |
| WO | 2013/192517 A2 | 12/2013 |
| WO | 2014/099673 A1 | 6/2014 |
| WO | 2014/099705 A1 | 6/2014 |

OTHER PUBLICATIONS

Garcia-Urdiales et al; Computational Study of the Lipase-Mediated Desymmetrisation of 2-Substituted-Propane-1,3-Diamines; ChemBioChem; 2009, 10, 2875-2883.

Hunt et al; Discovery of a novel chemotype of potent human ENaC blockers using a bioisostere approach. Part 1: quaternary amines; BMCL, 2012, 22(2), 929-932.

Hunt et al; Discovery of a novel chemotype of potent human ENaC blockers using a bioisostere approach. Part 2: [alpha]-branched quaternary amines; BMCL; 2012, 22(8), 2877-2879.

Li et al; Stereoselective Blockade of Amphibian Epithelial Sodium Channels by Amiloride Analogs; J. Pharm. Exper. Ther; 1993, 267(3), 1081-1084.

Rios-Lombardia et al; Enzymatic Desymmetrization of Prochiral 2-Substituted-1,3-Diamines: Preparation of Valuable Nitrogenated Compounds; J. Org. Chem., 2009, 74, 2571-2574.

CHEMICAL COMPOUNDS

SEQUENCE LISTING

The instant application contains a Sequence Listing which has been submitted electronically in ASCII format and is hereby incorporated by reference in its entirety. Said ASCII copy, created on Feb. 12, 2018, is named 200194-US-PCD_SL.txt and is 565 bytes in size.

The present invention concerns pyrazine derivatives having pharmaceutical activity, to processes for preparing such derivatives, to pharmaceutical compositions comprising such derivatives and to the use of such derivatives as active therapeutic agents.

Hydration of the lung airway epithelium ensures efficient ciliary function, and mucociliary clearance (MCC) is a critical first line airway innate defense mechanism. Failure of adequate mucus clearance produces mucus stasis and risk of airway obstruction and predisposes to chronic bacterial infection. Mucus hypersecretion, thickening of the mucus and reduced rates of mucociliary clearance are well established characteristics of both Cystic Fibrosis (CF) and Chronic Obstructive Lung Disease (COPD) pathophysiology, and contribute significantly to the morbidity and mortality of the diseases. Poor MCC leads to airway obstruction by static mucus, which impairs lung function and serves as a nidus for infection facilitating bacterial colonization and leading to increased rates and severity of disease exacerbations.

The pathophysiology of CF is well characterized and is caused by mutations in the cystic fibrosis transmembrane conductance regulator (CFTR) gene leading to airway dehydration, and remains one of the most common fatal hereditary disorders worldwide. Although CF is a complex multi-organ disease, morbidity and mortality are mainly determined by chronic obstructive lung disease that evolves from early onset mucus plugging in the small airways, chronic neutrophilic airway inflammation and bacterial infection.

The pathophysiology of COPD is complex and poorly understood. Current clinical guidelines describe COPD as a disease state characterized by airflow limitation that is not fully reversible. The airflow limitation is usually both progressive and associated with an abnormal inflammatory response of the lungs to noxious particles and gases. The most important contributory source of such particles and gases is tobacco smoke. COPD patients have a variety of symptoms, including cough, shortness of breath, and excessive production of sputum; such symptoms arise from dysfunctions of a number of cellular compartments, including neutrophils, macrophages, and epithelial cells.

Adequate airway hydration is of key importance for maintaining MCC and appropriate water content of mucus. The regulation of airway hydration is strongly linked to electrolyte and water movement over the epithelial cell layer. The periciliary liquid (PCL) on the airway epithelial surface surrounding the cilia separates the viscous mucus layer from the epithelial surface and facilitates ciliary beating. The volume/depth of the PCL has been shown to be a strong determinant of MCC rate.

ENaC (the Epithelial Sodium Channel) is an amiloride-sensitive, non-voltage gated ion channel widely expressed in epithelia of the respiratory, urinary, digestive, genital systems and skin. Systemically, ENaC plays a key role in electrolyte homeostasis and fluid volume balance by regulating Na$^+$ transport over the kidney epithelia. Through control of sodium transport, ENaC controls the osmotic gradient over the airway epithelium and thereby regulates the PCL volume. Blocking ENaC-mediated sodium transport reduces the osmotic gradient over the epithelium, leads to retention of water on the airway surface (increased PCL volume), and enhancement of mucus hydration and MCC rate.

A role for ENaC as a key regulator of airway surface liquid (ASL) volume and mucociliary clearance (MCC) in vivo is established in the literature. Studies on α- β- and γ-ENaC (−/−) mice, respectively, show a critical role of ENaC function in perinatal lung liquid clearance (Barker et al., J. Clin. Invest., 1998. 102(8):1634; Bonny and Hummler, Kidney Int., 2000. 57(4):1313; Pradervand et al., Proc. Natl. Acad. Sci. USA., 1999. 96(4):1732). ENaC β-subunit over-expressing transgenic mice show increased airway Na$^+$ absorption, ASL volume depletion, mucus dehydration and delayed MCC. The mice develop severe lung disease with clinical features similar to CF and COPD, including mucus obstruction, goblet cell metaplasia, neutrophilic inflammation, defective bacterial clearance and emphysema (Mall et al., Nature Med., 2004. 10:487; Mall et al., Am. J. Respir. Crit. Care Med., 2007. 177:730). The mortality rate among the transgenics during their first 20 days of life is around 50% due to extensive mucus plugging of the airways resulting in asphyxia, but mortality is significantly reduced by administration of amiloride to the lungs of the mice for 14 days after birth (Mall et al., ATS Poster abstract #G55, 2008).

Furthermore, humans with Pseudohypoaldosteronism 1 (PHA1), a disease caused by loss-of-function mutations in the genes encoding α- β- and γ-ENaC, show increased ASL volume and an upregulation of MCC (Kerem et al., N. Engl. Med., 1999. 341:156). Treatment of normal subjects with the ENaC channel blocking compound amiloride, increases ASL volume and MCC rates (Sood et al., Am. J. Crit. Care Med., 2003. 167:158).

Amiloride and benzamil are pharmaceutically active pyrazine derivatives known to blockade the epithelial sodium channel.

Briefly, this specification describes, in part, a compound of formula (I):

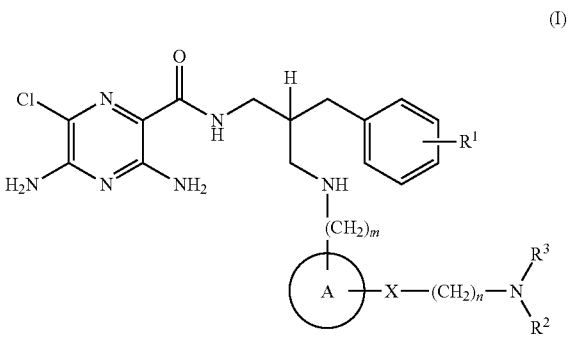

wherein:
R$^1$ is selected from hydrogen or C$_{1-4}$ alkyl;
m is 1 or 2;
A is selected from phenyl or heterocyclyl;
X is selected from —C(=O)—, —C(=O)—NR$^4$— or —O—C(=O)—NR$^5$—;
n is 2 or 3;
R$^2$ is selected from hydrogen or C$_{1-8}$ alkyl;
R$^3$ is C$_{5-6}$ alkyl-OH, wherein the said C$_{5-6}$ alkyl group is further substituted by an additional 3 or 4 —OH groups; and $R^4$ and $R^5$ are selected from hydrogen or $C_{1-4}$ alkyl;

or a pharmaceutically acceptable salt thereof.

This specification also describes, in part, pharmaceutical compositions which comprise a compound of the formula (I), or a pharmaceutically acceptable salt thereof, and a pharmaceutically acceptable adjuvant, diluent or carrier.

This specification also describes, in part, a compound of formula (I), or a pharmaceutically acceptable salt thereof, for use in therapy.

This specification also describes, in part, a compound of formula (I), or a pharmaceutically acceptable salt thereof, for the treatment or prevention of an ENaC mediated disease state.

This specification also describes, in part, a compound of formula (I), or a pharmaceutically acceptable salt thereof, in the manufacture of a medicament for the treatment or prevention of an ENaC mediated disease state.

This specification also describes, in part, a method of treating or of preventing an ENaC mediated disease state in a mammal suffering from, or at risk of, said disease, which comprises administering to a mammal in need of such treatment a therapeutically effective amount of a compound of formula (I), or a pharmaceutically acceptable salt thereof.

Further aspects of the invention will be apparent to one skilled in the art from reading this specification.

The compounds of the invention may exist in salt-form or in non-salt form (ie. as a free base), and the present invention covers both salt forms and non-salt forms.

Compounds described in this specification may form acid addition salts. In general, an acid addition salt can be prepared using various inorganic or organic acids. Such salts can typically be formed by, for example, mixing the compound with an acid (e.g. a stoichiometric amount of an acid) using various methods known in the art. This mixing may occur in water, an organic solvent (e.g. ether, ethyl acetate, ethanol, methanol, isopropanol, or acetonitrile), or an aqueous/organic mixture.

In another aspect of the invention acid addition salts are, for example, trifluoroacetate, formate, acetate or hydrochloric.

The skilled person will be aware of the general principles and techniques of preparing pharmaceutical salts, such as those described in, for example, Berge et al., *J. Pharm. Sci.*, 66, 1-19 (1977).

Compounds and salts described in this specification may include one or more chiral (i.e. asymmetric) centres. To the extent a structure or chemical name in this specification does not indicate the chirality, the structure or name is intended to encompass any single stereoisomer (i.e. any single chiral isomer) corresponding to that structure or name, as well as any mixture of stereoisomers (e.g. a racemate). In some embodiments, a single stereoisomer is obtained by isolating it from a mixture of isomers (e.g. a racemate) using, for example, chiral chromatographic separation. In other embodiments, a single stereoisomer is obtained through direct synthesis from, for example, a chiral starting material.

When in solid crystalline form a compound of formula (I) can be in the form of a co-crystal with another chemical entity and the invention encompasses all such co-crystals.

The compounds of the invention may exist as a solvate (such as a hydrate) as well as unsolvated forms, and the present invention covers all such solvates.

Compounds and salts described in this specification may exist in various tautomeric forms and the invention encompasses all such tautomeric forms. "Tautomers" are structural isomers that exist in equilibrium resulting from the migration of a hydrogen atom.

Compounds and salts described in this specification may be isotopically-labeled (or "radio-labeled"). In that instance, one or more atoms are replaced by an atom having an atomic mass or mass number different from the atomic mass or mass number typically found in nature. Examples of radionuclides that may be incorporated include $^2H$ (also written as "D" for deuterium), $^3H$ (also written as "T" for tritium), $^{11}C$, $^{13}C$, $^{14}C$, $^{13}N$, $^{15}N$, $^{15}O$, $^{17}O$, $^{18}O$ and $^{36}Cl$. The radionuclide that is used will depend on the specific application of that radio-labeled derivative. For example, for in vitro receptor labeling and competition assays, $^3H$ or $^{14}C$ are often useful. For radio-imaging applications, $^{11}C$ is often useful. In some embodiments, the radionuclide is $^3H$. In some embodiments, the radionuclide is $^{14}C$. In some embodiments, the radionuclide is $^{11}C$.

Alkyl groups and moieties are straight or branched chain, e.g. $C_{1-8}$ alkyl, $C_{1-6}$ alkyl, $C_{1-4}$ alkyl or $C_{5-6}$ alkyl. Examples of alkyl groups are methyl, ethyl, n-propyl, iso-propyl, n-butyl, t-butyl, n-pentyl, n-hexyl, n-heptyl and n-octyl, such as methyl or n-hexyl.

Heterocyclyl is a non-aromatic 5 or 6 membered ring comprising one or two heteroatoms independently selected from nitrogen, oxygen or sulphur; or an N-oxide thereof, or an S-oxide or S-dioxide thereof. An example of a heterocyclyl is a non-aromatic 5 or 6 membered ring comprising one or two nitrogen atoms; or an N-oxide thereof, or an S-oxide or S-dioxide thereof, for example, pyrrolidinyl or piperidinyl, such as piperidin-4-yl. For the avoidance of doubt, substituents on the heterocyclyl ring may be linked via either a carbon atom or a heteroatom.

The term "pharmaceutically acceptable" is used to characterize a moiety (e.g. a salt, dosage form or excipient) as being suitable for use in the intended patient.

In one particular aspect $R^1$ is substituted to the phenyl group in the 2-position relative to the point of attachment to the remainder of the formula (I).

In a further aspect $R^1$ is $C_{1-4}$ alkyl.

In a further aspect $R^1$ is methyl.

In a further aspect m is 1.

In a still further aspect A is selected from phenyl or piperidinyl.

In a further aspect A is phenyl.

In a further aspect A is piperidinyl.

In another aspect X is —C(=O)—NR$^4$—.

In a further aspect X is —C(=O)—NH—.

In one aspect, where the group X is —C(=O)—NR$^4$—, then the carbonyl of X is linked to A and the amino group of X to $(CH_2)_n$. In another aspect, where the group X is —C(=O)—NR$^4$— then the amino group of X is linked to A and the carbonyl group of X to $(CH_2)_n$.

In one aspect, where the group X is —O—C(=O)—NR$^5$—, then the ether oxygen of X is linked to A and the amino group of X to $(CH_2)_n$. In another aspect, where the group X is —O—C(=O)—NR$^5$—, then the amino group of X is linked to A and the ether oxygen of X to $(CH_2)_n$.

In another aspect the group X is substituted to the group A in the 4-position relative to the point of attachment to the remainder of the compound of formula (I).

In another aspect n is 2.

In a further aspect $R^2$ is $C_{1-8}$ alkyl.

In a still further aspect $R^2$ is n-hexyl.

In another aspect, $R^3$ is $C_5$ alkyl-OH, wherein the said $C_5$ alkyl group is further substituted by an additional 3 —OH groups.

In another aspect, $R^3$ is $C_6$ alkyl-OH, wherein the said $C_6$ alkyl group is further substituted by an additional 4 —OH groups.

In a further aspect $R^3$ is selected from the following:

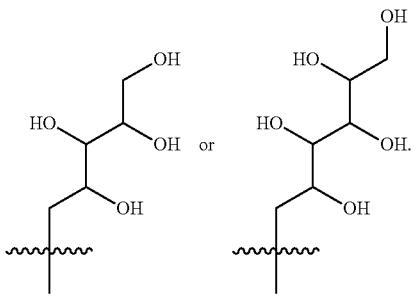 [SMILES: *CC(O)C(O)C(O)CO ; "or" ; *CC(O)C(O)C(O)C(O)CO]

In another aspect, $R^3$ is selected from the following:

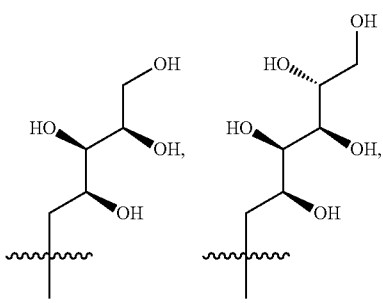

In a further aspect $R^3$ is selected from the following:

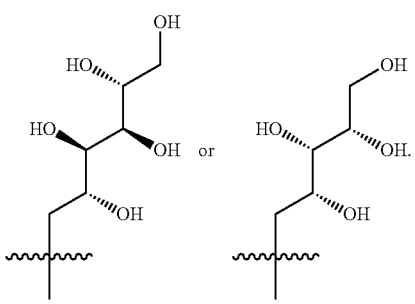

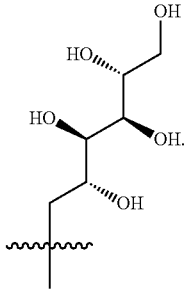

In another aspect, $R^3$ is selected from (2S,3R,4R)-2,3,4,5-tetrahydroxypentyl, (2S,3R,4R 5R)-2,3,4,5,6-pentahydroxyhexyl, (2R,3R,4R,5R)-2,3,4,5,6-pentahydroxyhexyl or (2R,3S,4S)-2,3,4,5-tetrahydroxypentyl.

In a further aspect, $R^3$ is selected from (2S,3R,4R)-2,3,4,5-tetrahydroxypentyl, (2S,3R,4R 5R)-2,3,4,5,6-pentahydroxyhexyl or (2R,3R,4R,5R)-2,3,4,5,6-pentahydroxyhexyl.

In another aspect $R^5$ is hydrogen.

In a further aspect, $R^1$ is $C_{1-4}$ alkyl; m is 1 or 2; A is phenyl or piperidinyl; X is selected from —C(=O)—, —C(=O)—NR⁴— or —O—C(=O)—NR⁵—; n is 2 or 3; $R^2$ is hydrogen or $C_{1-8}$ alkyl; $R^3$ is $C_{5-6}$ alkyl-OH, wherein the said $C_{5-6}$ alkyl group is further substituted by an additional 3 or 4 —OH groups; and $R^4$ and $R^5$ are both hydrogen.

In a further aspect, $R^1$ is $C_{1-4}$ alkyl; m is 1; A is phenyl or piperidinyl; X is —C(=O)—NH—; n is 2; $R^2$ is $C_{1-8}$ alkyl; $R^3$ is selected from the following:

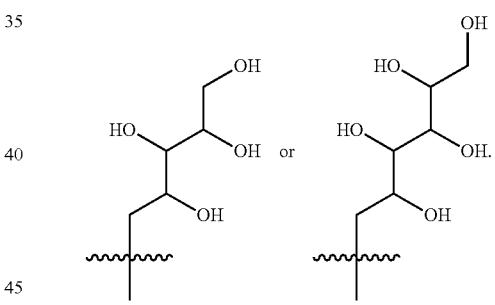

In a further aspect, $R^1$ is $C_{1-4}$ alkyl; m is 1; A is phenyl; X is —C(=O)—NH—; n is 2; $R^2$ is $C_{1-8}$ alkyl; and $R^3$ is selected from the following:

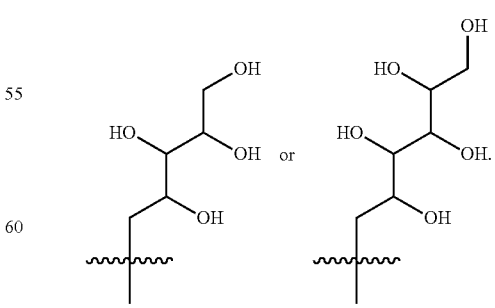

In a further aspect of the invention the compounds of the invention exhibit R stereochemistry at the carbon centre marked with an asterisk (*) in formula (Ia) below:

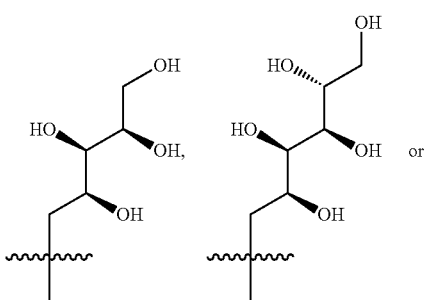

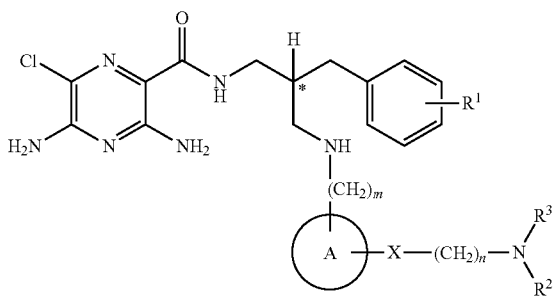

(Ia)

An example of a compound of the invention is:
3,5-diamino-6-chloro-N-(2-(2-methylbenzyl)-3-(((1-(3-((2,3,4,5-tetrahydroxypentyl)amino)propanoyl)piperidin-4-yl)methyl)amino)propyl)pyrazine-2-carboxamide;
3,5-diamino-6-chloro-N-(3-((4-((2-(hexyl(2,3,4,5-tetrahydroxypentyl)amino)ethyl)carbamoyl)benzyl)amino)-2-(2-methylbenzyl)propyl)pyrazine-2-carboxamide;
3,5-diamino-6-chloro-N-(3-((1-(2-(hexyl(2,3,4,5,6-pentahydroxyhexyl)amino)ethylcarbamoyl)piperidin-4-yl)methylamino)-2-(2-methylbenzyl)propyl)pyrazine-2-carboxamide;
3,5-diamino-6-chloro-N-(3-((1-(3-(hexyl(2,3,4,5,6-pentahydroxyhexyl)amino)propanoyl)piperidin-4-yl)methylamino)-2-(2-methylbenzyl)propyl)pyrazine-2-carboxamide;
3,5-diamino-6-chloro-N-(3-((1-(3-(hexyl(2,3,4,5-tetrahydroxypentyl)amino)propanoyl)piperidin-4-yl)methylamino)-2-(2-methylbenzyl)propyl)pyrazine-2-carboxamide;
3,5-diamino-6-chloro-N-(3-((1-(4-(hexyl(2,3,4,5,6-pentahydroxyhexyl)amino)butanoyl)piperidin-4-yl)methylamino)-2-(2-methylbenzyl)propyl)pyrazine-2-carboxamide;
3,5-diamino-6-chloro-N-(2-(2-methylbenzyl)-3-((1-(3-(2,3,4,5,6-pentahydroxyhexylamino)propanoyl)piperidin-4-yl)methylamino)propyl)pyrazine-2-carboxamide;
3,5-diamino-6-chloro-N-(3-((1-(3-(hexyl(2,3,4,5,6-pentahydroxyhexyl)amino)propanoyl)piperidin-4-yl)methylamino)-2-(2-methylbenzyl)propyl)pyrazine-2-carboxamide;
3,5-diamino-6-chloro-N-(3-((4-((2-(hexyl(2,3,4,5,6-pentahydroxyhexyl)amino)ethyl)carbamoyl)benzyl)amino)-2-(2-methylbenzyl)propyl)pyrazine-2-carboxamide;
3,5-diamino-6-chloro-N-(3-((4-((2-(hexyl(2,3,4,5,6-pentahydroxyhexyl)amino)ethyl)carbamoyl)benzyl)amino)-2-(2-methylbenzyl)propyl)pyrazine-2-carboxamide;
4-((3-(3,5-diamino-6-chloropyrazine-2-carboxamido)-2-(2-methylbenzyl)propylamino)methyl)phenyl 2-(hexyl(2,3,4,5,6-pentahydroxyhexyl)amino)ethylcarbamate;
3,5-diamino-6-chloro-N-(3-((4-((2-(hexyl(2,3,4,5,6-pentahydroxyhexyl)amino)ethyl)carbamoyl)phenethyl)amino)-2-(2-methylbenzyl)propyl)pyrazine-2-carboxamide;
3,5-diamino-6-chloro-N-(3-((4-((2-(hexyl(2,3,4,5-tetrahydroxypentyl)amino)ethyl)carbamoyl)phenethyl)amino)-2-(2-methylbenzyl)propyl)pyrazine-2-carboxamide;
3,5-diamino-6-chloro-N-(3-((4-((2-(hexyl(2,3,4,5-tetrahydroxypentyl)amino)ethyl)carbamoyl)benzyl)amino)-2-(2-methylbenzyl)propyl)pyrazine-2-carboxamide;
3,5-diamino-6-chloro-N-(3-(3-(2-(hexyl(2,3,4,5,6-pentahydroxyhexyl)amino)ethylcarbamoyl)phenethylamino)-2-(2-methylbenzyl)propyl)pyrazine-2-carboxamide;
or a pharmaceutically acceptable salt thereof.

A further example of a compound of the invention is:
3,5-diamino-6-chloro-N-(2-(2-methylbenzyl)-3-(((1-(3-(((2S,3R,4R)-2,3,4,5-tetrahydroxypentyl)amino)propanoyl)piperidin-4-yl)methyl)amino)propyl)pyrazine-2-carboxamide;
3,5-diamino-6-chloro-N-(3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide;
3,5-diamino-6-chloro-N-(3-((1-(2-(hexyl((2S,3R,4R,5R)-2,3,4,5,6-pentahydroxyhexyl)amino)ethylcarbamoyl)piperidin-4-yl)methylamino)-2-(2-methylbenzyl)propyl)pyrazine-2-carboxamide;
3,5-diamino-6-chloro-N-(3-((1-(3-(hexyl((2S,3R,4R,5R)-2,3,4,5,6-pentahydroxyhexyl)amino)propanoyl)piperidin-4-yl)methylamino)-2-(2-methylbenzyl)propyl)pyrazine-2-carboxamide;
3,5-diamino-6-chloro-N-(3-((1-(3-(hexyl((2S,3R,4R)-2,3,4,5-tetrahydroxypentyl)amino)propanoyl)piperidin-4-yl)methylamino)-2-(2-methylbenzyl)propyl)pyrazine-2-carboxamide;
3,5-diamino-6-chloro-N-(3-((1-(4-(hexyl((2S,3R,4R,5R)-2,3,4,5,6-pentahydroxyhexyl)amino)butanoyl)piperidin-4-yl)methylamino)-2-(2-methylbenzyl)propyl)pyrazine-2-carboxamide;
3,5-diamino-6-chloro-N-(2-(2-methylbenzyl)-3-((1-(3-((2S,3R,4R,5R)-2,3,4,5,6-pentahydroxyhexylamino)propanoyl)piperidin-4-yl)methylamino)propyl)pyrazine-2-carboxamide;
3,5-diamino-6-chloro-N-(3-((1-(3-(hexyl((2R,3R,4R,5R)-2,3,4,5,6-pentahydroxyhexyl)amino)propanoyl)piperidin-4-yl)methylamino)-2-(2-methylbenzyl)propyl)pyrazine-2-carboxamide;
3,5-diamino-6-chloro-N-(3-((4-((2-(hexyl((2R,3R,4R,5R)-2,3,4,5,6-pentahydroxyhexyl)amino)ethyl)carbamoyl)benzyl)amino)-2-(2-methylbenzyl)propyl)pyrazine-2-carboxamide;
3,5-diamino-6-chloro-N-(3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide;
4-((3-(3,5-diamino-6-chloropyrazine-2-carboxamido)-2-(2-methylbenzyl)propylamino)methyl)phenyl 2-(hexyl((2S,3R,4R,5R)-2,3,4,5,6-pentahydroxyhexyl)amino)ethylcarbamate;
3,5-diamino-6-chloro-N-(3-((4-((2-(hexyl((2S,3R,4R,5R)-2,3,4,5,6-pentahydroxyhexyl)amino)ethyl)carbamoyl)phenethyl)amino)-2-(2-methylbenzyl)propyl)pyrazine-2-carboxamide;
3,5-diamino-6-chloro-N-(3-((4-((2-(hexyl((2S,3R,4R)-2,3,4,5-tetrahydroxypentyl)amino)ethyl)carbamoyl)phenethyl)amino)-2-(2-methylbenzyl)propyl)pyrazine-2-carboxamide;
3,5-diamino-6-chloro-N-(3-((4-((2-(hexyl((2R,3S,4S)-2,3,4,5-tetrahydroxypentyl)amino)ethyl)carbamoyl)benzyl)amino)-2-(2-methylbenzyl)propyl)pyrazine-2-carboxamide;
3,5-diamino-6-chloro-N-(3-(3-(2-(hexyl((2S,3R,4R,5R)-2,3,4,5,6-pentahydroxyhexyl)amino)ethylcarbamoyl)phenethylamino)-2-(2-methylbenzyl)propyl)pyrazine-2-carboxamide;
or a pharmaceutically acceptable salt thereof.

A further example of a compound of the invention is:
3,5-diamino-6-chloro-N—((R)-2-(2-methylbenzyl)-3-(((1-(3-(((2S,3R,4R)-2,3,4,5-tetrahydroxypentyl)amino)propanoyl)piperidin-4-yl)methyl)amino)propyl)pyrazine-2-carboxamide;
3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide;

3,5-diamino-6-chloro-N—((R)-3-((1-(2-(hexyl((2S,3R,4R,5R)-2,3,4,5,6-pentahydroxyhexyl)amino)ethyl)carbamoyl)piperidin-4-yl)methylamino)-2-(2-methylbenzyl)propyl)pyrazine-2-carboxamide;

3,5-diamino-6-chloro-N—((R)-3-((1-(3-(hexyl((2S,3R,4R,5R)-2,3,4,5,6-pentahydroxyhexyl)amino)propanoyl)piperidin-4-yl)methylamino)-2-(2-methylbenzyl)propyl)pyrazine-2-carboxamide;

3,5-diamino-6-chloro-N—((R)-3-((1-(3-(hexyl((2S,3R,4R)-2,3,4,5-tetrahydroxypentyl)amino)propanoyl)piperidin-4-yl)methylamino)-2-(2-methylbenzyl)propyl)pyrazine-2-carboxamide;

3,5-diamino-6-chloro-N—((R)-3-((1-(4-(hexyl((2S,3R,4R,5R)-2,3,4,5,6-pentahydroxyhexyl)amino)butanoyl)piperidin-4-yl)methylamino)-2-(2-methylbenzyl)propyl)pyrazine-2-carboxamide;

3,5-diamino-6-chloro-N—((R)-2-(2-methylbenzyl)-3-((1-(3-((2S,3R,4R,5R)-2,3,4,5,6-pentahydroxyhexylamino)propanoyl)piperidin-4-yl)methylamino)propyl)pyrazine-2-carboxamide;

3,5-diamino-6-chloro-N—((R)-3-((1-(3-(hexyl((2R,3R,4R,5R)-2,3,4,5,6-pentahydroxyhexyl)amino)propanoyl)piperidin-4-yl)methylamino)-2-(2-methylbenzyl)propyl)pyrazine-2-carboxamide;

3,5-diamino-6-chloro-N—((R)-3-((4-((2-(hexyl((2R,3R,4R,5R)-2,3,4,5,6-pentahydroxyhexyl)amino)ethyl)carbamoyl)benzyl)amino)-2-(2-methylbenzyl)propyl)pyrazine-2-carboxamide;

3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide;

4-(((R)-3-(3,5-diamino-6-chloropyrazine-2-carboxamido)-2-(2-methylbenzyl)propylamino)methyl)phenyl 2-(hexyl((2S,3R,4R,5R)-2,3,4,5,6-pentahydroxyhexyl)amino)ethylcarbamate;

3,5-diamino-6-chloro-N—((R)-3-((4-((2-(hexyl((2S,3R,4R,5R)-2,3,4,5,6-pentahydroxyhexyl)amino)ethyl)carbamoyl)phenethyl)amino)-2-(2-methylbenzyl)propyl)pyrazine-2-carboxamide;

3,5-diamino-6-chloro-N—((R)-3-((4-((2-(hexyl((2S,3R,4R)-2,3,4,5-tetrahydroxypentyl)amino)ethyl)carbamoyl)phenethyl)amino)-2-(2-methylbenzyl)propyl)pyrazine-2-carboxamide;

3,5-diamino-6-chloro-N—((S)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide;

3,5-diamino-6-chloro-N—((S)-3-((4-((2-(hexyl((2R,3S,4S)-2,3,4,5-tetrahydroxypentyl)amino)ethyl)carbamoyl)benzyl)amino)-2-(2-methylbenzyl)propyl)pyrazine-2-carboxamide;

3,5-diamino-6-chloro-N—((R)-3-(3-(2-(hexyl((2S,3R,4R,5R)-2,3,4,5,6-pentahydroxyhexyl)amino)ethylcarbamoyl)phenethylamino)-2-(2-methylbenzyl)propyl)pyrazine-2-carboxamide;

or a pharmaceutically acceptable salt thereof.

A further feature of the invention is any of the embodiments described above with the proviso that any of the specific Examples are individually disclaimed. For example, a further feature is any of the embodiments described above with the proviso that any of the compounds selected from the above list of examples of compounds of the invention are individually disclaimed.

In some embodiments, the compound is a compound of formula (I) excluding at least one compound recited in the Examples below. To illustrate, in some such embodiments, the compound is a compound of formula (I) excluding the compound disclosed in Example X, wherein X may be 1, 2, 3, etc. In other embodiments, the compound is a compound of formula (I) excluding the compounds disclosed in Examples Y, wherein Y may be any combination of 1, 2, 3, etc.

Compounds of formula (I) may be prepared from compounds of formula (II) according to scheme 1, wherein $R^1$, $R^2$, $R^3$, A, X, m and n are as defined in formula (I), and wherein p=m−1.

Scheme 1:

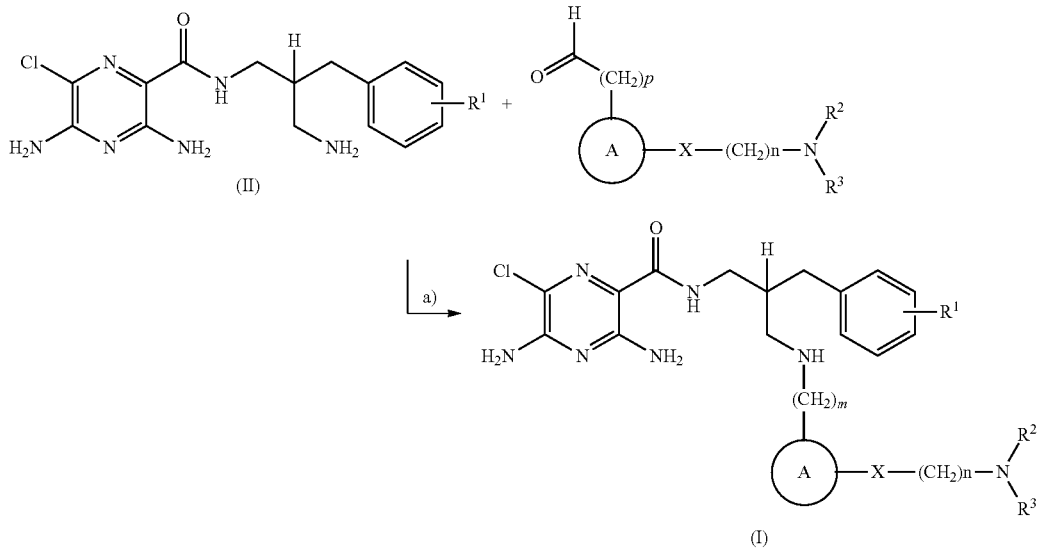

a) NaH(OAc)₃, AcOH, THF or NaBH₄, MeOH

Alternatively, compounds of formula (I) may be prepared in a manner described in scheme 2 wherein $R^1$, $R^2$, $R^3$, A, X, m and n are as defined in formula (I), and wherein Y is halogen, for example, chlorine, bromine or iodine and p=m−1.

Scheme 2:

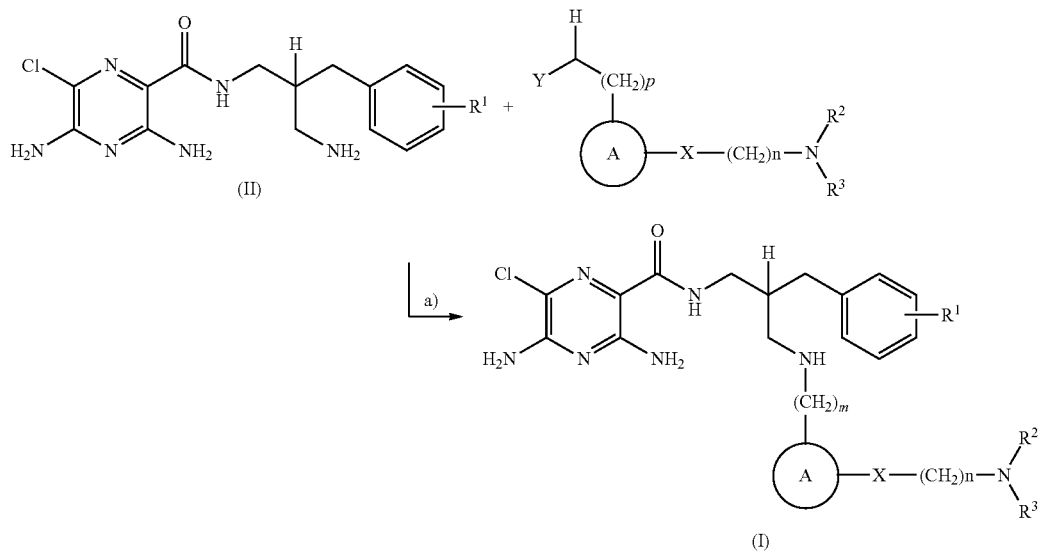

a) NaH or $K_2CO_3$ or $Cs_2CO_3$ or DIEA, DMF.

Alternatively, compounds of formula (I) may be prepared by the introduction of $R^3$ in a final step by reductive alkylation of suitable polyhydroxylated alkylaldehydes such as hexoses or pentoses (the $R^3$-aldehyde), as described in scheme 3, and wherein $R^1$, $R^2$, $R^3$, A, X, m and n are as defined in formula (I). The polyhydroxyalkyl chains present in $R^3$ may be protected by any suitable alcohol protection groups, for example as described by P. G. M. Wuts, Th. W. Greene, Greene's Protective Groups in Organic Synthesis, Wiley-Interscience, New York, 2006. Furthermore, as the skilled person will be aware, and as described in the Examples herein, additional amino groups present in the compounds of formula (II) may be protected by suitable amino protection groups, for example as described in Wuts and Greene (above), such as by di-tertbutyl dicarbonate (Boc) or fluorenylmethyloxycarbonyl (FMoc) protecting groups.

Scheme 3:

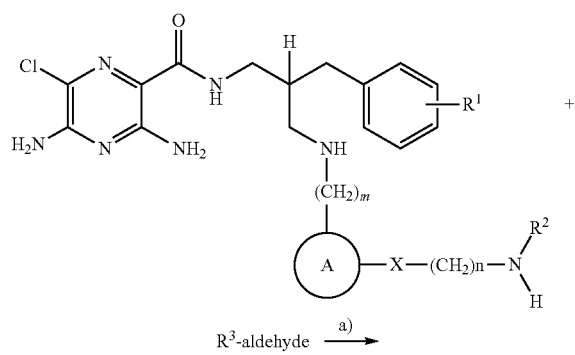

-continued

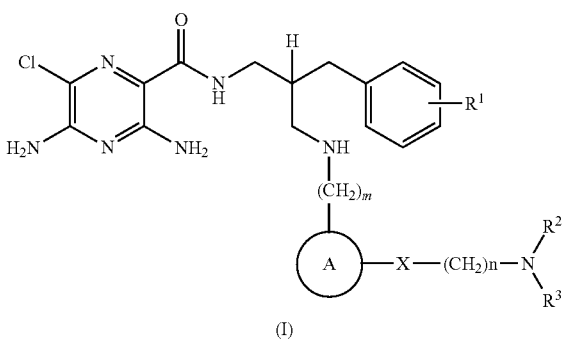

a) $NaBH(OAc)_3$ or $NaBH_3CN$, AcOH, THF or $NaBH_4$, MeOH

Compounds of formula (II) may be prepared enantioselectively by methods as described in scheme 5 (J. C. D. Müller-Hartwieg, L. La Vecchia, H. Meyer, A. K. Beck, D. Seebach, Org. Synth. 85 (2008), 295) or by the method shown in schemes 4, and 6, wherein $R^1$ is as defined in formula (I).

Scheme 4:
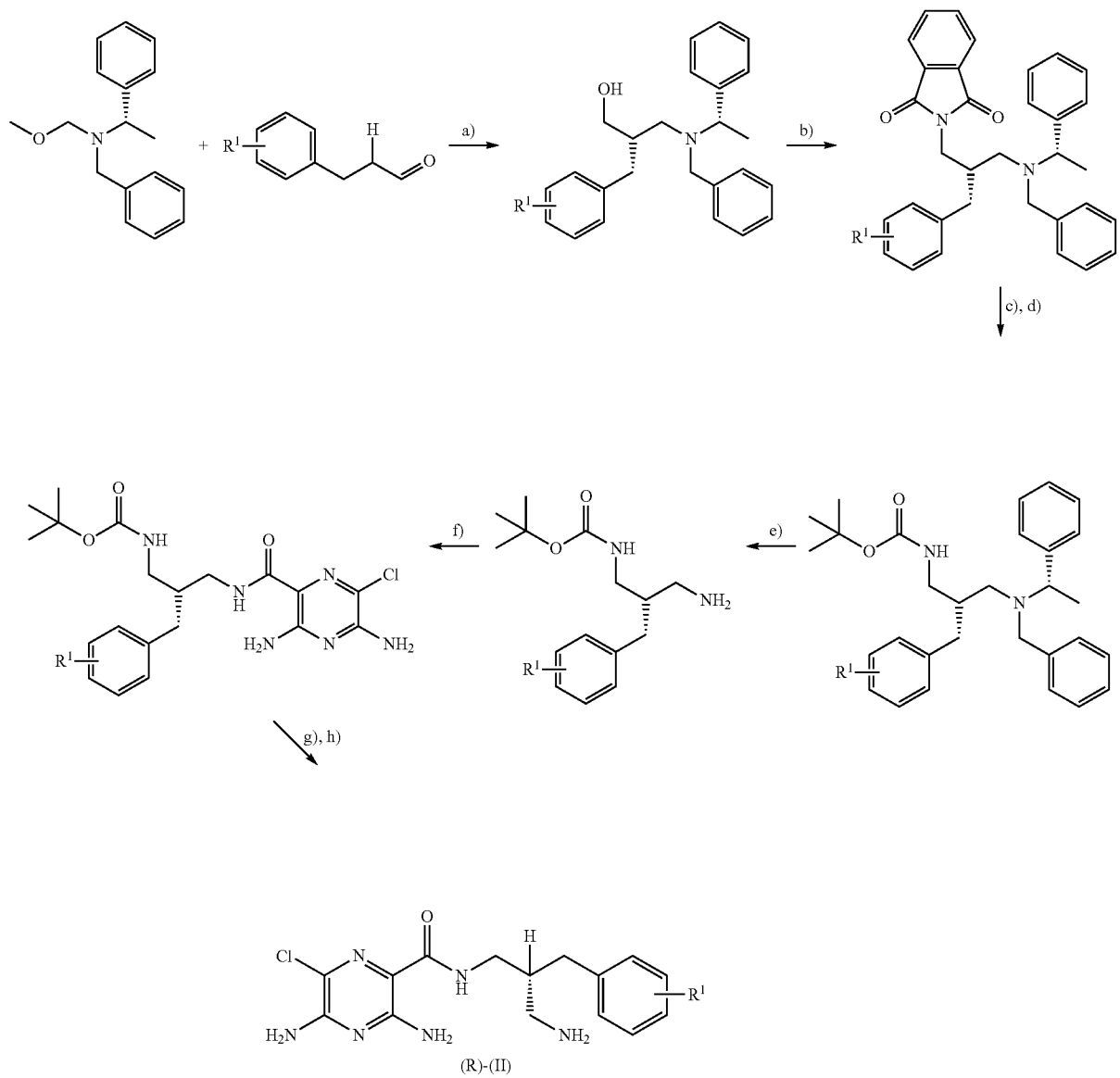
a) i) L-proline, DMF, ii) NaBH₄, MeOH; b) Phtalimide, PPh₃, DEAD, THF; c) CH₃NH₂, EtOH, d) Boc₂O, DCM, TEA; e) Pd(OH)₂, H₂, MeOH, 70 psi; f) (3-chloro-5-(1H-imidazol-1-ylcarbonyl)pyrazine-2, 6-diamine, DIPEA, NMP; g) TFA, DCM; h) NaOH, THF.
Scheme 5:
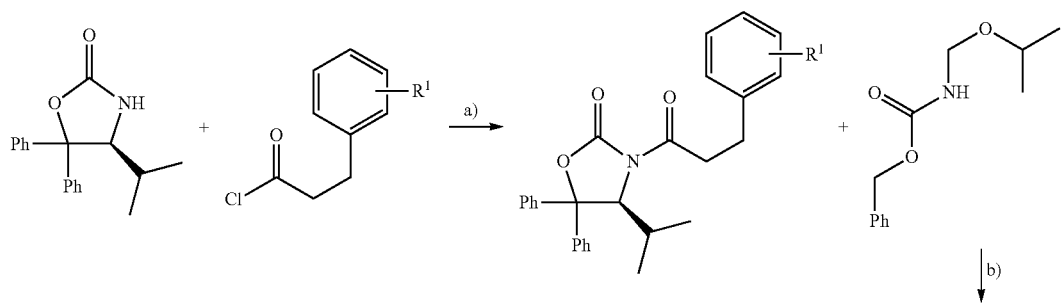

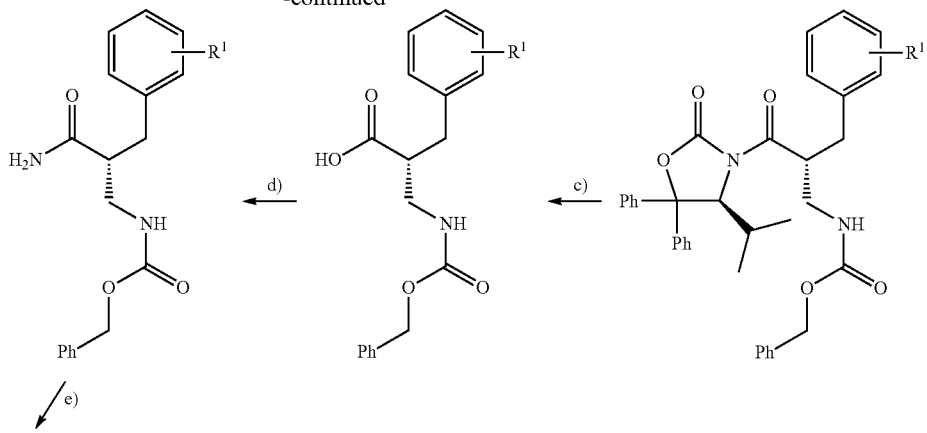
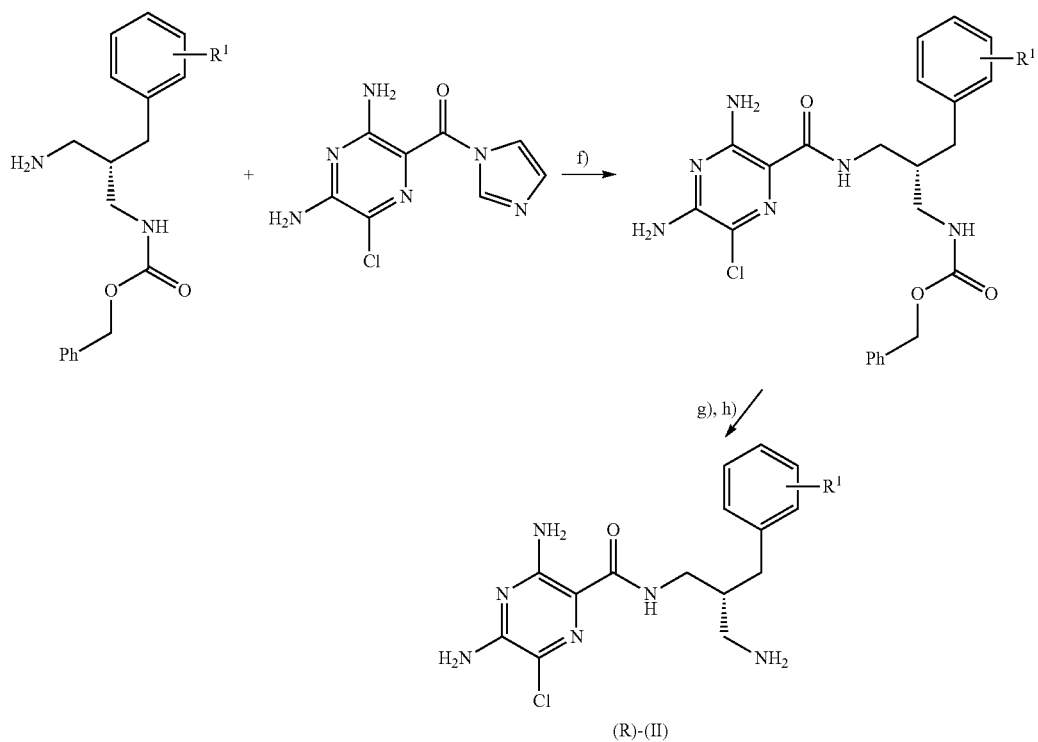
a) BuLi, THF; b) TiCl₄, TEA, DCM; c) LiOH, H₂O₂, THF, H₂O; d) (COCl)₂, NH₄OH, DCM; e) BH₃*THF; f) NMP; g) TFA, DCM; h) NaOH, THF.
Scheme 6:
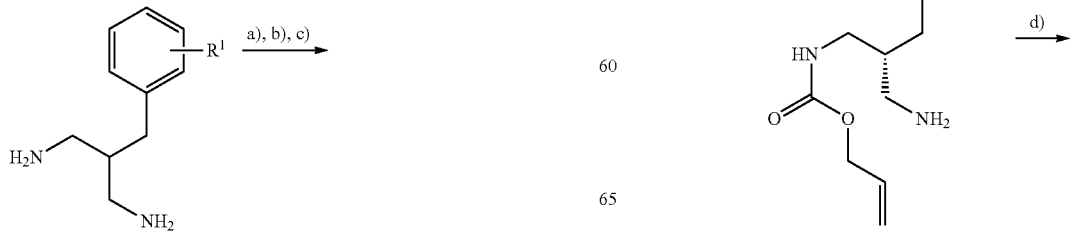

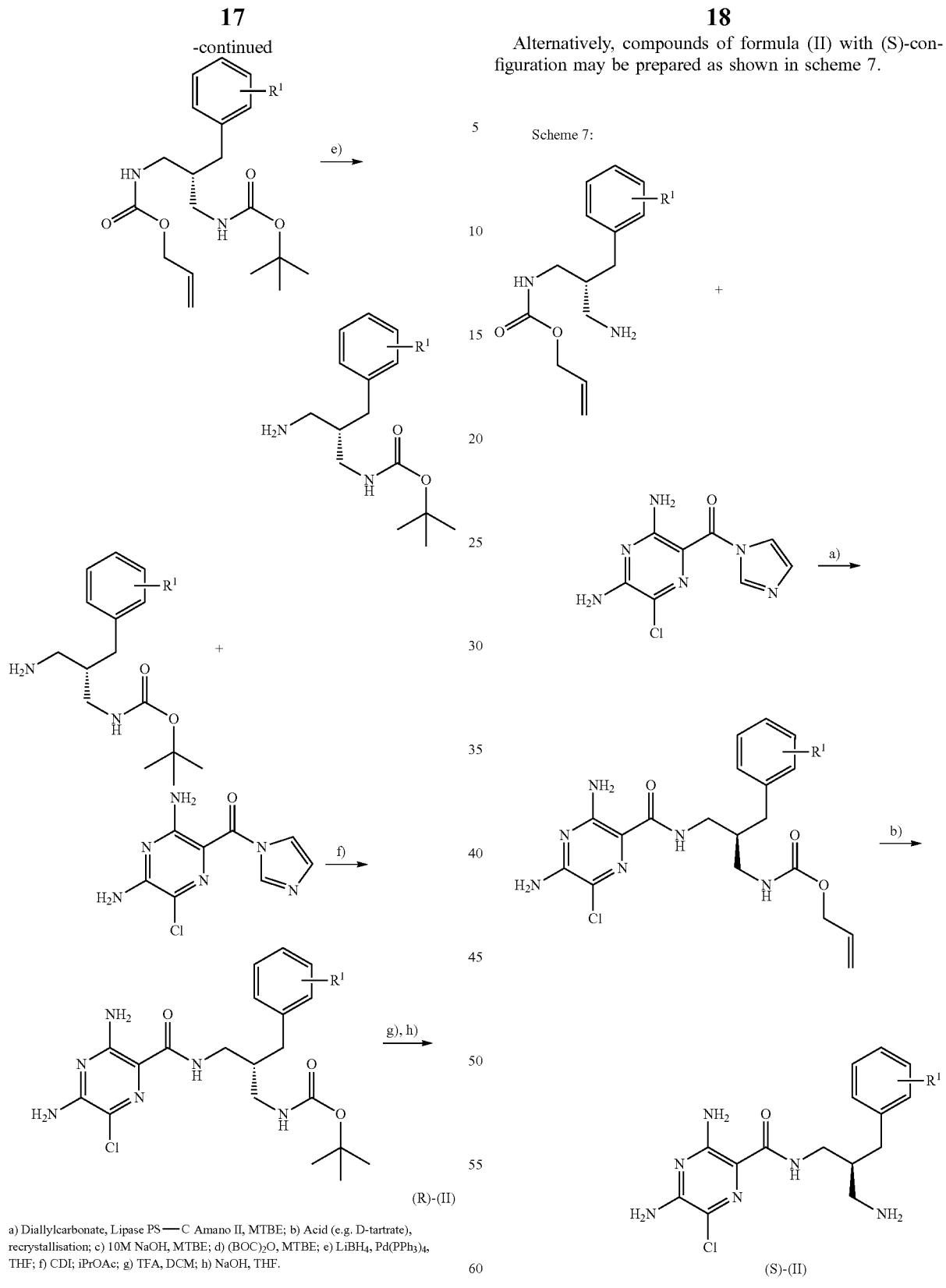

Alternatively, compounds of formula (II) with (S)-configuration may be prepared as shown in scheme 7.

a) Diallylcarbonate, Lipase PS—C Amano II, MTBE; b) Acid (e.g. D-tartrate), recrystallisation; c) 10M NaOH, MTBE; d) (BOC)$_2$O, MTBE; e) LiBH$_4$, Pd(PPh$_3$)$_4$, THF; f) CDI; iPrOAc; g) TFA, DCM; h) NaOH, THF.

a) CDI: iPrOAc; b) LiBH$_4$, Pd(PPh$_3$)$_4$, THF.

Schemes 4, 5 and 6 describe access to the (R)-enantiomer of compounds of formula (II). The reactions described in these schemes may equally be applied to access the related (S)-enantiomer by using starting materials of reversed absolute configuration or enzymes of different stereo specificity.

The method described at step (a) of Scheme 6 comprises the enzyme mediated desymmetrization of diamine (III) using diallylcarbonate.

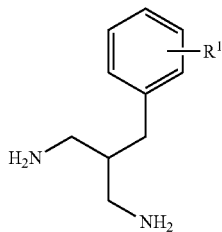

(III)

Suitable enzymes for this reaction include lipases, in particular lipases which originate from *Candida Antarctica* or *Pseudomonas Cepacia*. Suitable enzymes include IMM CALB (*Candida Antarctica* Lipase B), IMM CALBY (*Candida Antarctica* Lipase B), Novozym 435 (*Candida Antarctica* Lipase B), Amano Lipase PS-C1 (*Pseudomonas Cepacia* Lipase), Amano Lipase PS-IM (*Pseudomonas Cepacia* Lipase) and Amano Lipase PS-D (*Pseudomonas Cepacia* Lipase), such as Amano Lipase PS-C1, Amano Lipase PS-D and Amano Lipase PS-IM. The reaction can be carried out in a range of polar and non-polar solvents, and mixtures thereof, including tert-butyl dimethyl ether (TBME), tetrahydrofuran (THF), methyl-THF (MeTHF, for example 2-methyl-THF), heptanes, cyclohexane and toluene, such as MeTHF. The reaction can be carried out at a range of temperatures, for example 0° C. to 50° C., for example 15° C. to 35° C., for example about 30° C. The enantiomeric excess of the resulting crude product can optionally be increased by resolution processes known to those skilled in the art, for example by crystallisation from a tartrate salt.

In a further aspect of the invention there is provided a process for preparing a compound of formula (IV), wherein $R^1$ is as defined above (such as the compound (R)-allyl-(3-amino-2-(2-methylbenzyl)propyl)carbamate):

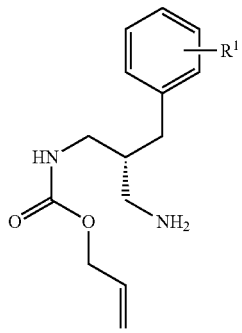

(IV)

comprising the enzyme mediated desymmetrisation of diamine (III) in the presence of diallycarbonate, and optionally thereafter carrying out an enantiomeric resolution. In a further aspect, the enzyme is selected from one which originates from either *Candida Antarctica* or *Pseudomonas Cepacia*, such as IMM CALB (*Candida Antarctica* Lipase B), IMM CALBY (*Candida Antarctica* Lipase B), Novozym 435 (*Candida Antarctica* Lipase B), Amano Lipase PS-C1 (*Pseudomonas Cepacia* Lipase), Amano Lipase PS-IM (*Pseudomonas Cepacia* Lipase) and Amano Lipase PS-D (*Pseudomonas Cepacia* Lipase). In another aspect, the enzyme is selected from Amano Lipase PS-C1, Amano Lipase PS-D and Amano Lipase PS-IM, such as Amino Lipase PS-IM.

In another aspect of the invention there is provided the compound (R)-allyl-(3-amino-2-(2-methylbenzyl)propyl)carbamate.

In a further aspect there is provided the use of the compound (R)-allyl-(3-amino-2-(2-methylbenzyl)propyl)carbamate as a pharmaceutical intermediate. In a further aspect, there is provided the use of the compound (R)-allyl-(3-amino-2-(2-methylbenzyl)propyl)carbamate as an intermediate in the manufacture of a compound of formula (I).

Detailed processes to the compounds of the invention are further described in the Examples below.

Compounds and salts described in this specification generally may be used in methods to treat various disorders in animals, particularly mammals. Mammals include, for example, humans.

The compounds of the invention, and pharmaceutically acceptable salts thereof, have activity as pharmaceuticals, in particular as modulators of the ENaC, and can be used in the treatment of respiratory tract disease, diseases of the bone and joints, and other auto-immune and allergic disorders.

Disease states that may be treated with a compound of the invention, or a pharmaceutically acceptable salt thereof, include, but are not limited to, diseases of the respiratory tract, such as: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, idiopathic pulmonary fibrosis, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; or adult respiratory distress syndrome (ARDS).

In a further aspect of the invention, the diseases of the respiratory tract which may be treated with a compound of the invention, or a pharmaceutically salt thereof, includes: chronic obstructive pulmonary disease (COPD); bronchitis, including infectious and eosinophilic bronchitis; bronchiectasis; cystic fibrosis; antitussive activity including treatment of chronic cough associated with inflammatory and secretory conditions of the airways, and iatrogenic cough; asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness.

In a still further aspect of the invention, the disease states which may be treated with a compound of the invention, or a pharmaceutically salt thereof, includes chronic obstructive pulmonary disease (COPD), cystic fibrosis, asthma, chronic bronchitis and bronchiectasis.

In a yet further aspect of the invention, the disease state which may be treated with a compound of the invention, or a pharmaceutically salt thereof, is chronic obstructive pulmonary disease (COPD).

In one aspect of the invention there is provided a compound of formula (I), or a pharmaceutically acceptable salt thereof, for the treatment of COPD.

In a further aspect of the invention there is provided a compound of formula (I), or a pharmaceutically acceptable salt thereof, in the manufacture of a medicament for the treatment of COPD.

In a further aspect of the invention there is provided a method of treating or preventing COPD in a mammal suffering from, or at risk of, said disease, which comprises administering to a mammal in need of such treatment a therapeutically effective amount of a compound of formula (I), or a pharmaceutically acceptable salt thereof.

In a yet further aspect of the invention, the disease state which may be treated with a compound of the invention, or a pharmaceutically salt thereof, is cystic fibrosis (CF).

In one aspect of the invention there is provided a compound of formula (I), or a pharmaceutically acceptable salt thereof, for the treatment of CF.

In a further aspect of the invention there is provided a compound of formula (I), or a pharmaceutically acceptable salt thereof, in the manufacture of a medicament for the treatment of CF.

In a further aspect of the invention there is provided a method of treating or preventing CF in a mammal suffering from, or at risk of, said disease, which comprises administering to a mammal in need of such treatment a therapeutically effective amount of a compound of formula (I), or a pharmaceutically acceptable salt thereof.

When a compound or salt described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

In some embodiments in which a combination therapy is used, the amount of the compound or salt described in this specification and the amount of the other pharmaceutically active agent(s) are, when combined, therapeutically effective to treat a targeted disorder in the animal patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound or salt and an approved or otherwise published dosage range(s) of the other pharmaceutically active compound(s).

In order to use a compound of the invention, or a pharmaceutically acceptable salt thereof, for the therapeutic treatment of a mammal, such as human, said ingredient is normally formulated in accordance with standard pharmaceutical practice as a pharmaceutical composition. Therefore in another aspect the present invention provides a pharmaceutical composition which comprises a compound of the formula (I), or a pharmaceutically acceptable salt thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), inhalation, oral, rectal or parenteral administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient.

Each patient may receive, for example, a dose of 0.0001 $mgkg^{-1}$ to 10 $mgkg^{-1}$, for example in the range of 0.005 $mgkg^{-1}$ to 5 $mgkg^{-1}$, of the active ingredient administered, for example, 1 to 4 times per day.

In an embodiment of the invention, there is provided a pharmaceutical composition comprising a compound of formula (I) in association with a pharmaceutically acceptable adjuvant, diluent or carrier, which is formulated for inhaled administration (including oral and nasal inhalation).

The compound of formula (I) may be administered using a suitable delivery device, for example from a dry powder inhaler, a metered dose inhaler, a nebuliser or a nasal delivery device. Such devices are well known.

Dry powder inhalers may be used to administer the compound of formula (I), alone or in combination with a pharmaceutically acceptable carrier, in the later case either as a finely divided powder or as an ordered mixture. The dry powder inhaler may be single dose or multi-dose and may utilise a dry powder or a powder-containing capsule.

Accordingly in one embodiment, the compound of formula (I), or a pharmaceutical composition containing a compound of formula (I), is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multidose (reservoir) inhalers. In single-dose devices, individual doses are provided, usually in gelatine capsules, and have to be loaded into the inhaler before use, examples of which include Spinhaler® (Aventis), Rotahaler® (GlaxoSmithKline), Aeroliser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline), Nexthaler® (Chiesi) and Aerohaler® (Boehringer) devices. In multidose devices, drug is stored in a bulk powder reservoir from which individual doses are metered, examples of which include Genuair® (AstraZeneca), Turbuhaler® (AstraZeneca), Easyhaler® (Orion), Novolizer® (ASTA Medica), Clickhaler® (Innovata Biomed), Spiromax® (Teva) and Pulvinal® (Chiesi) devices.

An inhalable pharmaceutical composition for use in a DPI can be prepared by mixing finely divided active ingredient (having an aerodynamic diameter generally equal to or less than 10 µm, such as equal to or less than 5 µm, e.g. from 1 to 5 µm) with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Suitably the particles of the active ingredient adhere to the carrier particles to form an ordered (interactive) powder mixture. The carrier particles may have a mass median diameter of from 20 to 1000 µm, more usually from 50 to 500 µm.

Alternatively, an inhalable pharmaceutical composition may be prepared by processing a finely divided powder (e.g. consisting of finely divided active ingredient and finely divided carrier particles) into spheres that break up during the inhalation procedure.

The powder mixture may then, as required, be dispensed into hard gelatine capsules, each containing the desired dose of the active ingredient. Alternatively the powder mixture may be loaded into the reservoir of a multidose inhaler for example, the Genuair®, or the Turbuhaler®.

In a further embodiment, the compound of formula (I) is administered by means of a metered dose inhaler, particularly a pressurised metered dose inhaler (pMDI). The pMDI contains the active as a suitable solution or suspension in a pressurised container. The active is delivered by actuating a valve on the pMDI device. Actuation may be manual or breath actuated. In manually actuated pMDIs the device is actuated by the user as they inhale, for example by pressing a suitable release mechanism on the pMDI device. Breath actuated pMDIs are actuated when the patient inhales through the mouthpiece of the pMDI. This can be advantageous as the actuation of the device is timed with the patients' inhalation and can result in a more consistent dosing of the active. Examples of pMDI devices include for example Rapihaler® (AstraZeneca).

An inhalable pharmaceutical composition for use in a pMDI can be prepared by dissolving or dispersing the compound of formula (I) in a suitable propellant and with or without additional excipients such as solvents (for example ethanol), surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients.

In a further embodiment, the compound of formula (I) is administered by means of a metered dose inhaler in combination with a spacer. Suitable spacers are well known and include Nebuchamber® (AstraZeneca) or Volumatic® (GlaxoSmithKline).

In a further embodiment, the compound of formula (I) is administered by means of a nebuliser. Suitable nebulisers are well known and include eFlow® (PARI GmbH).

An inhalable pharmaceutical composition for use in a nebuliser can be prepared by dispersing or preferably dissolving the compound of formula (I) in a suitable aqueous medium. The composition may also include for example suitable pH and/or tonicity adjustment, surfactants and preservatives. For example a suitable composition for inhalation from a nebuliser comprises a compound of formula (I) dispersed in an aqueous medium (mg/g in Mill-Q water) comprising sodium chloride (9 mg/g); citric acid dried (0.0735 mg/g); sodium citrate (0.19 mg/g); benzalkonium chloride (0.1 mg/g), EDTA (ethylenediamine tetraacetic acid, 0.1 mg/g) and Polysorbate 80 (0.3 mg/g).

In a further embodiment, the compound of formula (I) is administered nasally as a spray from a suitable nasal delivery device, for example a spray pump or an MDI. Alternatively, the compound could be administered nasally as a powder using a suitable DPI device e.g. Rhinocort®, Turbuhaler® (AstraZeneca).

An inhalable pharmaceutical composition for use in a spray pump or MDI nasal delivery device can be prepared by dispersing or preferably dissolving the compound of formula (I) in a suitable aqueous medium. The composition may also include for example suitable pH and/or tonicity adjustment, surfactants, preservatives, lubricants flavourings or viscosity modifiers. If required additives to enhance absorption from the nasal cavity can be included, such as a suitable bioadhesive polymer. Suitable dry powder compositions for nasal delivery are as hereinbefore described in relation to DPI delivery. However, where it is desirable to limit the penetration of the compound into the lung and keep the compound in the nasal cavity, it may be necessary to use the compound as larger particle sizes, for example with an average particle diameter greater than about 10 µm, e.g. from 10 µm to 50 µm.

Accordingly, the present invention also provides an inhaler device (for example a dry powder inhaler, in particular a multiple unit dose dry powder inhaler, or a pMDI inhaler) containing an inhalable pharmaceutical composition of the invention.

The invention further relates to a combination therapy wherein a compound of the invention, or a pharmaceutically acceptable salt thereof, and a second active ingredient are administered concurrently, sequentially or in admixture, for the treatment of one or more of the conditions listed above. Such a combination may be used in combination with one or more further active ingredients.

In a further aspect of the present invention there is provided a pharmaceutical composition (for example, for use as a medicament for the treatment of one of the diseases or conditions listed herein, such as CF or COPD) comprising a compound of the invention, or a pharmaceutically acceptable salt thereof, and at least one additional active ingredient selected from:
  a) a beta-adrenoceptor agonist;
  b) a muscarinic receptor antagonist;
  c) a joint muscarinic receptor antagonist and beta-adrenoceptor agonist; d) a toll-like receptor agonist (such as a TLR7 or TLR9 agonist)
  e) an adenosine antagonist;
  f) a glucocorticoid receptor agonist (steroidal or non-steroidal);
  g) a p38 antagonist;
  h) an IKK2 antagonist;
  i) a PDE4 antagonist;
  j) a modulator of chemokine receptor function (such as a CCR1, CCR2B, CCR5, CXCR2 or CXCR3 receptor antagonist);
  k) a CRTh2 antagonist; or
  l) an osmolyte, for example an ionic osmolyte, such as hypertonic saline as defined below.

The present invention still further relates to the combination of a compound of the invention, or a pharmaceutically acceptable salt thereof, together with a beta-adrenoceptor agonist (including beta receptor subtypes 1-4) such as terbutaline (e.g. as the sulphate salt), salmeterol (e.g. as the xinafoate salt), salbutamol (albuterol) (e.g. as the sulphate salt), procaterol (e.g. as the hydrochloride salt), pirbuterol (e.g. as the acetate salt), orciprenaline (metaproterenol) (e.g. as the sulphate salt), milveterol (e.g. as the hydrochloride salt), levosalbutamol (levalbuterol) (e.g. as the hydrochloride salt), abediterol, isoprenaline (isoproterenol) (e.g. as the hydrochloride salt), indacaterol (e.g. as the maleate salt), vilanterol (e.g. as the trifenatate (triphenylacetic acid) salt), formoterol (e.g. as the fumarate salt, for example the fumarate dihydrate salt), carmoterol, bitolterol (e.g. as the mesylate salt), olodaterol, bedoradrine (e.g. as the sulphate salt), bambuterol (e.g. as the hydrochloride salt), arformoterol (e.g. as the tartrate salt), PF-610355 (2-[3-[2-[[(2R)-2-hydroxy-2-[4-hydroxy-3-(methanesulfonamido)phenyl]ethyl]amino]-2-methyl-propyl]phenyl]-N-[[3-(4-hydroxyphenyl)phenyl]methyl]acetamide), N-(2-diethylaminoethyl)-N-[2-[2-(4-hydroxy-2-oxo-3H-1,3-benzothiazol-7-yl)ethylamino]ethyl]-3-[2-(1-naphthyl)ethoxy]propanamide, N-cyclohexyl-3-[2-(3-fluorophenyl)ethylamino]-N-[2-[2-(4-hydroxy-2-oxo-3H-1,3-benzothiazol-7-yl)ethylamino]ethyl]propanamide, or N-cyclohexyl-N-[2-[2-(5-hydroxy-3-oxo-4H-1,4-benzoxazin-8-yl)ethylamino]ethyl]-3-[2-[3-(1-methylpyrazol-4-yl)phenyl]ethoxy]propanamide.

The present invention still further relates to the combination of a compound of the invention, or a pharmaceutically acceptable salt thereof, together with a muscarinic receptor antagonist (for example a M1, M2 or M3 antagonist, such as a selective M3 antagonist) such as tiotropium (e.g. as the bromide salt), oxitropium (e.g. as the bromide salt), ipratropium (e.g. as the bromide salt), glycopyrronium bromide (e.g. as a racemic mixture of stereoisomers, or as the R,R-, R,S-, S,R-, or S,S-stereoisomer, or as a mixture comprising two or more of the R,R-, R,S-, S,R-, or S,S-stereoisomers), aclidinium (e.g. as the bromide salt), GSK573719 (3-[2-[3-(5-cyclohexyloxycarbonyl-thiophen-2-yl)-ureido]-3-(4-hydroxy-phenyl)-propionylamino]-1-(3-hydroxy-benzyl)-1-methyl-piperidinium), BEA2180BR (hydroxy-di-thiophen-2-yl-acetic acid 8-methyl-8-aza-bicyclo[3.2.1]oct-6-en-3-yl ester) (e.g. as the hydrobromide salt), [(3R)-1-[2-oxo-2-(2-pyridylamino)ethyl]quinuclidin-1-ium-3-yl]1-phenylcycloheptanecarboxylate (e.g. as the bromide salt), or 2-[(4-chlorophenyl)methoxy]ethyl-[[2-[(R)-cyclohexyl-hydroxy-phenyl-methyl]oxazol-5-yl]methyl]-dimethyl-ammonium (e.g. as the napadisylate salt).

The present invention still further relates to the combination of a compound of the invention, or a pharmaceutically acceptable salt thereof, together with an agent which is a joint muscarinic receptor antagonist (for example a M1, M2 or M3 antagonist, such as a selective M3 antagonist) and a beta-adrenoceptor agonist such as PF4348235 ([1-[9-[[(2R)-2-hydroxy-2-[4-hydroxy-3-(methanesulfonamido)phenyl]ethyl]amino]nonyl]-4-piperidyl]N-[2-(3-chloro-4-hydroxy-phenyl)phenyl]carbamate), 3-[2-[2-chloro-3-[[8-(2-ethylthiazole-4-carbonyl)-11-oxa-3,8-diazaspiro[5.5]undecan-3-yl]methyl]phenyl]ethoxy]-N-cyclopentyl-N-[2-[2-(5-hydroxy-3-oxo-4H-1,4-benzoxazin-8-yl)ethylamino]ethyl]propanamide, N-butyl-N-[2-[2-(5-hydroxy-3-oxo-4H-1,4-benzoxazin-8-yl)ethylamino]ethyl]-3-[2-[3-[2-[8-(2-isopropylthiazole-4-carbonyl)-11-oxa-3,8-diazaspiro[5.5]undecan-3-yl]ethyl]phenyl]ethoxy]propanamide, or 7-[(1R)-2-[2-[2-fluoro-5-[[8-(2-isopropylthiazole-4-carbonyl)-11-oxa-3,8-diazaspiro[5.5]undecan-3-yl]methyl]phenyl]ethylamino]-1-hydroxyethyl]-4-hydroxy-3H-1,3-benzothiazol-2-one.

The present invention still further relates to the combination of a compound of the invention, or a pharmaceutically acceptable salt thereof, together with a toll-like receptor agonist (including an agonist of TLR7 or TLR9) such as loxoribine (7-allyl-2-amino-9-[(2R,3R,4S,5R)-3,4-dihydroxy-5-(hydroxymethyl)tetrahydrofuran-2-yl]-1H-purine-6,8-dione), methyl 2-[3-[[3-(6-amino-2-butoxy-8-oxo-7H-purin-9-yl)propyl-(3-morpholinopropyl)amino]methyl]phenyl]acetate (e.g. as the hydrobromide, hydrochloride or dimaleate salt), 4-(dimethylamino)butyl 2-[4-[[2-amino-4-methyl-6-(pentylamino)pyrimidin-5-yl]methyl]phenyl]acetate (e.g. as the disaccharin, difumaric acid, di-1-hydroxy-2-naphthoic acid or mono-benzoic acid salt), or 5'-TCG AAC GTT CGA AGA TGA TGA T (SEQ ID NO: 1) (disclosed as SEQ ID 171 in WO2004/0158179).

The present invention still further relates to the combination of a compound of the invention, or a pharmaceutically acceptable salt thereof, together with an adenosine antagonist such as regadenoson, ATL-313 (methyl 4-[3-[6-amino-9-[(2R,3R,4S,5S)-5-(cyclopropylcarbamoyl)-3,4-dihydroxy-tetrahydrofuran-2-yl]purin-2-yl]prop-2-ynyl]piperidine-1-carboxylate), or apadenoson (methyl 4-[3-[6-amino-9-[(2R,3R,4S,5S)-5-(ethylcarbamoyl)-3,4-dihydroxy-tetrahydrofuran-2-yl]purin-2-yl]prop-2-ynyl]cyclohexanecarboxylate).

The present invention still further relates to the combination of a compound of the invention, or a pharmaceutically acceptable salt thereof, together with a glucocorticoid receptor agonist (steroidal or non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate, (1R,3aS,3bS,10aR,10bS,11S,12aS)-1-{[(cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-furoate, (1R,2R,3aS,3bS,10aS,10bR,11S,12aS)-10b-Fluoro-1-{[(fluoromethyl)sulfanyl]carbonyl}-7-(6-fluoro-pyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, 2,2,2-trifluoro-N-[(1S,2R)-2-[1-(4-fluorophenyl)indazol-5-yl]oxy-2-(3-methoxyphenyl)-1-methyl-ethyl]acetamide, 3-[5-[(1R,2S)-1-(4H-1,3-benzodioxin-7-yl)-2-(2,2-difluoropropanoylamino)propoxy]indazol-1-yl]-N-(3-pyridylmethyl)benzamide, 3-[5-[(1R,2S)-2-(2,2-difluoropropanoylamino)-1-(2,3-dihydro-1,4-benzodioxin-6-yl)propoxy]indazol-1-yl]-N-[(3R)-1,1-dioxothiolan-3-yl]benzamide, or 3-[5-[(1R,2S)-2-(2,2-difluoropropanoylamino)-1-(2,3-dihydro-1,4-benzodioxin-6-yl)propoxy]indazol-1-yl]-N-[(3R)-tetrahydrofuran-3-yl]benzamide.

The present invention still further relates to the combination of a compound of the invention, or a pharmaceutically acceptable salt thereof, together with a p38 antagonist such as PH797804 (3-[3-Bromo-4-(2,4-difluoro-benzyloxy)-6-methyl-2-oxo-2H-pyridin-1-yl]-4,N-dimethyl-benzamide), losmapimod, PF03715455 (1-[5-tert-butyl-2-(3-chloro-4-hydroxy-phenyl)pyrazol-3-yl]-3-[[2-[[3-[2-(2-hydroxyethylsulfanyl)phenyl]-[1,2,4]triazolo[4,3-a]pyridin-6-yl]sulfanyl]phenyl]methyl]urea), N-cyclopropyl-4-methyl-3-[6-(4-methylpiperazin-1-yl)-4-oxo-quinazolin-3-yl]benzamide, or N-cyclopropyl-3-fluoro-4-methyl-5-[3-[[1-[2-[2-(methylamino)ethoxy]phenyl]cyclopropyl]amino]-2-oxo-pyrazin-1-yl]benzamide.

The present invention still further relates to the combination of a compound of the invention, or a pharmaceutically acceptable salt thereof, together with a phosphodiesterase (PDE) inhibitor such as a methylxanthanine including theophylline and aminophylline or a selective PDE isoenzyme inhibitor (including a PDE4 inhibitor or an inhibitor of the isoform PDE4D) such as tetomilast, roflumilast, oglemilast, ibudilast, GPD-1116 (3-benzyl-5-phenyl-1H-pyrazolo[4,3-c][1,8]naphthyridin-4-one), ronomilast, NVP ABE 171 (4-[8-(2,1,3-benzoxadiazol-5-yl)-1,7-naphthyridin-6-yl] benzoic acid), RPL554 (2-[(2E)-9,10-dimethoxy-4-oxo-2-(2,4,6-trimethylphenyl)imino-6,7-dihydropyrimido[6,1-a]isoquinolin-3-yl]ethylurea), CHF5480 ([(Z)-2-(3,5-dichloro-4-pyridyl)-1-(3,4-dimethoxyphenyl)vinyl](2S)-2-(4-isobutylphenyl)propanoate), or GSK256066 (6-[3-(dimethylcarbamoyl)phenyl]sulfonyl-4-(3-methoxyanilino)-8-methyl-quinoline-3-carboxamide).

The present invention still further relates to the combination of a compound of the invention, or a pharmaceutically acceptable salt thereof, together with an IKK2 antagonist such as 5-(2-isopropylisoindolin-5-yl)-3-[1-(2-methoxyethylsulfonyl)-4-piperidyl]-1H-indole-7-carboxylic acid.

The present invention still further relates to the combination of a compound of the invention, or a pharmaceutically acceptable salt thereof, together with a modulator of chemokine receptor function such as an antagonist of CCR1, CCR2, CCR2A, CCR2B, CCR3, CCR4, CCR5, CCR6, CCR7, CCR8, CCR9, CCR10 or CCR11 (for the C—C family), for example a CCR1, CCR2B or CCR5 receptor antagonist; CXCR1, CXCR2, CXCR3, CXCR4 or CXCR5 (for the C—X—C family), for example a CXCR2 or CXCR3 receptor antagonist; or CX$_3$CR1 for the C—X$_3$—C family. For example, the present invention relates to the combination of a compound of the invention with PS-031291 (pyrrolidine-1,2-dicarboxylic acid 2-[(4-chlorobenzyl)-methyl-amide] 1-[(4-trifluoromethyl-phenyl)-amide]), CCX-354 (1-[4-(4-chloro-3-methoxy-phenyl)piperazin-1-yl]-2-[3-(1H-imidazol-2-yl)pyrazolo[3,4-b]pyridin-1-yl]ethanone), vicriviroc, maraviroc, cenicriviroc, navarixin (2-hydroxy-N,N-dimethyl-3-[[2-[[(1R)-1-(5-methyl-2-furyl)propyl]amino]-3,4-dioxo-cyclobuten-1-yl]amino]benzamide), SB656933 (1-(2-chloro-3-fluoro-phenyl)-3-(4-chloro-2-hydroxy-3-piperazin-1-ylsulfonyl-phenyl)urea), N-[1-[(3R)-3-(3,5-difluorophenyl)-3-(1-methylsulfonyl-4-piperidyl)propyl]-4-piperidyl]-N-ethyl-2-(4-methylsulfonylphenyl)acetamide, N-[2-[(2S)-3-[[1-[(4-chlorophenyl)methyl]-4-piperidyl]amino]-2-hydroxy-2-methyl-propoxy]-4-hydroxy-phenyl]acetamide, 2-[2-chloro-5-[(2S)-3-(5-chlorospiro[3H-benzofuran-2,4'-piperidine]-1'-yl)-2-hydroxy-propoxy]-4-(methylcarbamoyl)phenoxy]-2-methyl-propanoic acid, N-[2-[(2,3-difluorophenyl)methylsulfanyl]-6-[(1R,2S)-2,3-dihydroxy-1-methyl-propoxy]pyrimidin-4-yl]azetidine-1-sulfonamide, or N-[2-[(2,3-difluorophenyl)methylsulfanyl]-6-[[(1R,2R)-2,3-dihydroxy-1-methyl-propyl]amino]pyrimidin-4-yl]azetidine-1-sulfonamide.

The present invention still further relates to the combination of a compound of the invention, or a pharmaceutically acceptable salt thereof, together with a leukotriene biosynthesis inhibitor, 5-lipoxygenase (5-LO) inhibitor or 5-lipoxygenase activating protein (FLAP) antagonist such as TA270 (4-hydroxy-1-methyl-3-octyloxy-7-sinapinoylamino-2(1H)-quinolinone), PF-4191834 (2H-pyran-4-carboxamide, tetrahydro-4-[3-[[4-(1-methyl-1H-pyrazol-5-yl)phenyl]thio]phenyl]-), setileuton, CMI977 (1-[4-[(2S,5S)-5-[(4-fluorophenoxy)methyl]tetrahydrofuran-2-yl]but-3-ynyl]-1-hydroxy-urea), fiboflapon (3-[3-tert-butylsulfanyl-1-[[4-(6-ethoxy-3-pyridyl)phenyl]methyl]-5-[(5-methyl-2-pyridyl)methoxy]indol-2-yl]-2,2-dimethyl-propanoic acid), GSK2190915 (1H-indole-2-propanoic acid, 3-[(1,1-dimethylethyl)thio]-1-[[4-(6-methoxy-3-pyridinyl)phenyl]methyl]-α,α-dimethyl-5-[(2-pyridinyl)methoxy]-), licofelone, quiflapon (3-[3-tert-butylsulfanyl-1-[(4-chlorophenyl)methyl]-5-(2-quinolylmethoxy)indol-2-yl]-2,2-dimethyl-propanoic acid), veliflapon ((2R)-2-cyclopentyl-2-[4-(2-quinolylmethoxy)phenyl]acetic acid), ABT080 (4,4-bis[4-(2-quinolylmethoxy)phenyl]pentanoic acid), zileuton, zafirlukast, or montelukast.

The present invention still further relates to the combination of a compound of the invention, or a pharmaceutically acceptable salt thereof, together with a CRTh2 antagonist or a DP2 antagonist such as ACT129968 (2-[2-[(5-acetyl-2-methoxy-phenyl)methylsulfanyl]-5-fluoro-benzimidazol-1-yl]acetic acid), AMG853 (2-[4-[4-(tert-butylcarbamoyl)-2-[(2-chloro-4-cyclopropyl-phenyl)sulfonylamino]phenoxy]-5-chloro-2-fluoro-phenyl]acetic acid), AM211 (2-[3-[2-[[benzylcarbamoyl(ethyl)amino]methyl]-4-(trifluoromethyl)phenyl]-4-methoxy-phenyl]acetic acid), 2-[4-acetamido-3-(4-chlorophenyl)sulfanyl-2-methyl-indol-1-yl]acetic acid, (2S)-2-[4-chloro-2-(2-chloro-4-ethylsulfonyl-phenoxy)phenoxy]propanoic acid, 2-[4-chloro-2-[2-fluoro-4-(4-fluorophenyl)sulfonyl-phenyl]phenoxy]acetic acid, or (2S)-2-[2-[3-chloro-4-(2,2-dimethylpyrrolidine-1-carbonyl)phenyl]-4-fluorophenoxy]propanoic acid.

The present invention still further relates to the combination of a compound of the invention, or a pharmaceutically acceptable salt thereof, together with an MK2 (MAP-KAP kinase 2) antagonist such as varesplabid, PF-3644022 ((10R)-10-methyl-3-(6-methylpyridin-3-yl)-9,10,11,12-tetrahydro-8H-[1,4]diazepino[5',6':4,5]thieno[3,2-f]quinolin-8-one), or 4-benzoyl-D-phenylalanyl-D-seryl-D-tryptophyl-D-seryl-2,3,4,5,6-pentafluoro-D-phenylalanyl-3-cyclohexyl-D-alanyl-D-arginyl-D-arginyl-D-arginyl-D-glutaminyl-D-arginyl-D-arginine.

The present invention still further relates to the combination of a compound of the invention, or a pharmaceutically acceptable salt thereof, together with a myeloperoxidase antagonist such as resveratrol, piceatannol, 3-[[(2R)-tetrahydrofuran-2-yl]methyl]-2-thioxo-7H-purin-6-one, or 1-(2-isopropoxyethyl)-2-thioxo-5H-pyrrolo[3,2-d]pyrimidin-4-one.

The present invention still further relates to the combination of a compound of the invention, or a pharmaceutically acceptable salt thereof, together with an osmolyte. As used herein, an "osmolyte" is an osmotically-active small molecule and is intended to cover both ionic and non-ionic osmolytes. In a further aspect of the invention there is provided a combination of a compound of the invention, or a pharmaceutically acceptable salt thereof, together with an ionic osmolyte, such as hypertonic saline.

In a still further aspect of the present invention there is provided a pharmaceutical composition (for example, for use as a medicament for the treatment of one of the diseases or conditions listed herein, such as CF or COPD) comprising a compound of the invention, or a pharmaceutically acceptable salt thereof, and at least one additional active ingredient selected from:

a) a beta-adrenoceptor agonist;
b) a muscarinic receptor antagonist;
c) a joint muscarinic receptor antagonist and beta-adrenoceptor agonist; or
d) a glucocorticoid receptor agonist (steroidal or non-steroidal); or
e) an osmolyte, for example an ionic osmolyte, such as hypertonic saline.

as defined above.

In a still further aspect of the invention, the at least one additional active ingredient is a beta-adrenoceptor agonist.

In another aspect, the at least one additional active ingredient is a muscarinic receptor antagonist. In a further aspect, the at least one additional active ingredient is a glucocorticoid receptor agonist (steroidal or non-steroidal). In a still further aspect, the at least one additional active ingredient is a joint muscarinic receptor antagonist and beta-adrenoceptor agonist. In a still further aspect, the at least one additional active ingredient is an osmolyte.

The compounds described in this specification are further illustrated in the following Examples. These Examples are given by way of illustration only and are non-limiting.

Abbreviations aq Aqueous
(BOC)$_2$O/Boc Di-tertbutyl dicarbonate
CV Column Volume
DEA Diethylamine
DEAD Diethylazadicarboxylate
DIPA Diisopropylamine
DIEA/DIPEA Diisopropylethylamine
ESI Electrospray Ionization
FA Formic Acid
FMOC/Fmoc Fluorenylmethyloxycarbonyl
HATU 1-[Bis(dimethylamino)methylene]-1H-1,2,3-triazolo[4,5-b]pyridinium 3-oxid hexafluorophosphate
HBSS Hanks' Balanced Salt Solution
HBTU 2-(1H-Benzotriazole-1-yl)-1,1,3,3-tetramethyluronium hexafluorophosphate
HEPES 2-[4-(2-hydroxyethyl)piperazin-1-yl]ethanesulfonic acid
HPLC High Performance Liquid Chromatography
IPA Isopropylamine
LC/MS Liquid Chromatography-Mass Spectroscopy
MeTHF Methyl-tetrahydrofuran
MTBE tert-Butyl methyl ether
NMP N-methylpyrrolidinone
Rt Retention time
sat. Saturated
SFC Supercritical fluid chromatography
TBME tert-Butyl methyl ether
TEA Triethylamine
THF Tetrahydrofuran
wt-% weight-%
General Methods NMR spectra were recorded on a Bruker Avance, Avance II or Avance III spectrometer at a proton frequency of 400, 500 or 600 MHz. A JEOL EX-270 spectrometer was used if a proton frequency of 270 MHz is reported. The central peaks of chloroform-δ (H 7.26 ppm), acetone (H 2.04 ppm), dichloromethane-d$_2$ (H 5.32 ppm), CH$_3$OD (H 3.30 ppm) or DMSO-d$_6$ (H 2.49 ppm) were used as internal references. Slight variations of chemical shifts may occur, as is well known in the art, as a result in variations in sample preparation, such as analyte concentration variations and including or omitting additives (for example NMR assay standards or trifluoroacetic acid).

LC/MS experiments were performed using a Waters Acquity UPLC system combined with a Waters Xevo Q-ToF Mass Spectrometer in ESI mode. LC was run in two set ups: 1) BEH C18 column (1.7 am 2.1×50 mm) in combination with a gradient (2-95% B in 5 min) of aquous 46 mM ammonium carbonate/ammonia buffer at pH 10 (A) and MeCN (B) at a flow rate of 1.0 mL/min. 2) HSS C18 column (1.8 am 2.1×50 mm) with a gradient (2-95% B in 5 min) of aqueous 10 mM FA/1 mM ammonium formate buffer at pH 3 (A) and MeCN (B) at a flow rate of 1.0 ml/min.

Optical purity, indicated as enantiomeric excess (% ee), was determined by chiral HPLC using an Agilent 1100 series chromatograph. Method A: System equipped with Chiralpak IC 250×4.6 mm; 5 m. As mobile phase heptane/iPrOH/ethanolamine (60:40:0.1) with a flow rate of 1 mL/min was used. The injection volume was 10 μL and compound detection was performed by UV at 268 nm. Method B: System quipped with Chiralpak IC 150×4.6 mm, 3 μm. As mobil phase $CO_2$, 120 bar (A) and MeOH (0.5% DEA) (B) was used in a ratio A/B of 80/20 with a flow rate of 4 mL/min. The injection volume was 5 μL.

Preparative HPLC was performed with a Waters FractionLynx system with intergrated MS detection and equipped with Prep C18 OBD 5 μm 19×150 mm columns from X-Bridge or Sunfire. Alternatively Gilson GX-281 with intergrated UV detection was used, equipped with either Kromasil C8 10 μm, 20×250 ID or 50×250 ID mm. As eluent gradients of water/MeCN/AcOH (95/5/0.1) or water/0.05% TFA or water/0.1% NH$_4$HCO$_3$ (A) and MeCN (B) were applied.

Preparative SCF was performed with a Waters Prep100 SCF system with intergrated MS detection, equipped with Waters Viridis 2-EP or Phenomenex Luna Hilic, 30×250 mm, 5 μm. As eluent gradients of $CO_2$ (100 g/min, 120 bar, 40° C.) (A) and MeOH/NH$_3$ (20 mM) or MeOH (5% FA) or MeOH (B) were applied.

Unless stated otherwise, starting materials were commercially available or previously described in the literature. All solvents and commercial reagents were of laboratory grade and were used as received unless otherwise stated.

Chemical names as described in the Examples below were generated using the ChemDraw (Ultra 11) naming package. The skilled person will be aware that different naming packages may produce different chemical names for the same compound. By way of illustration only, the chemical names generated for Examples 1 to 16 below using the ACD/Name 2012 naming package are respectively:

3,5-diamino-6-chloro-N-[(2R)-2-(2-methylbenzyl)-3-({[1-(3-{[(2S,3R,4R)-2,3,4,5-tetrahydroxypentyl]amino}propanoyl)piperidin-4-yl]methyl}amino)propyl]pyrazine-2-carboxamide;

1-deoxy-1-[(2-{[4-({[(2R)-3-{[(3,5-diamino-6-chloropyrazin-2-yl)carbonyl]amino}-2-(2-methylbenzyl)propyl]amino}methyl)benzoyl]amino}ethyl)(hexyl)amino]-D-xylitol;

1-deoxy-1-{[2-({[4-({[(2R)-3-{[(3,5-diamino-6-chloropyrazin-2-yl)carbonyl]amino}-2-(2-methylbenzyl)propyl]amino}methyl)piperidin-1-yl]carbonyl}amino)ethyl](hexyl)amino}-D-glucitol;

3,5-diamino-6-chloro-N-[(2R)-3-({[1-(3-{hexyl[(2S,3R,4R,5R)-2,3,4,5,6-pentahydroxyhexyl]amino}propanoyl)piperidin-4-yl]methyl}amino)-2-(2-methylbenzyl)propyl]pyrazine-2-carboxamide;

3,5-diamino-6-chloro-N-[(2R)-3-({[1-(3-{hexyl[(2S,3R,4R)-2,3,4,5-tetrahydroxypentyl]amino}propanoyl)piperidin-4-yl]methyl}amino)-2-(2-methylbenzyl)propyl]pyrazine-2-carboxamide;

1-deoxy-1-[{4-[4-({[(2R)-3-{[(3,5-diamino-6-chloropyrazin-2-yl)carbonyl]amino}-2-(2-methylbenzyl)propyl]amino}methyl)piperidin-1-yl]-4-oxobutyl}(hexyl)amino]-D-glucitol;

3,5-diamino-6-chloro-N-[(2R)-2-(2-methylbenzyl)-3-({[1-(3-{[(2S,3R,4R,5R)-2,3,4,5,6-pentahydroxyhexyl]amino}propanoyl)piperidin-4-yl]methyl}amino)propyl]pyrazine-2-carboxamide;

3,5-diamino-6-chloro-N-[(2R)-3-({[1-(3-{hexyl[(2R,3R,4R,5R)-2,3,4,5,6-pentahydroxyhexyl]amino}propanoyl)piperidin-4-yl]methyl}amino)-2-(2-methylbenzyl)propyl]pyrazine-2-carboxamide;

1-deoxy-1-[(2-{[4-({[(2R)-3-{[(3,5-diamino-6-chloropyrazin-2-yl)carbonyl]amino}-2-(2-methylbenzyl)propyl]amino}methyl)benzoyl]amino}ethyl)(hexyl)amino]-D-mannitol;

1-deoxy-1-[(2-{[4-({[(2R)-3-{[(3,5-diamino-6-chloropyrazin-2-yl)carbonyl]amino}-2-(2-methylbenzyl)propyl]amino}methyl)benzoyl]amino}ethyl)(hexyl)amino]-D-glucitol;

1-deoxy-1-{[2-({[4-({[(2R)-3-{[(3,5-diamino-6-chloropyrazin-2-yl)carbonyl]amino}-2-(2-methylbenzyl)propyl]amino}methyl)phenoxy]carbonyl}amino)ethyl](hexyl)amino}-D-glucitol;

1-deoxy-1-[(2-{[4-(2-{[(2R)-3-{[(3,5-diamino-6-chloropyrazin-2-yl)carbonyl]amino}-2-(2-methylbenzyl)propyl]amino}ethyl)benzoyl]amino}ethyl)(hexyl)amino]-D-glucitol;

1-deoxy-1-[(2-{[4-(2-{[(2R)-3-{[(3,5-diamino-6-chloropyrazin-2-yl)carbonyl]amino}-2-(2-methylbenzyl)propyl]amino}ethyl)benzoyl]amino}ethyl)(hexyl)amino]-D-xylitol;

1-deoxy-1-[(2-{[4-({[(2S)-3-{[(3,5-diamino-6-chloropyrazin-2-yl)carbonyl]amino}-2-(2-methylbenzyl)propyl]amino}methyl)benzoyl]amino}ethyl)(hexyl)amino]-D-xylitol;

5-deoxy-5-[(2-{[4-({[(2S)-3-{[(3,5-diamino-6-chloropyrazin-2-yl)carbonyl]amino}-2-(2-methylbenzyl)propyl]amino}methyl)benzoyl]amino}ethyl)(hexyl)amino]-D-xylitol;

1-deoxy-1-[(2-{[3-(2-{[(2R)-3-{[(3,5-diamino-6-chloropyrazin-2-yl)carbonyl]amino}-2-(2-methylbenzyl)propyl]amino}ethyl)benzoyl]amino}ethyl)(hexyl)amino]-D-glucitol.

EXAMPLE 1

3,5-diamino-6-chloro-N—((R)-2-(2-methylbenzyl)-3-(((1-(3-(((2S,3R,4R)-2,3,4,5-tetrahydroxypentyl)amino)propanoyl)piperidin-4-yl)methyl)amino)propyl)pyrazine-2-carboxamide

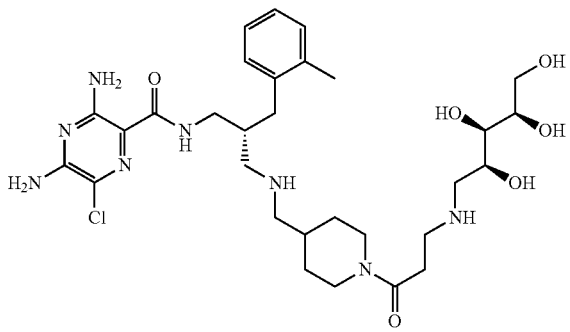 [SMILES: Cc1ccccc1C[C@H](CNCC1CCN(C(=O)CCNC[C@H](O)[C@@H](O)[C@H](O)CO)CC1)CNC(=O)c1nc(Cl)c(N)nc1N]

Step 1

(R)-(9H-fluoren-9-yl)methyl (3-(4-(((3-(3,5-diamino-6-chloropyrazine-2-carboxamido)-2-(2-methylbenzyl)propyl)amino)methyl)piperidin-1-yl-3-oxopropyl)carbamate

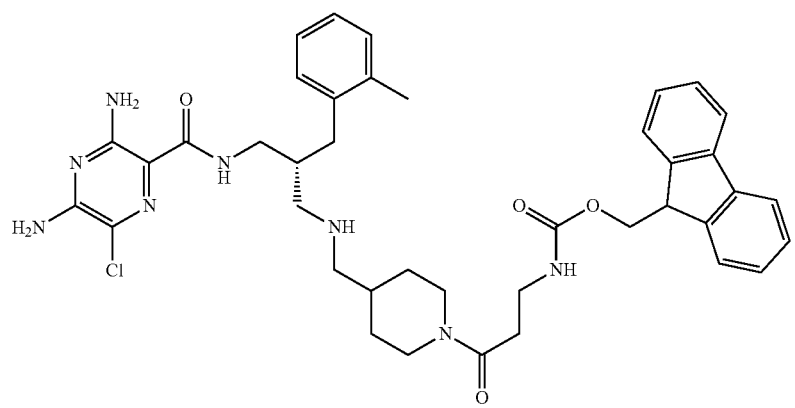 [SMILES: Cc1ccccc1C[C@H](CNCC1CCN(C(=O)CCNC(=O)OCC2c3ccccc3-c3ccccc32)CC1)CNC(=O)c1nc(Cl)c(N)nc1N]

A mixture of (R)-3,5-diamino-N-(3-amino-2-(2-methylbenzyl)propyl)-6-chloropyrazine-2-carboxamide (318 mg, 0.91 mmol) (Intermediate A), (9H-fluoren-9-yl)methyl 3-(4-formylpiperidin-1-yl)-3-oxopropylcarbamate (440 mg, 1.08 mmol) (Intermediate F) and acetic acid (80 µL, 1.40 mmol) in dry THF (6 mL) was stirred at ambient temperature for 30 min. Sodium triacetoxyborohydride (340 mg, 1.60 mmol) was added and the reaction mixture was stirred at 40° C. for additional 1.5 h. Water was added and the mixture stirred for 5 min and the solvents were evaporated off. The residual material was partitioned between EtOAc and water. To the aqueous phase was added 10% $NaHCO_3$ (aq.) until reaching pH 8-9. The phases were separated and the aqueous phase was backextracted with EtOAc. The combined yellow organic phases were dried over $MgSO_4$, filtered and the solvents were evaporated off. The crude product was purified by preparative HPLC (Kromasil C8; $H_2O$/MeCN/AcOH 95/5/0.2). Relevant fractions were combined and concentrated in vacuo. 10% $NaHCO_3$ (aq.) was added and the water phase was extracted with EtOAc. The organic phase was dried over $MgSO_4$, filtered and evaporated. The residual sticky oil was dissolved in DCM/Heptane to give after evaporation the title compound as a solid, 196 mg (29%, purity 87%).

LC/MS: m/z 739 [M+H]$^+$

Step 2

(R)-3,5-diamino-N-(3-(((1-(3-aminopropanoyl)piperidin-4-yl)methyl)amino)-2-(2-methylbenzyl)propyl)-6-chloropyrazine-2-carboxamide

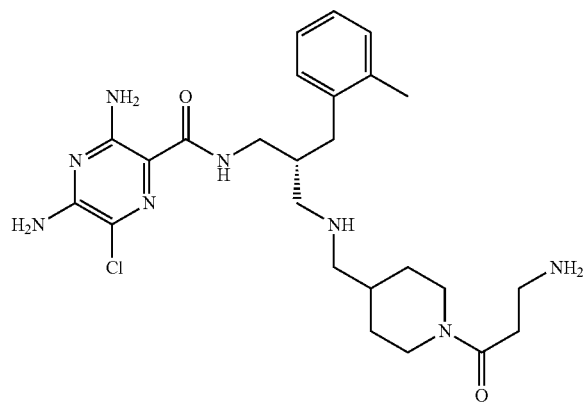 [SMILES: Cc1ccccc1C[C@H](CNCC1CCN(C(=O)CCN)CC1)CNC(=O)c1nc(Cl)c(N)nc1N]

(R)-(9H-fluoren-9-yl)methyl 3-(4-((3-(3,5-diamino-6-chloropyrazine-2-carboxamido)-2-(2-methylbenzyl)propylamino)methyl)piperidin-1-yl)-3-oxopropylcarbamate (196 mg, 0.27 mmol) (from step 1) was dissolved in DCM (5 mL) and treated with piperidine (0.5 mL). The solution was stirred at ambient temperature for 3 h then evaporated to leave a yellow solid.

The crude material was dissolved in THF (5 mL) and DIPEA (280 µL, 1.60 mmol) and treated with (BOC)$_2$O (0.141 mL, 0.61 mmol) in THF (1 mL). The mixture was stirred at ambient temperature. After 3 h LC/MS showed only a small conversion to mono-Boc protected product, majority was still unreacted amine. A large excess of DIPEA and BOC$_2$(O) were added and the mixture was stirred for 1 h at ambient temperature. MeCN (2-3 ml) was added to increase solubility and the mixture was heated at 50° C. for 2 h then ambient temperature over the weekend.

The volatiles were evaporated in vacuo and the residue partitioned between EtOAc and water. The water phase was made acidic by addition of 0.5 M citric acid. Brine was added to help separation of the phases. The organic phase was washed with water and brine.

Solvent was evaporated off and the residue was dissolved in DCM and purified by flash chromatography (EtOAc/heptane, gradient 30-100% EtOAc). The solvents were evaporated to afford the di-BOC protected titel compound (96 mg).

The obtained di-BOC-protected material (96 mg) was dissolved in DCM (2 mL) and treated with TFA (0.5 mL), the solution was stirred at ambient temperature for 2.5 hours. The mixture was evaporated, residue dissolved in water and purified by preparative HPLC (Kromasil C8; $H_2O$/MeCN/HCO$_2$H 95/5/0.2 to 60/40/0.2 over 16 min). Freeze drying afforded the title compound as a solid (64 mg, 45%)

LC/MS: m/z 517 [M+H]$^+$ $^1$H NMR (500 MHz, MeOD) δ 1.13-1.34 (m, 2H), 1.83-2.06 (m, 3H), 2.29-2.39 (m, 1H), 2.35 (s, 3H), 2.59-2.93 (m, 9H), 3.08-3.23 (m, 3H), 3.32-3.37 (m, 1H), 3.67-3.74 (m, 1H), 3.87-3.96 (m, 1H), 4.52-4.6 (m, 1H), 7.11-7.22 (m, 4H), 8.51 (s, 0.4H, formic acid residue).

Step 3

3,5-diamino-6-chloro-N—((R)-2-(2-methylbenzyl)-3-(((1-(3-(((2S,3R,4R)-2,3,4,5-tetrahydroxypentyl)amino)propanoyl)piperidin-4-yl)methyl)amino)propyl)pyrazine-2-carboxamide

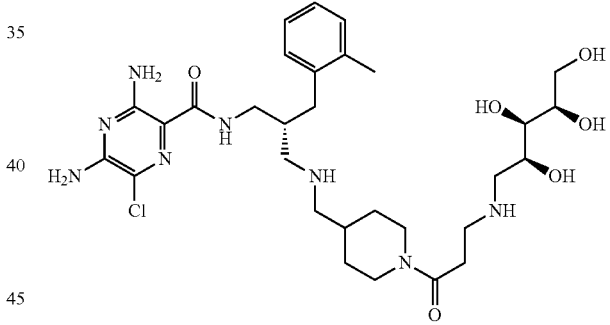

(R)-3,5-diamino-N-(3-(((1-(3-aminopropanoyl)piperidin-4-yl)methyl)amino)-2-(2-methylbenzyl)propyl)-6-chloropyrazine-2-carboxamide (900 mg, 1.74 mmol) was dissolved in methanol (10 mL). (2R,3S,4R)-2,3,4,5-tetrahydroxypentanal (261 mg, 1.74 mmol) was added, followed by five drops of water. Sodium cyanoborohydride (328 mg, 5.22 mmol) was then added and pH adjusted to ~7.0 by the addition of acetic acid. The resulting solution was stirred at room temperature for 18 h. The volatiles were removed and the resulting crude product was purified by preparative HPLC (H2O/MeCN/AcOH 95/5/0.2 to 60/40/0.2 over 20 min). The relevant fractions were collected and freeze-dried. The title compound was dissolved in 2M HCl (4 ml) and freeze-dried, a procedure repeated three times, affording the HCl salt of the title compound (144 mg, 11%).

$^1$H NMR (500 MHz, MeOD) δ 1.30 (ddd, 2H), 1.84-2.13 (m, 3H), 2.32-2.45 (m, 4H), 2.62-2.77 (m, 2H), 2.81-2.98 (m, 7H), 3.15 (dd, 1H), 3.26 (d, 2H), 3.32-3.42 (m, 2H), 3.58-3.83 (m, 6H), 3.95 (t, 1H), 4.06 (dd, 1H), 4.55 (s, 1H), 7.05-7.33 (in, 4H).

EXAMPLE 2

3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide

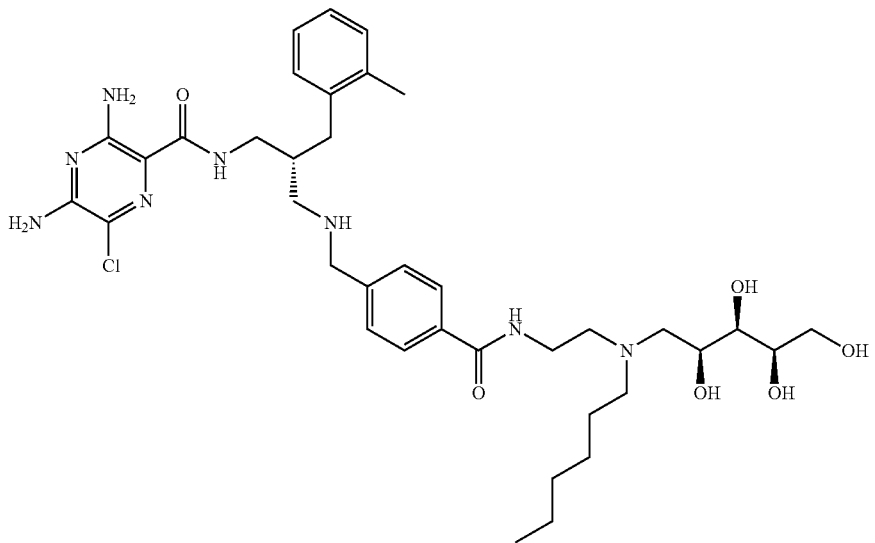 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)CO]

Method A

Step 1 tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)benzyl)carbamate

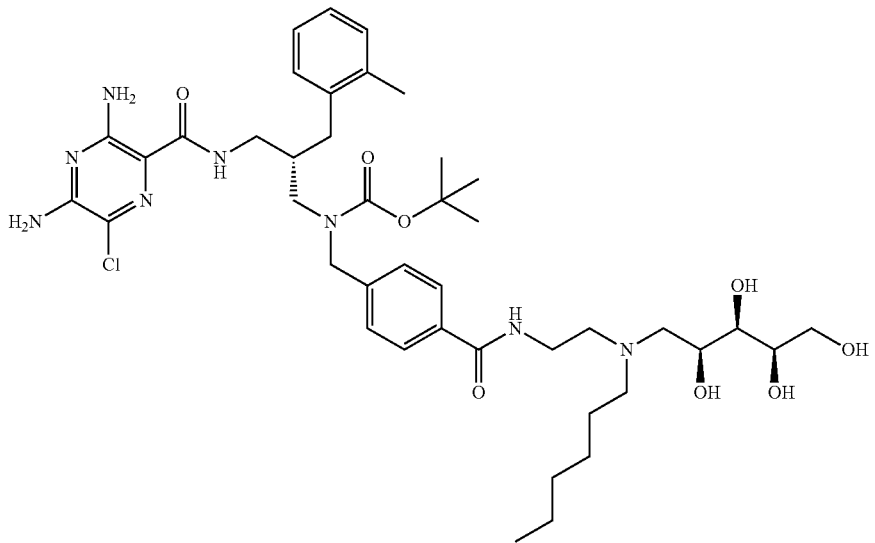 [SMILES: CCCCCCN(CCNC(=O)c1ccc(CN(C[C@H](CNC(=O)c2nc(Cl)c(N)nc2N)Cc2ccccc2C)C(=O)OC(C)(C)C)cc1)C[C@H](O)[C@@H](O)[C@H](O)CO]

(S)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate (Intermediate E, 1.23 g, 1.73 mmol), (2R,3S,4R)-2,3,4,5-tetrahydroxypentanal (0.521 g, 3.47 mmol) and DIPEA (0.303 mL, 1.73 mmol) were dissolved in MeOH (10 mL) and stirred at room temperature for 1 h. Sodium cyanoborohydride (0.327 g, 5.20 mmol) and acetic acid (0.099 mL, 1.73 mmol) were added and stirring continued at 50° C. for 3 days. The reaction was cooled to room temperature, quenched by addition of 8% NaHCO3 (aq), stirred for 15 min and was then concentrated in vacuo. The residue was dissolved in EtOAc (100 mL) and 8% NaHCO3 (aq) (50 mL), shaken and the phases separated. The aqueous phase was extracted with EtOAc (100 mL). The combined organic phases were dried with Na2SO4 (s), filtered and evaporated in vacuo. The compound was purified by preparative HPLC on a Kromasil C8 column (10 μm 250×50 ID mm) using a gradient of 20-60% acetonitrile in H2O/MeCN/AcOH 95/5/0.2 buffer over 20 minutes with a flow of 100 mL/min. The compounds were detected by UV at 268 nm. The compound was collected and freeze-dried to yield tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)benzyl)carbamate (1.21 g, 83%) as a white solid.

LC/MS: m/z 843.5 [M+H]$^+$

1H NMR (500 MHz, DMSO-d6) δ 0.74-0.85 (m, 3H), 1.12-1.27 (m, 6H), 1.27-1.45 (m, 11H), 2.20 (s, 3H), 2.25-2.35 (m, 1H), 2.39-2.66 (m, 6H), 2.9-3.06 (m, 1H), 3.06-3.51 (m, 12H), 3.53-3.6 (m, 1H), 3.6-3.72 (m, 1H), 4.2-4.68 (m, 5H), 6.97 (bs, 2H), 7.03-7.19 (m, 6H), 7.72 (d, 2H), 7.78-7.99 (m, 1H), 8.21-8.36 (m, 1H).

Step 2

3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide dihydrochloride

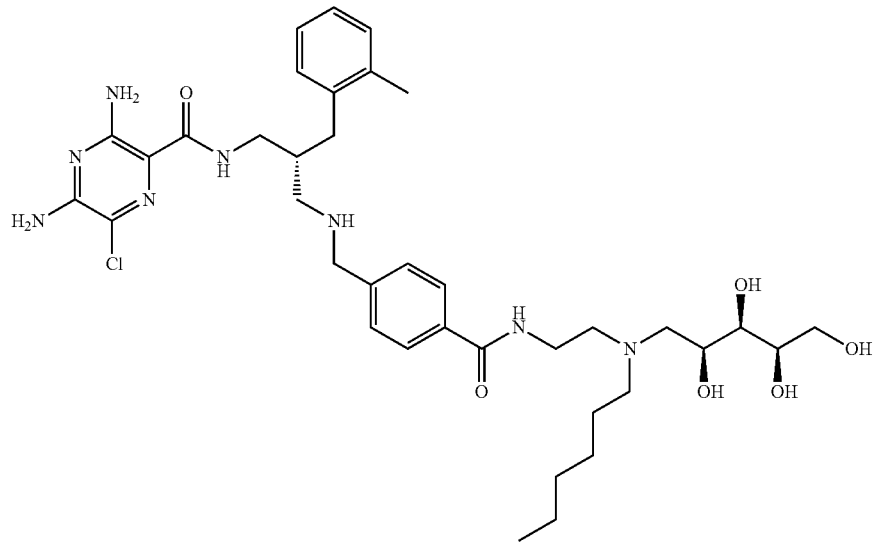 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)CO]

Acetyl chloride (5.69 mL, 80.0 mmol) was added dropwise to an icebath cooled flask of MeOH (20 mL). The mixture was stirred for 5 min and tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)benzyl)carbamate (1.21 g, 1.43 mmol) was added. The reaction was stirred at room temperature for 1.5 h and was then evaporated in vacuo. The residue was dissolved in water and freeze-dried to yield 3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide dihydrochloride (1.17 g, 100%) as a pale solid.

LC/MS: m/z 743.4 [M+H]$^+$

1H NMR (500 MHz, DMSO-d6) δ 0.8-0.9 (m, 3H), 1.2-1.33 (m, 6H), 1.62-1.74 (m, 2H), 2.26 (s, 3H), 2.3-2.41 (m, 1H), 2.59-2.74 (m, 2H), 2.74-2.85 (m, 1H), 2.86-2.98 (m, 1H), 3.09-3.51 (m, 11H), 3.56-3.62 (m, 1H), 3.62-3.75 (m, 2H), 3.99-4.09 (m, 1H), 4.14-4.29 (m, 2H), 4.58 (s, 4H), 7-7.21 (m, 6H), 7.62 (d, 2H), 7.92 (d, 2H), 8.27 (t, 1H), 8.91-9 (m, 1H), 9.16 (d, 2H), 9.52 (d, 1H).

Step 3

3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide

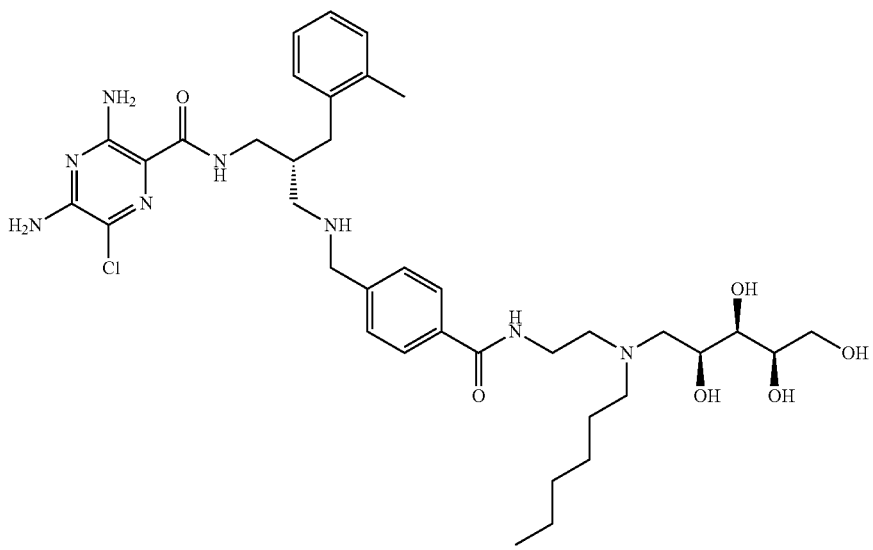 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)CO]

3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide dihydrochloride (1.17 g, 1.43 mmol) was dissolved in water (15 ml) and basified by addition of 10% Na2CO3 (aq) to pH ~11. The product was extracted with EtOAc (5×70 mL). The combined organic phases were dried with $Na_2SO_4$ (s), filtered and evaporated in vacuo to yield a semi solid/oil. The residue was dissolved in acetonitrile/water and freeze-dried to yield 3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide (1.02 g, 96%) as a pale solid.

LC/MS: m/z 743.5 $[M+H]^+$

1H NMR (500 MHz, DMSO-d6) δ 0.75-0.85 (m, 3H), 1.12-1.26 (m, 6H), 1.31-1.43 (m, 2H), 1.94-2.05 (m, 1H), 2.24 (s, 3H), 2.35-2.49 (m, 5H), 2.54-2.65 (m, 4H), 3.14-3.23 (m, 1H), 3.25-3.4 (m, 5H), 3.4-3.49 (m, 2H), 3.53-3.59 (m, 1H), 3.62-3.78 (m, 3H), 4.26 (d, 1H), 4.38 (d, 1H), 4.45 (t, 1H), 4.51 (d, 1H), 6.96 (bs, 2H), 7.03-7.14 (m, 4H), 7.40 (d, 2H), 7.74 (d, 2H), 8.24-8.37 (m, 2H).

Method B 3,5-diamino-6-chloro-N—((R)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide

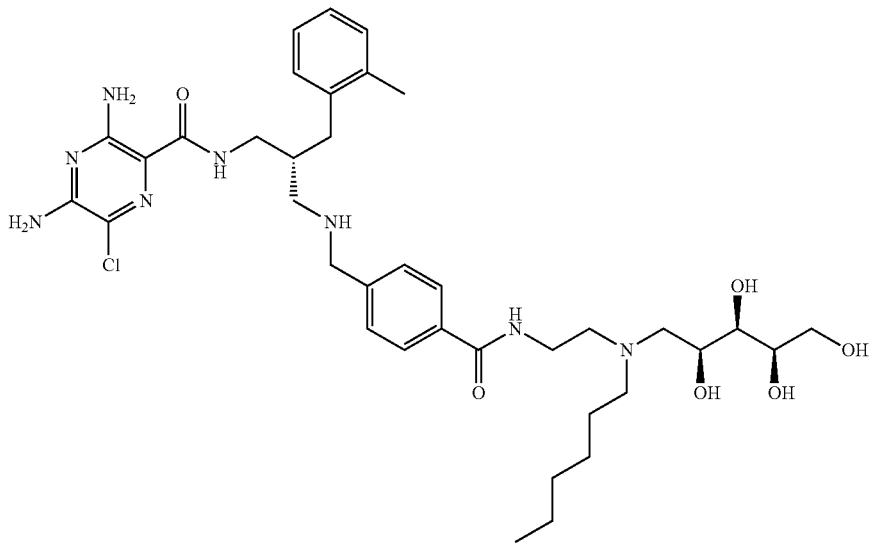 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)CO]

To a 5 L flange flask was charged a solution of 4-formyl-N-(2-(hexyl((2S,3R,4R)-2,3,4,5-tetrahydroxypentyl)amino)ethyl)benzamide (Intermediate I, 133 g, 108.5 g active, 0.26 mol) in EtOH (1500 mL), (R)-3,5-diamino-N-(3-amino-2-(2-methylbenzyl)propyl)-6-chloropyrazine-2-carboxamide (Intermediate A, 108.8 g, 0.31 mol), EtOH (230 mL) and DIPEA (64.4 mL, 0.37 mol). The mixture was heated to 40° C. for 1 h. To the clear solution was charged AcOH (45.4 ml, 0.79 mol). The solution was stirred at 40° C. for 20 min. To this was charged NaCNBH₃ (23.2 g, 0.37 mol) portionwise over 10 min, noting gas evolution. The mixture was stirred at 40° C. overnight. The reaction was cooled to room temperature, quenched carefully with sat. aq. NaHCO₃ (3100 mL) and stirred at room temperature for 1 h. The mixture was extracted with 10% MeOH/EtOAc (2×5000 mL) and 10% MeOH/DCM (5000 mL). The organic phases were combined and concentrated in vacuo to provide 271 g crude material. NMR analysis indicated ca. 80% purity, with NaCNBH₃ signals present. The residue was dissolved in DCM (12 L) and IPA (770 ml). The mixture was washed with a mixture of sat. aq. NaHCO₃ (2700 ml) and water (770 ml). The aqueous phase was extracted with DCM (1200 ml). The organics were combined and concentrated in vacuo to provide 298 g (191 g active, 97%) as a yellow solid. HPLC-MS indicated 88.0% purity. ¹H NMR indicated ca. 60% purity, with ca. 27 wt-% IPA and ca. 8 wt-% Intermediate A.

The so obtained crude (290 g, 235 mmol) was diluted in warm MeOH (750 mL) and acetonitrile (15 L) was added continuously while evaporating an azeotrop from the mixture. After approx. 10 L of solvent was evaporated the remaining mixture containing a gum like precipitate was stirred for additional 4 d at room temperature.

The liquid phase was decanted from the gum like residue. To the residue 2.5 L of acetonitrile was added and after stirring for 1 h and the acetonitrile was decanted. The so obtained crude (approx. 175 g) was subjected to a final purification by HPLC chromatography [CelluCoat 250×100 mm, 10 μm; mobile phase: MeOH/MeCN/TEA=95:5:0.1; injected amount: 1.0 g/cycle; cycle time: 3.5 min]. Yield of the title compound: 148 g (77%).

LC/MS: m/z 743.5 [M+H]⁺

¹H NMR (600 MHz, DMSO; in case of atropisomeric peaks, only the shift of the main atropisomer is reported) δ 0.80 (t, 3H), 1.34-1.4 (m, 2H), 1.09-1.24 (m, 6H), 1.34-1.4 (m, 2H), 2.00 (s, 1H), 2.00 (s, 1H), 2.24 (s, 3H), 2.36-2.42 (m, 1H), 2.43-2.49 (m, 4H), 2.51-2.54 (m, 1H), 2.56-2.64 (m, 4H), 3.15-3.22 (m, 1H), 3.23-3.3 (m, 3H), 3.35-3.4 (m, 1H), 3.42 (s, 1H), 3.43-3.49 (m, 1H), 3.54-3.59 (m, 1H), 3.62-3.7 (m, 2H), 3.74 (d, 1H), 4.27 (s, 1H), 4.39 (s, 1H), 4.46 (t, 1H), 4.52 (s, 1H), 6.96 (s, 1H), 7.03-7.08 (m, 2H), 7.40 (d, 2H), 7.74 (d, 2H), 8.26-8.31 (m, 1H), 8.31-8.35 (m, 1H).

¹³C NMR (151 MHz, DMSO) δ 13.91, 19.04, 22.08, 26.48, 26.61, 31.27, 34.23, 37.42, 38.60, 41.55, 50.84, 53.06, 53.44, 54.55, 57.43, 62.65, 69.23, 71.12, 72.61, 112.95, 117.12, 125.54, 125.83, 126.89, 127.72, 129.63, 130.03, 132.85, 135.82, 138.74, 144.02, 152.69, 154.14, 165.55, 166.01.

Chiral HPLC (method A; heptane/IPA/TEA 75:25:0.1): 98.9% ee, Rt=14.75 min (R), 18.63 min (S).

EXAMPLE 3

3,5-diamino-6-chloro-N—((R)-3-((1-(2-(hexyl((2S, 3R,4R,5R)-2,3,4,5,6-pentahydroxyhexyl)amino) ethylcarbamoyl)piperidin-4-yl)methylamino)-2-(2-methylbenzyl)propyl)pyrazine-2-carboxamide

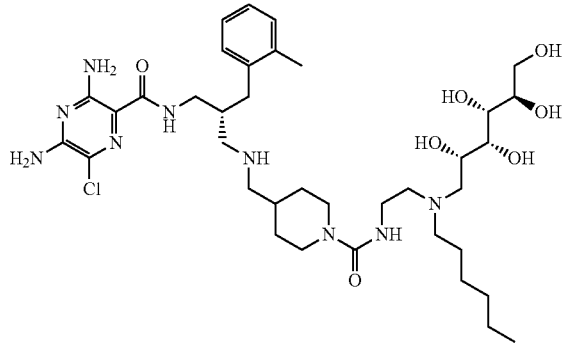 [SMILES: CCCCCCN(CCNC(=O)N1CCC(CNC[C@H](CNC(=O)c2nc(Cl)c(N)nc2N)Cc2ccccc2C)CC1)C[C@H](O)[C@@H](O)[C@H](O)[C@H](O)CO]

Step 1:

(9H-fluoren-9-yl)methyl 2-(((2S,3R)-2,3-dihydroxy-3-((4R,5R)-5-hydroxy-2-phenyl-1,3-dioxan-4-yl) propyl)(hexyl)amino)ethylcarbamate

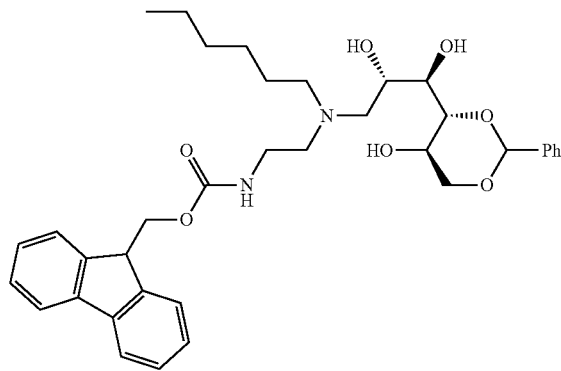

Into a 100-mL round-bottom flask, was placed 9H-fluoren-9-ylmethyl N-(2-aminoethyl)carbamate hydrochloride (1.50 g, 4.71 mmol, 1.0 equiv), (2R,4aR,7R,8R,8aS)-2-phenyl-hexahydro-2H-pyrano[3,2-d][1,3]dioxine-6,7,8-triol (1.51 g, 5.63 mmol, 1.20 equiv), methanol (30 mL). After stirring the above mixture for 30 min, NaBH$_3$CN (590 mg, 9.39 mmol, 2.00 equiv), AcOH (570 mg, 9.49 mmol, 2.0 equiv) was added. The resulting solution was stirred overnight at room temperature. Then hexanal (530 mg, 5.29 mmol, 1.50 equiv) was added, followed by more NaBH$_3$CN (450 mg, 7.16 mmol, 2.00 equiv). The resulting solution was stirred for 5 hours at room temperature. Then it was concentrated under vacuum. The resulting mixture was washed with of water, extracted with ethyl acetate and the organic layers combined and dried over Na2SO4. The solids were filtered out. This resulted in 1.6 g (73%) of the title compound as light yellow oil.

LC/MS: m/z 619 [M+H]$^+$ $^1$H NMR (300 MHz, CD$_3$OD): 1.80-1.92 (m, 3H), 1.15-1.40 (m, 6H), 1.41-1.72 (m, 2H), 2.88-3.15 (m, 5H), 3.33-3.43 (m, 2H), 3.55-3.61 (m, 1H), 3.67-3.83 (m, 1H), 3.85-4.12 (m, 3H), 4.22-4.40 (m, 4H), 5.57 (s, 1H), 7.33-7.65 (9H, m), 7.67 (d, 2H), 7.83 (d, 2H).

Step 2:

(1R,2S)-3-((2-aminoethyl)(hexyl)amino)-1-[(2R,4R, 5R)-5-hydroxy-2-phenyl-1,3-dioxan-4-yl]propane-1, 2-diol Into a 50-mL round-bottom flask, was placed 9H-fluoren-9-ylmethyl N-(2-[[(2S,3R)-2,3-dihydroxy-3-[(2R,4R,5R)-5-hydroxy-2-phenyl-1,3-dioxan-4-yl]propyl](hexyl)amino] ethyl)carbamate (1.6 g, 2.59 mmol, 1.0 equiv), methanol (10 mL), diethylamine (5 mL). The resulting solution was stirred overnight at room temperature. The residue was applied onto a silica gel column and eluted with ammonia/MeOH (1:100). This resulted in 600 mg (59%) of the title compound as yellow solid.

LC/MS: m/z 397 [M+H]$^+$

Step 3:

(9H-fluoren-9-yl)methyl (S)-3-(3,5-diamino-6-chloropyrazine-2-carboxamido)-2-(2-methylbenzyl)propyl((1-(2-(((2S,3R)-2,3-dihydroxy-3-((2R,4R,5R)-5-hydroxy-2-phenyl-1,3-dioxan-4-yl)propyl)(hexyl) amino)ethylcarbamoyl)piperidin-4-yl)methyl) carbamate Into a 50-mL round-bottom flask, was placed (S)-(9H-fluoren-9-yl)methyl-3-(3,5-diamino-6-chloropyrazine-2-carboxamido)-2-(2-methylbenzyl)propyl(piperidin-4-ylmethyl)carbamate (Intermediate B, 400 mg, 0.60 mmol, 1.0 equiv), triethylamine (177 mg, 1.75 mmol, 3.0 equiv), triphosgen (173 mg, 0.58 mmol, 1.0 equiv) in DCM (5 mL). The resulting solution was stirred for 0.5 h at room temperature. The resulting mixture was washed with 3×10 mL of water. The resulting mixture was concentrated under vacuum to give the intermediate chloroformamide which was added dropwise (dissolved in DCM) to a solution of triethylamine (177 mg, 1.75 mmol, 3.0 equiv) and (1R,2S)-3-[(2-aminoethyl)(hexyl)amino]-1-[(2R,4R,5R)-5-hydroxy-2-phenyl-1,3-dioxan-4-yl]propane-1,2-diol (347 mg, 0.88 mmol, 1.50 equiv) in DCM (5 mL) were stirred for 2 h at room temperature. The resulting mixture was concentrated in vacuo. The residue was purified by preparative TLC with DCM/MeOH (10:1). This resulted in 145 mg (22%) of the title compound as a yellow solid.

LC/MS: m/z 1090 [M+H]+

Step 4:

(9H-fluoren-9-yl)methyl (S)-3-(3,5-diamino-6-chloropyrazine-2-carboxamido)-2-(2-methylbenzyl)propyl((1-(2-(hexyl((2S,3R,4R,5R)-2,3,4,5,6-pentahydroxyhexyl)amino)ethylcarbamoyl)piperidin-4-yl)methyl)carbamate

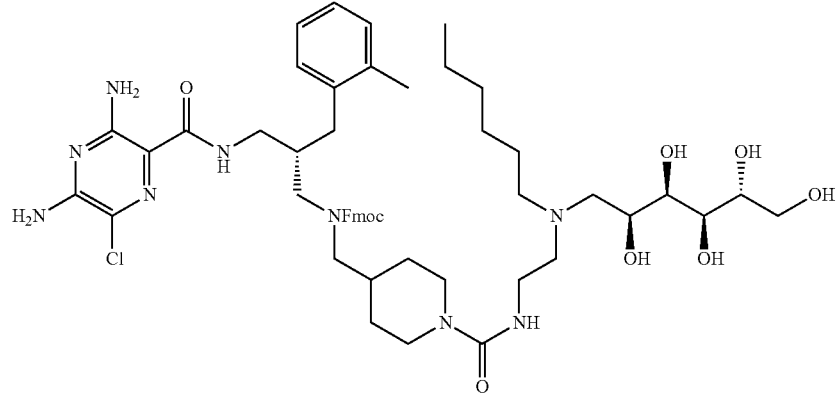

Into a 8-mL vial, was placed (9H-fluoren-9-yl)methyl (S)-3-(3,5-diamino-6-chloropyrazine-2-carboxamido)-2-(2-methylbenzyl)propyl((1-(2-(((2S,3R)-2,3-dihydroxy-3-((2R,4R,5R)-5-hydroxy-2-phenyl-1,3-dioxan-4-yl)propyl)(hexyl)amino)ethylcarbamoyl)piperidin-4-yl)methyl)carbamate (144 mg, 0.13 mmol, 1.0 equiv), ethanol (0.5 mL), 4M HCl (3 mL). The resulting solution was stirred overnight at room temperature. The resulting mixture was concentrated under vacuum. This resulted in 120 mg (crude) of the title compound as yellow oil.

LC/MS: m/z 1002 [M+H]+

Step 5:

3,5-diamino-6-chloro-N—((R)-3-((1-(2-(hexyl((2S,3R,4R,5R)-2,3,4,5,6-pentahydroxyhexyl)amino)ethylcarbamoyl)piperidin-4-yl)methylamino)-2-(2-methylbenzyl)propyl)pyrazine-2-carboxamide

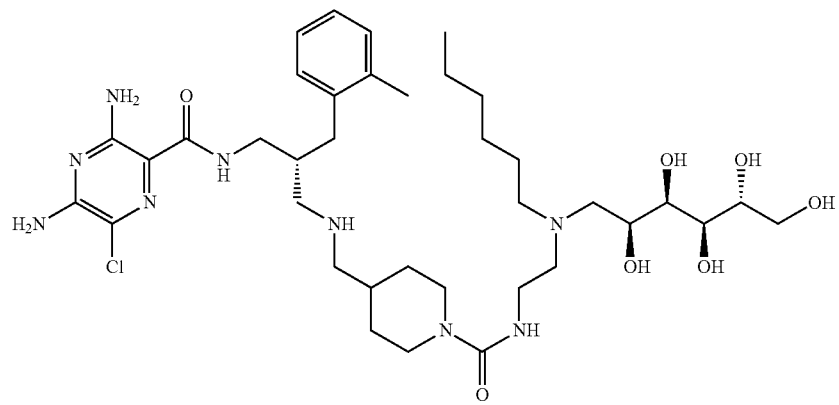 [SMILES: CCCCCCN(CCNC(=O)N1CCC(CNC[C@H](CNC(=O)c2nc(Cl)c(N)nc2N)Cc2ccccc2C)CC1)C[C@H](O)[C@@H](O)[C@H](O)[C@H](O)CO]

Into a 50-mL round-bottom flask, was placed 9H-fluoren-9-yl)methyl (S)-3-(3,5-diamino-6-chloropyrazine-2-carboxamido)-2-(2-methylbenzyl)propyl((1-(2-(hexyl((2S,3R,4R,5R)-2,3,4,5,6-pentahydroxyhexyl)amino)ethylcarbamoyl)piperidin-4-yl)methyl)carbamate (120 mg, 0.12 mmol, 1.0 equiv), diethylamine (2 mL) in N,N-dimethylformamide (4 mL). The resulting solution was stirred overnight at room temperature. The resulting mixture was concentrated under vacuum. The crude product (100 mg) was purified by Prep-HPLC with the following conditions (2#-AnalyseHPLC-SHIMADZU (HPLC-10)): Column, XBridge Prep C18 OBD Column, 5 um, 19*150 mm; mobile phase, WATER WITH 0.05% TFA and ACN (23.0% ACN up to 33.0% in 15 min); Detector, MS, UV 254 nm. This resulted in 8 mg (7%) of the title compound as a yellow solid.

LC/MS: m/z 780 [M+H]+

¹H NMR (300 MHz, CD₃OD): 0.91-0.95 (m, 3H), 1.27-1.38 (m, 8H), 1.81-1.97 (m, 5H), 2.36 (s, 4H), 2.62-2.69 (m, 1H), 2.86-2.96 (m, 7H), 3.31-3.55 (m, 3H), 3.63-3.68 (m, 6H), 3.70-3.83 (m, 6H), 4.05-4.17 (m, 3H), 7.13-7.20 (m, 4H)

EXAMPLE 4

3,5-diamino-6-chloro-N—((R)-3-((1-(3-(hexyl((2S,3R,4R,5R)-2,3,4,5,6-pentahydroxyhexyl)amino)propanoyl)piperidin-4-yl)methylamino)-2-(2-methylbenzyl)propyl)pyrazine-2-carboxamide

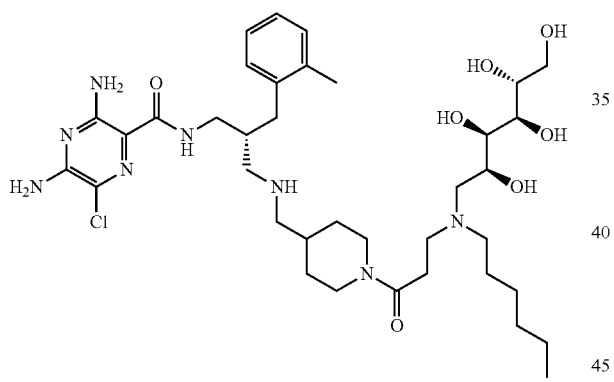

Step 1:

benzyl 3-((2S,3R)-2,3-dihydroxy-3-((2R,4R,5R)-5-hydroxy-2-phenyl-1,3-dioxan-4-yl)propylamino)propanoate

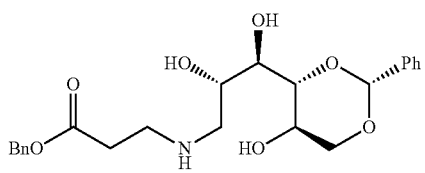 [SMILES: O=C(CCNC[C@H](O)[C@@H](O)[C@@H]1O[C@H](c2ccccc2)OC[C@H]1O)OCc1ccccc1]

Into a 100-mL round-bottom flask, was placed 4-methylbenzene-1-sulfonic acid benzyl 3-aminopropanoate (2.00 g, 5.69 mmol, 1.0 equiv), (2R,4aR,7R,8R,8aS)-2-phenyl-hexahydro-2H-pyrano[3,2-d][1,3]dioxine-6,7,8-triol (2.29 g, 8.54 mmol, 1.5 equiv), methanol (30 mL). After 30 min, NaBH₃CN (720 mg, 11.46 mmol, 2.00 equiv), AcOH (680 mg, 11.32 mmol, 2.0 equiv) was added. The resulting solution was stirred overnight at room temperature. The resulting mixture was concentrated, diluted with ethyl acetate and washed with water. The organic layers were dried over anhydrous sodium sulfate. The solids were filtered off. Removal of the solvents in vacuo resulted in 1.9 g (77%) the title compound as colorless oil which was used in next step directly.

LC/MS: m/z 967 [M+H]+

Step 2:

benzyl 3-(((2S,3R)-2,3-dihydroxy-3-((2R,4R,5R)-5-hydroxy-2-phenyl-1,3-dioxan-4-yl)propyl)(hexyl)amino)propanoate

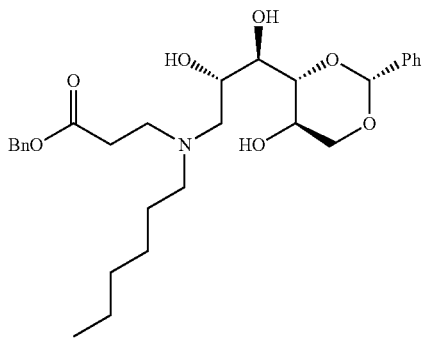 [SMILES: CCCCCCN(CCC(=O)OCc1ccccc1)C[C@H](O)[C@@H](O)[C@@H]1O[C@H](c2ccccc2)OC[C@H]1O]

Into a 100-mL round-bottom flask, was placed benzyl 3-[[(2S,3R)-2,3-dihydroxy-3-[(2R,4R,5R)-5-hydroxy-2-phenyl-1,3-dioxan-4-yl]propyl]amino]propanoate (1.90 g, crude), hexanal (660 mg, 6.59 mmol, 1.5 equiv), methanol (30 mL). After 30 min, NaBH₃CN (550 mg, 8.75 mmol, 2.0 equiv) and AcOH (530 mg, 8.83 mmol, 2.0 equiv) were added. The resulting solution was stirred overnight at room temperature. The resulting mixture was concentrated, diluted with ethyl acetate and washed with water, the organic layers were dried over anhydrous sodium sulfate. The solids were filtered out. The residue was applied onto a silica gel column and eluted with ethyl acetate/petroleum ether (1:2). This resulted in 1.3 g (57%) of benzyl 3-[[(2S,3R)-2,3-dihydroxy-3-[(2R,4R,5R)-5-hydroxy-2-phenyl-1,3-dioxan-4-yl]propyl](hexyl)amino]propanoate as light yellow oil.

LC/MS: m/z 516 [M+H]+

Step 3:

3-(((2S,3R)-2,3-dihydroxy-3-((2R,4R,5R)-5-hydroxy-2-phenyl-1,3-dioxan-4-yl)propyl)(hexyl)amino)propanoic Acid

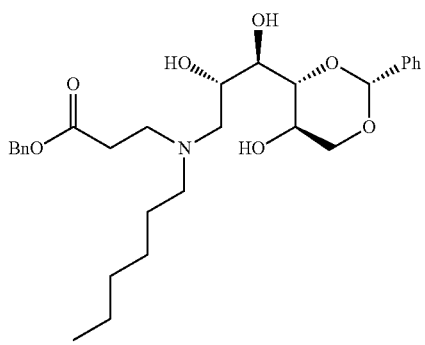 [SMILES: CCCCCCN(CCC(=O)OCc1ccccc1)C[C@H](O)[C@@H](O)[C@@H]1O[C@H](c2ccccc2)OC[C@H]1O]

Into a 100-mL round-bottom flask, was placed benzyl 3-[[(2S,3R)-2,3-dihydroxy-3-[(2R,4R,5R)-5-hydroxy-2-phenyl-1,3-dioxan-4-yl]propyl](hexyl)amino]propanoate (1.3 g, 2.52 mmol, 1.0 equiv), Pd/C (5 wt %, 700 mg), ethanol (20 mL). To the above mixture, $H_2$ (g). The resulting solution was stirred under $H_2$-atmosphere overnight at room temperature. The solids were filtered off. The filtrate was concentrated under vacuum. This resulted in 0.5 g (47%) of 3-[[(2S,3R)-2,3-dihydroxy-3-[(2R,4R,5R)-5-hydroxy-2-phenyl-1,3-dioxan-4-yl]propyl](hexyl)amino]propanoic acid as colorless oil.

LC/MS: m/z 426 [M+H]$^+$

Step 4:

(9H-fluoren-9-yl)methyl (S)-3-(3,5-diamino-6-chloropyrazine-2-carboxamido)-2-(2-methylbenzyl)propyl((1-(3-(((2S,3R)-2,3-dihydroxy-3-((2R,4R,5R)-5-hydroxy-2-phenyl-1,3-dioxan-4-yl)propyl)(hexyl)amino)propanoyl)piperidin-4-yl)methyl)carbamate equiv), N,N-dimethylformamide (5 mL). The resulting solution was stirred for 2 h at room temperature. Water was added to the above mixture and the suspension was extracted with ethyl acetate. The organic layers combined and washed with brine. The mixture was dried over anhydrous sodium sulfate. The solids were filtered off and the filtrate was evaporated in vacuo. The residue was purified by preparative TLC (DCM:MeOH=10:1). Relevant fractions were collected and after removal of the volatiles resulted in 200 mg (62%) of the title compound as a yellow solid.

LC/MS: m/z 1076 [M+H]$^+$

Step 5:

(9H-fluoren-9-yl)methyl (S)-3-(3,5-diamino-6-chloropyrazine-2-carboxamido)-2-(2-methylbenzyl)propyl((1-(3-(hexyl((2S,3R,4R,5R)-2,3,4,5,6-pentahydroxyhexyl)amino)propanoyl)piperidin-4-yl)methyl)carbamate

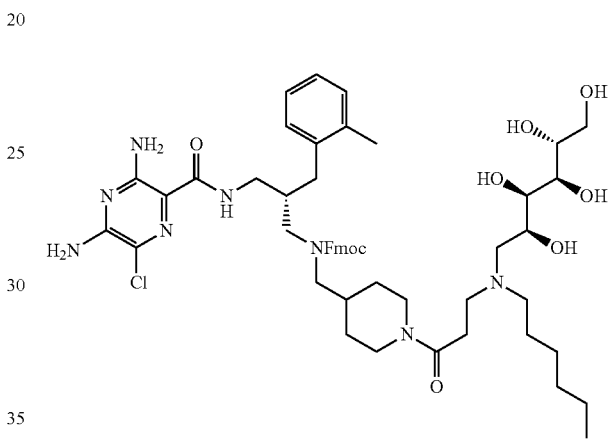

Into a 50-mL round-bottom flask, was placed (9H-fluoren-9-yl)methyl (S)-3-(3,5-diamino-6-chloropyrazine-2-carboxamido)-2-(2-methylbenzyl)propyl((1-(3-(((2S,3R)-2,3-

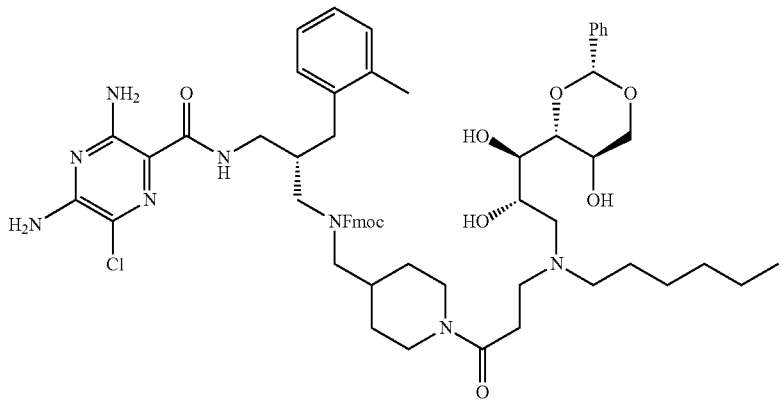

Into a 50-mL round-bottom flask, was placed 3-[[(2S,3R)-2,3-dihydroxy-3-[(2R,4R,5R)-5-hydroxy-2-phenyl-1,3-dioxan-4-yl]propyl](hexyl)amino]propanoic acid (381.49 mg, 0.90 mmol, 3.00 equiv), (S)-(9H-fluoren-9-yl)methyl 3-(3,5-diamino-6-chloropyrazine-2-carboxamido)-2-(2-methylbenzyl)propyl(piperidin-4-ylmethyl)carbamate (Intermediate B, 200.0 mg, 0.30 mmol, 1.0 equiv), HATU (170.5 mg, 0.45 mmol, 1.5 equiv), DIEA (57.9 mg, 0.45 mmol, 1.5 dihydroxy-3-((2R,4R,5R)-5-hydroxy-2-phenyl-1,3-dioxan-4-yl)propyl)(hexyl)amino)propanoyl)piperidin-4-yl)methyl) carbamate (step 4, 200 mg, 0.19 mmol, 1.0 equiv) and and solution of HCl (4M in ethanol, 2 mL). The resulting solution was stirred overnight at room temperature. Evaporation of the volatiles resulted in 200 mg of the crude title compound as a yellow solid.

LC/MS: m/z 987 [M+H]$^+$

Step 6:

3,5-diamino-6-chloro-N—((R)-3-((1-(3-(hexyl((2S, 3R,4R,5R)-2,3,4,5,6-pentahydroxyhexyl)amino) propanoyl)piperidin-4-yl)methylamino)-2-(2-methylbenzyl)propyl)pyrazine-2-carboxamide

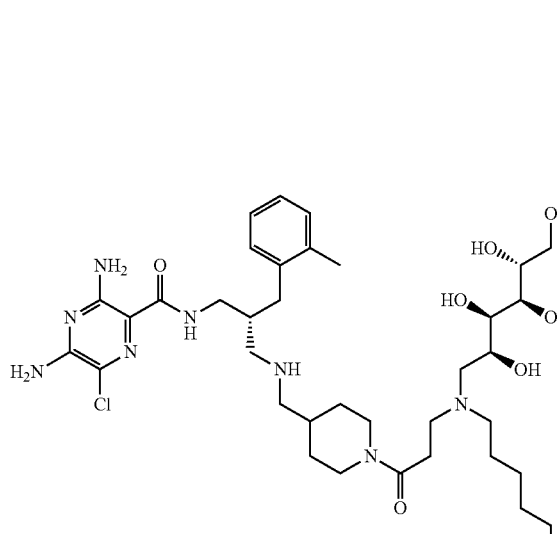

Into a 25-mL round-bottom flask, was placed (9H-fluoren-9-yl)methyl (S)-3-(3,5-diamino-6-chloropyrazine-2-carboxamido)-2-(2-methylbenzyl)propyl((1-(3-(hexyl((2S,3R,4R,5R)-2,3,4,5,6-pentahydroxyhexyl)amino)propanoyl)piperidin-4-yl)methyl)carbamate (step 5200 mg, 0.20 mmol, 1.00 equiv), methanol (6 mL), diethylamine (3 mL). The resulting solution was stirred overnight at room temperature. The resulting mixture was concentrated under vacuum. The crude product (100 mg) was purified by Prep-HPLC with the following conditions (Prep-HPLC-019): Column, XSelect CSH Prep C18 OBD Column, 5 um, 19*150 mm; mobile phase, WATER WITH 0.05% TFA and MeCN (22.0% MeCN up to 30.0% in 8 min, up to 100% in 1 min, hold 100% in 1 min, down to 22% in 2 min); Detector, UV 254/220 nm. This resulted in 38 mg (21%) of 3,5-diamino-6-chloro-N-[(2R)-3-([[1-(3-[hexyl[(2S,3R,4R,5R)-2,3,4,5,6-pentahydroxyhexyl]amino]propanoyl)piperidin-4-yl]methyl]amino)-2-[(2-methylphenyl)methyl]propyl] pyrazine-2-carboxamide; trifluoroacetic acid as a yellow solid.

$^1$H NMR (300 MHz, CD$_3$OD): δ 0.95-0.97 (m, 3H), 1.22-1.50 (m, 8H), 1.70-2.10 (m, 5H), 2.30-2.51 (m, 4H), 2.63-2.81 (m, 2H), 2.88-3.16 (m, 7H), 3.16-3.20 (m, 2H), 3.34-3.78 (m, 5H), 3.51-3.87 (m, 7H), 3.95-4.10 (m, 1H), 4.10-4.25 (m, 1H), 4.54 (d, 1H), 7.14-7.22 (m, 4H).

LC/MS: m/z 765 [M+H]$^+$

EXAMPLE 5

3,5-diamino-6-chloro-N—((R)-3-((1-(3-(hexyl((2S, 3R,4R)-2,3,4,5-tetrahydroxypentyl)amino)propanoyl)piperidin-4-yl)methylamino)-2-(2-methylbenzyl)propyl)pyrazine-2-carboxamide

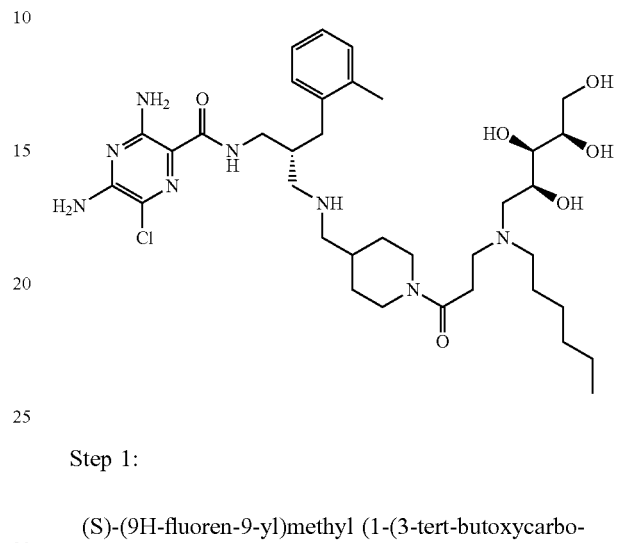

Step 1:

(S)-(9H-fluoren-9-yl)methyl (1-(3-tert-butoxycarbonylaminopropanoyl)piperidin-4-yl)methyl(3-(3,5-diamino-6-chloropyrazine-2-carboxamido)-2-(2-methylbenzyl)propyl)carbamate

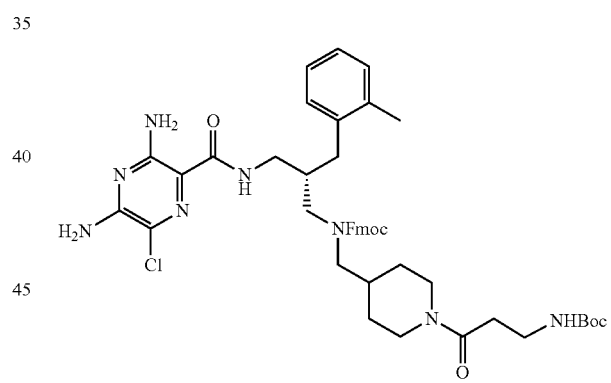

A flask (25 mL) was charged with (S)-(9H-fluoren-9-yl) methyl 3-(3,5-diamino-6-chloropyrazine-2-carboxamido)-2-(2-methylbenzyl)propyl(piperidin-4-ylmethyl)carbamate (Intermediate B, 300 mg, 0.45 mmol), 3-(tert-butoxycarbonylamino)propanoic acid (100 mg, 0.53 mmol), DIPEA (145 mg, 1.13 mmol), HATU (342 mg, 0.9 mmol) and DMF (10 mL) was added. The reaction was stirred for 6 h at room temperature. The mixture was diluted with 25 mL of ethyl acetate and washed by water (3×25 mL). The organic layer was dried over anhydrous Na$_2$SO$_4$. The precipitation was filtered off and the filtrate was concentrated under vacuum. The obtained crude product was purified by a silica gel column with dichloromethane/methanol (20:1, v/v) to afford the title compound (280 mg, 67%) as light yellow solid.

LC/MS: m/z 839 [M+H]$^+$

Step 2:

(S)-(9H-fluoren-9-yl)methyl (1-(3-aminopropanoyl) piperidin-4-yl)methyl(3-(3,5-diamino-6-chloropyrazine-2-carboxamido)-2-(2-methylbenzyl)propyl) carbamate

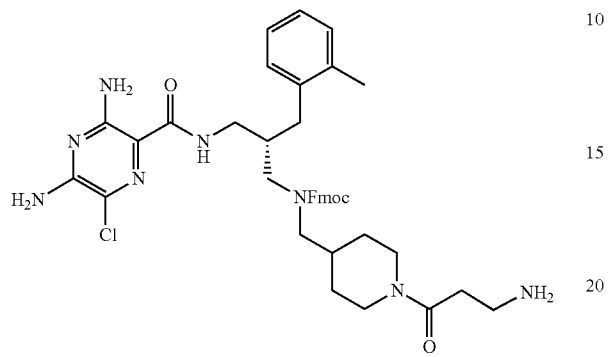

Into a 50-mL round-bottom flask was placed (S)-(9H-fluoren-9-yl)methyl (1-(3-tert-butoxycarbonylaminopropanoyl)piperidin-4-yl)methyl(3-(3,5-diamino-6-chloropyrazine-2-carboxamido)-2-(2-methylbenzyl)propyl)carbamate (step 1, 216 mg, 0.26 mmol, 1.0 equiv) and hydrogen chloride (4M in methanol, 5 mL). The resulting solution was stirred for 1 h at room temperature. Evaporation of the volatiles resulted in 190 mg of the crude title compound as a yellow solid.

LC/MS: m/z 739 [M+H]$^+$

Step 3:

(9H-fluoren-9-yl)methyl (S)-3-(3,5-diamino-6-chloropyrazine-2-carboxamido)-2-(2-methylbenzyl)propyl((1-(3-(hexyl((2S,3R,4R)-2,3,4,5-tetrahydroxypentyl)amino)propanoyl)piperidin-4-yl)methyl) carbamate

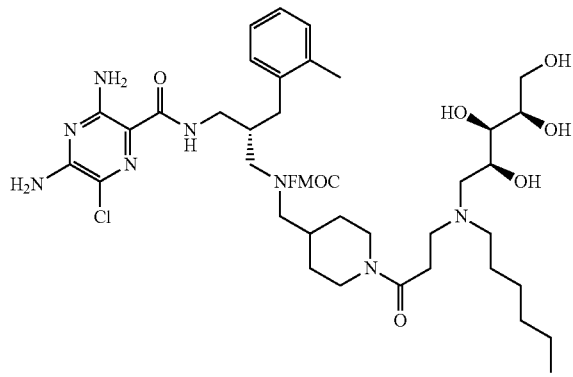

Into a 50-mL round-bottom flask, was placed (S)-(9H-fluoren-9-yl)methyl (1-(3-aminopropanoyl)piperidin-4-yl) methyl(3-(3,5-diamino-6-chloropyrazine-2-carboxamido)-2-(2-methylbenzyl)propyl)carbamate (step 2, 190 mg, 0.26 mmol, 1.0 equiv), (3R,4S,5R)-oxane-2,3,4,5-tetrol (39 mg, 0.26 mmol, 1.0 equiv), methanol (6 mL). After 30 min, NaBH$_3$CN (66 mg, 1.05 mmol, 4.0 equiv) was added slowly at 0° C. The resulting solution was stirred overnight at room temperature. Then hexanal (39 mg, 0.39 mmol, 1.0 equiv) was added, followed by more NaBH3CN (66 mg, 1.05 mmol, 4.0 equiv). The resulting solution was stirred for 5 h at room temperature. The solvent was removed to give the crude product, which was used in the next step directly without further purification.

LC/MS: m/z 957 [M+H]$^+$

Step 4:

3,5-diamino-6-chloro-N—((R)-3-((1-(3-(hexyl((2S,3R,4R)-2,3,4,5-tetrahydroxypentyl)amino)propanoyl)piperidin-4-yl)methylamino)-2-(2-methylbenzyl)propyl)pyrazine-2-carboxamide

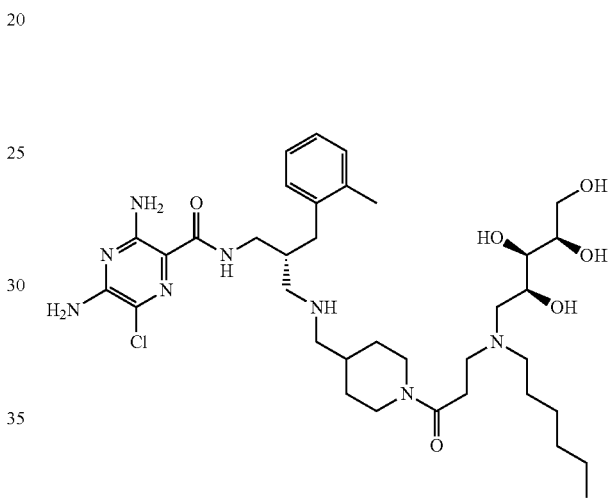

Into a 50-mL round-bottom flask was placed (9H-fluoren-9-yl)methyl (S)-3-(3,5-diamino-6-chloropyrazine-2-carboxamido)-2-(2-methylbenzyl)propyl((1-(3-(hexyl((2S,3R,4R)-2,3,4,5-tetrahydroxypentyl)amino)propanoyl)piperidin-4-yl)methyl)carbamate (step 3, 230 mg, 0.24 mmol, 1.00 equiv), methanol (5 mL), diethylamine (0.5 mL). The resulting solution was stirred for 3 h at room temperature. The crude product was purified by Prep-HPLC with the following conditions (Prep-HPLC-019): Column, XSelect CSH Prep C18 OBD Column, 5 um, 19*150 mm; mobile phase, WATER WITH 0.05% TFA and MeCN (18.0% MeCN up to 35.0% in 8 min, up to 100.0% in 1 min, hold 100.0% in 1 min, down to 18.0% in 2 min); Detector, UV 254/220 nm. This resulted in 36.9 mg (16%) of the title compound as a yellow solid.

LC/MS: m/z 735 [M+H]$^+$ $^1$H NMR (300 MHz, CD$_3$OD): δ 0.96 (d, 3H), 1.26-1.40 (m, 8H), 1.81-2.01 (m, 5H), 2.37 (s, 4H), 2.62-2.94 (m, 9H), 3.17-3.47 (m, 7H), 3.55-3.78 (m, 6H), 3.98 (d, 1H), 4.15 (s, 1H), 4.56 (d, 1H), 7.14-7.21 (m, 4H).

EXAMPLE 6

3,5-diamino-6-chloro-N—((R)-3-((1-(4-(hexyl((2S,3R,4R,5R)-2,3,4,5,6-pentahydroxyhexyl)amino)butanoyl)piperidin-4-yl)methylamino)-2-(2-methylbenzyl)propyl)pyrazine-2-carboxamide

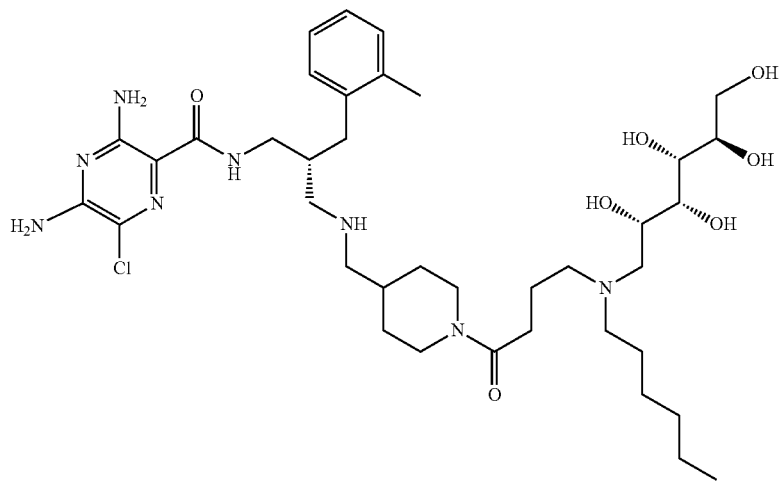 [SMILES: CCCCCCN(CCCC(=O)N1CCC(CNC[C@H](CNC(=O)c2nc(Cl)c(N)nc2N)Cc2ccccc2C)CC1)C[C@H](O)[C@@H](O)[C@H](O)[C@H](O)CO]

flash chromatography on silica gel, eluted by a gradient of 20 to 70% EtOAc in petroleum ether. Pure fractions were evaporated to dryness to afford the title compound (834 mg, 73%) as a yellow solid.

LC/MS: m/z 853 [M+H]$^+$

Step 1:

(S)-(9H-fluoren-9-yl)methyl ((1-(4-((tert-butoxycarbonyl)amino)butanoyl)piperidin-4-yl)methyl)(3-(3,5-diamino-6-chloropyrazine-2-carboxamido)-2-(2-methylbenzyl)propy)carbamate

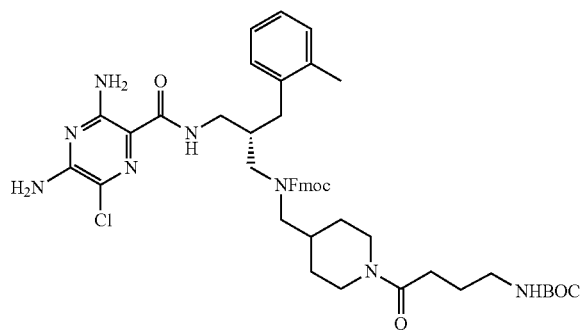

In a 50 mL round-bottomed flask was placed (S)-(9H-fluoren-9-yl)methyl (3-(3,5-diamino-6-chloropyrazine-2-carboxamido)-2-(2-methylbenzyl)propyl)(piperidin-4-ylmethyl)carbamate (Intermediate B, 900 mg, 1.35 mmol), 4-((tert-butoxycarbonyl)amino)butanoic acid (821 mg, 4.04 mmol), HATU (2305 mg, 6.06 mmol), and DIEA (1.06 mL, 6.06 mmol) in DMF (10 mL) to give a yellow solution. The resulting solution was stirred at 25° C. for 16 h. The reaction mixture was diluted with EtOAc (50 mL), and washed sequentially with water (50 mL). The organic layer was dried over Na$_2$SO$_4$, filtered and evaporated in vacuo to afford crude product. The crude product was purified by Step 2:

(S)-(9H-fluoren-9-yl)methyl (1-(4-aminobutanoyl)piperidin-4-yl)methyl(3-(3,5-diamino-6-chloropyrazine-2-carboxamido)-2-(2-methylbenzyl)propyl)carbamate

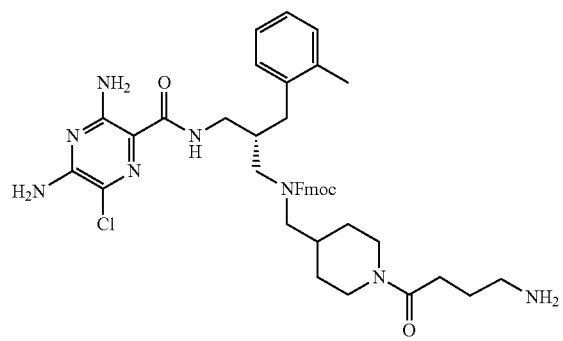

(S)-(9H-fluoren-9-yl)methyl ((1-(4-((tert-butoxycarbonyl)amino)butanoyl)piperidin-4-yl)methyl)(3-(3,5-diamino-6-chloropyrazine-2-carboxamido)-2-(2-methylbenzyl)propyl)carbamate (step 1, 834 mg, 0.98 mmol) was dissolved in a methanolic solution of HCl (4M) and stirred at room temperature for 1 h. The solvent was evaporated in vacuo to afford the title compound as a yellow solid.

LC/MS: m/z 753 [M+H]$^+$

Step 3:

(9H-fluoren-9-yl)methyl (S)-3-(3,5-diamino-6-chloropyrazine-2-carboxamido)-2-(2-methylbenzyl)propyl((1-(4-((2S,3R)-2,3-dihydroxy-3-((2R,4R,5R)-5-hydroxy-2-phenyl-1,3-dioxan-4-yl)propylamino)butanoyl)piperidin-4-yl)methyl)carbamate

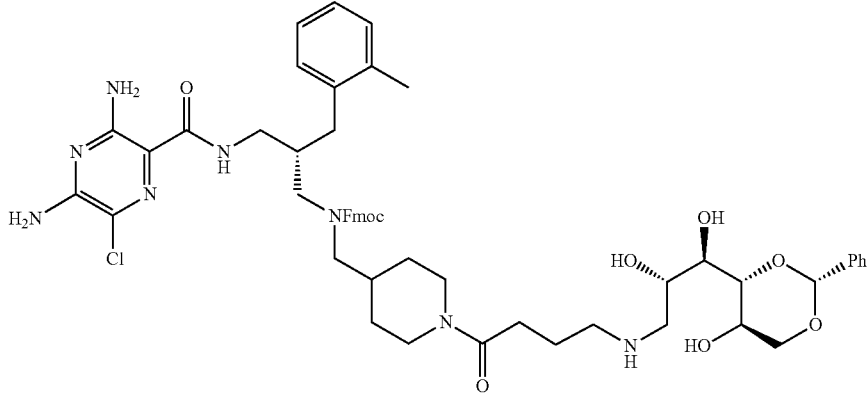

Into a 25-mL round-bottom flask was placed (S)-(9H-fluoren-9-yl)methyl (1-(4-aminobutanoyl)piperidin-4-yl)methyl(3-(3,5-diamino-6-chloropyrazine-2-carboxamido)-2-(2-methylbenzyl)propyl)carbamate (step 2, 250 mg, 0.33 mmol, 1.0 equiv), acetal protected D-glucose (2R,4aR,7R,8R,8aS)-2-phenyl-hexahydro-2H-pyrano[3,2-d][1,3]dioxine-6,7,8-triol (133 mg, 0.50 mmol, 1.5 equiv) and methanol (5 mL). The mixture was stirred for 30 min, then NaBH$_3$CN (41 mg, 0.65 mmol, 2.0 equiv) and AcOH (40 mg, 0.67 mmol, 2.00 equiv) were added. The resulting solution was stirred overnight at room temperature. The solvent was removed under reduced pressure to afford 210 mg (crude) of (9H-fluoren-9-yl)methyl (S)-3-(3,5-diamino-6-chloropyrazine-2-carboxamido)-2-(2-methylbenzyl)propyl((1-(4-((2S,3R)-2,3-dihydroxy-3-((2R,4R,5R)-5-hydroxy-2-phenyl-1,3-dioxan-4-yl)propylamino)butanoyl)piperidin-4-yl)methyl)carbamate as a yellow solid.

LC/MS: m/z 1005 [M+H]$^+$

Step 4:

(9H-fluoren-9-yl)methyl (S)-3-(3,5-diamino-6-chloropyrazine-2-carboxamido)-2-(2-methylbenzyl)propyl((1-(4-(((2S,3R)-2,3-dihydroxy-3-((2R,4R,5R)-5-hydroxy-2-phenyl-1,3-dioxan-4-yv)propyl)(hexyl)amino)butanoyl)piperidin-4-yl)methyl)carbamate

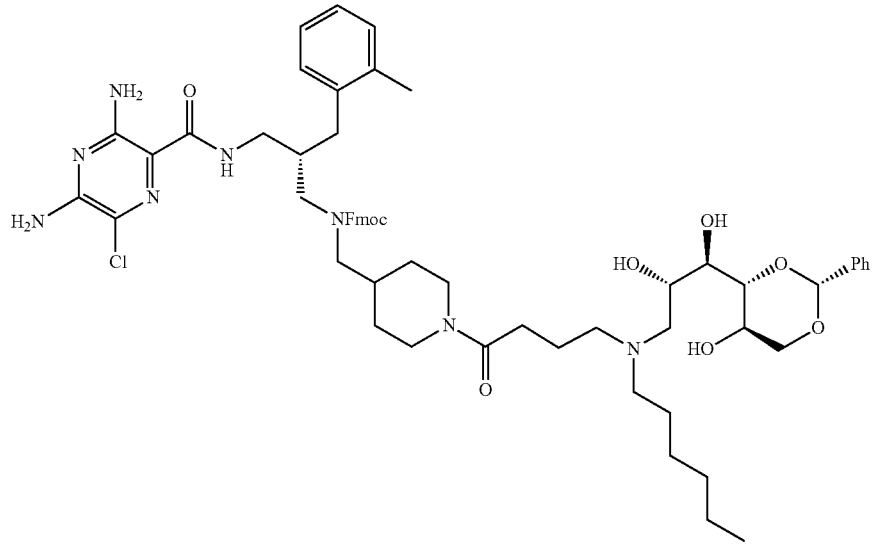

(9H-fluoren-9-yl)methyl (S)-3-(3,5-diamino-6-chloropyrazine-2-carboxamido)-2-(2-methylbenzyl)propyl((1-(4-(((2S,3R)-2,3-dihydroxy-3-((2R,4R,5R)-5-hydroxy-2-phenyl-1,3-dioxan-4-yl)propylamino)butanoyl)piperidin-4-yl)methyl)carbamate (210 mg, crude) was dissolved in MeOH (5 mL), hexanal (42 mg, 0.42 mmol, 2.00 equiv) was added, followed by NaBH$_3$CN (26 mg, 0.41 mmol, 2.00 equiv) and AcOH (25 mg, 0.42 mmol, 2.00 equiv). The resulting mixture was stirred for 2 h at room temperature and then concentrated under vacuum. The residue was taken up with water and extracted with 3×20 mL of ethyl acetate. The combined organic layers and concentrated under vacuum and resulted in 152 mg (67%) of the title compound as a crude yellow oil.

LC/MS: m/z 1089 [M+H]$^+$

Step 5:

(9H-fluoren-9-yl)methyl (S)-3-(3,5-diamino-6-chloropyrazine-2-carboxamido)-2-(2-methylbenzyl)propyl((1-(4-(hexyl((2S,3R,4R,5R)-2,3,4,5,6-pentahydroxyhexyl)amino)butanoyl)piperidin-4-yl)methyl) carbamate

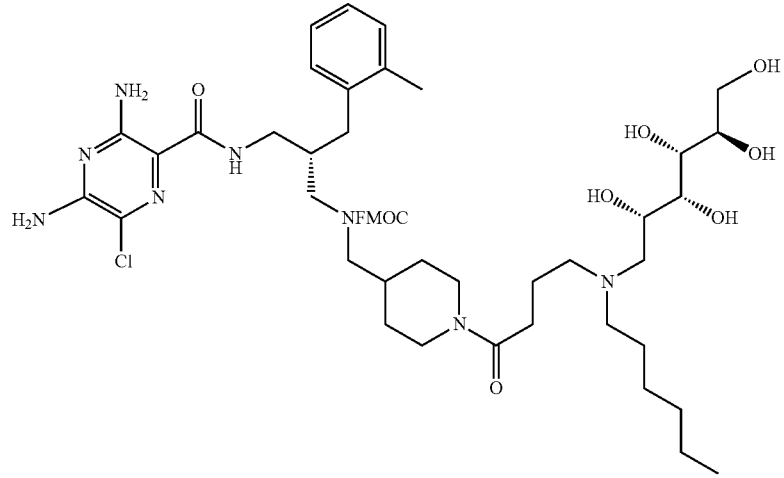

Into a 25-mL round-bottom flask was placed (9H-fluoren-9-yl)methyl (S)-3-(3,5-diamino-6-chloropyrazine-2-carboxamido)-2-(2-methylbenzyl)propyl((1-(4-(((2S,3R)-2,3-dihydroxy-3-((2R,4R,5R)-5-hydroxy-2-phenyl-1,3-dioxan-4-yl)propyl)(hexyl)amino)butanoyl)piperidin-4-yl)methyl) carbamate (step 4, 152 mg, 0.14 mmol, 1.00 equiv), HCl (4M in ethanol, 5 mL) and ethanol (1 mL). The resulting solution was stirred overnight at room temperature. Evaporation of the volatiles resulted in 138 mg of the crude title compound as yellow oil.

LC/MS: m/z 1002 [M+H]$^+$

Step 6:

3,5-diamino-6-chloro-N—((R)-3-((1-(4-(hexyl((2S,3R,4R,5R)-2,3,4,5,6-pentahydroxyhexyl)amino)butanoyl)piperidin-4-yl)methylamino)-2-(2-methylbenzyl)propyl)pyrazine-2-carboxamide

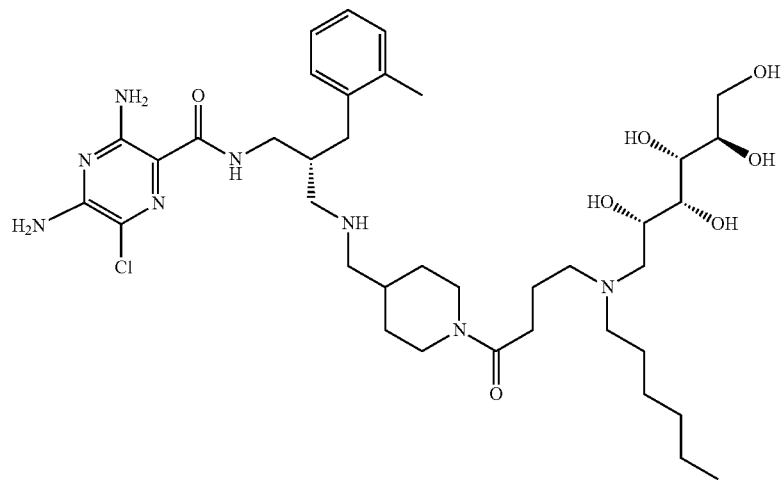 [SMILES: CCCCCCN(CCCC(=O)N1CCC(CNC[C@H](CNC(=O)c2nc(Cl)c(N)nc2N)Cc2ccccc2C)CC1)C[C@H](O)[C@@H](O)[C@H](O)[C@H](O)CO]

Into a 25-mL round-bottom flask, was placed (9H-fluoren-9-yl)methyl (S)-3-(3,5-diamino-6-chloropyrazine-2-carboxamido)-2-(2-methylbenzyl)propyl((1-(4-(hexyl((2S,3R,4R,5R)-2,3,4,5,6-pentahydroxyhexyl)amino)butanoyl)piperidin-4-yl)methyl)carbamate (step 4, 138 mg, 0.14 mmol, 1.0 equiv), diethylamine (2 mL), N,N-dimethylformamide (2 mL). The resulting solution was stirred for overnight at room temperature. The resulting mixture was concentrated under vacuum. The crude product (110 mg) was purified by preparative HPLC with the following conditions: Column, XSelect CSH Prep C18 OBD Column, 5 um, 19*150 mm; mobile phase, WATER WITH 0.05% TFA and MeCN (23% MeCN up to 30% in 8 min, up to 100% in 1 min, hold 100% in 1 min, down to 23.0% in 2 min); Detector, uv 254/220 nm. 15.7 mg (13%) of the title compound as trifluoroacetate was obtained as a yellow solid.

LC/MS: m/z 779.5 [M+H]+

$^1$H NMR (300 MHz, CD$_3$OD): 0.92-0.96 (m, 3H), 1.21-1.39 (m, 8H), 1.78-2.03 (m, 7H), 2.36 (s, 4H), 2.61-2.69 (m, 4H), 2.87-2.93 (m, 5H), 3.13-3.31 (m, 5H), 3.32-3.36 (m, 1H), 3.63-3.77 (s, 6H), 3.78-3.96 (m, 1H), 4.15-4.18 (m, 1H), 4.84-4.86 (m, 1H), 7.13-7.20 (m, 4H).

EXAMPLE 7

3,5-diamino-6-chloro-N—((R)-2-(2-methylbenzyl)-3-((1-(3-((2S,3R,4R,5R)-2,3,4,5,6-pentahydroxyhexylamino)propanoyl)piperidin-4-yl)methylamino)propyl)pyrazine-2-carboxamide

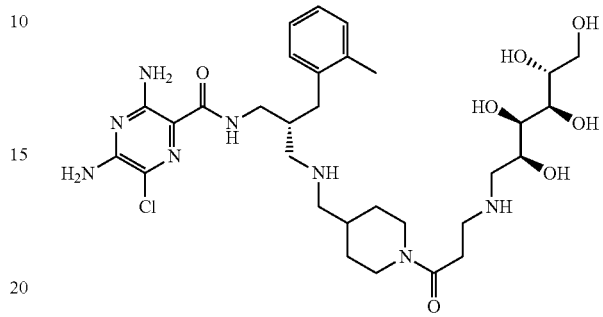

Step 1:

(9H-fluoren-9-yl)methyl (S)-3-(3,5-diamino-6-chloropyrazine-2-carboxamido)-2-(2-methylbenzyl)propyl((1-(3-((2S,3R)-2,3-dihydroxy-3-((2R,4R,5R)-5-hydroxy-2-phenyl-1,3-dioxan-4-yl)propylamino)propanoyl)piperidin-4-yl)methyl)carbamate

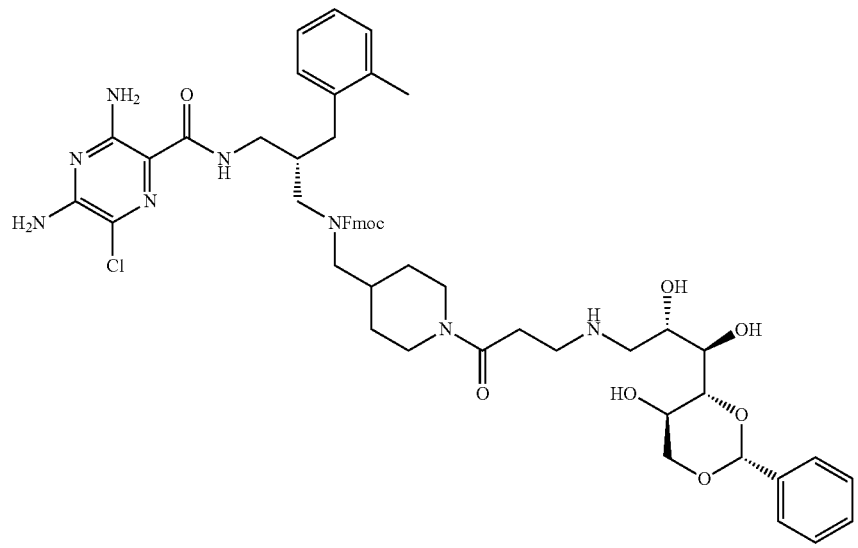

Into a 25-mL round-bottom flask was placed 3,5-diamino-6-chloro-N—((R)-3-((1-(3-(hexyl((2S,3R,4R)-2,3,4,5-tetrahydroxypentyl)amino)propanoyl)piperidin-4-yl)methylamino)-2-(2-methylbenzyl)propyl)pyrazine-2-carboxamide (Example 5/step 2, 20 mg, 0.27 mmol, 1.0 equiv) and the acetal protected D-glucose (2R,4aR,7R,8R,8aS)-2-phenylhexahydropyrano[3,2-d][1,3]dioxine-6,7,8-triol (218 mg, 0.81 mmol, 3.0 equiv) in methanol (5 mL). The resulting solution was stirred for 0.5 h at room temperature. NaBH$_3$CN (34 mg, 0.54 mmol, 2.0 equiv), AcOH (30 mg, 0.50 mmol, 2.0 equiv) was added. The resulting mixture was stirred overnight at room temperature. Quenching with water and extractive work up resulted after removal of the solvents in 220 mg of the crude title compound as a yellow solid.

LC/MS: m/z 992 [M+H]+

Step 2:

(9H-fluoren-9-yl)methyl (S)-3-(3,5-diamino-6-chloropyrazine-2-carboxamido)-2-(2-methylbenzyl)propyl((1-(3-((2S,3R,4R,5R)-2,3,4,5,6-pentahydroxyhexylamino)propanoyl)piperidin-4-yl)methyl)carbamate

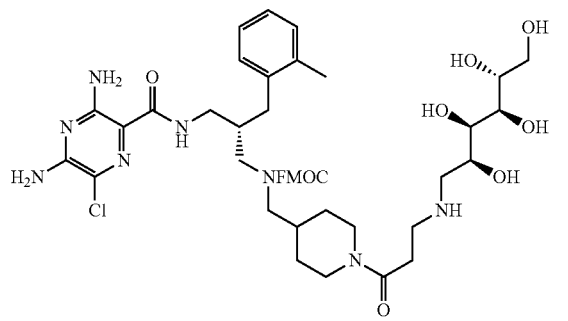

Into a 25-mL round-bottom flask, was placed (9H-fluoren-9-yl)methyl (S)-3-(3,5-diamino-6-chloropyrazine-2-carboxamido)-2-(2-methylbenzyl)propyl((1-(3-((2S,3R)-2,3-dihydroxy-3-((2R,4R,5R)-5-hydroxy-2-phenyl-1,3-dioxan-4-yl)propylamino)propanoyl)piperidin-4-yl)methyl)carbamate (step 1, 200 mg, 0.20 mmol, 1.0 equiv), ethanol (1.5 mL) and HCl (4M in ethanol, 5 mL). The resulting solution was stirred overnight at room temperature and then concentrated under vacuum. 180 mg of the crude title compound was obtained as a yellow solid.
LC/MS: m/z 904 [M+H]+

Step 3:

3,5-diamino-6-chloro-N—((R)-2-(2-methylbenzyl)-3-((1-(3-((2S,3R,4R,5R)-2,3,4,5,6-pentahydroxyhexylamino)propanoyl)piperidin-4-yl)methylamino)propyl)pyrazine-2-carboxamide

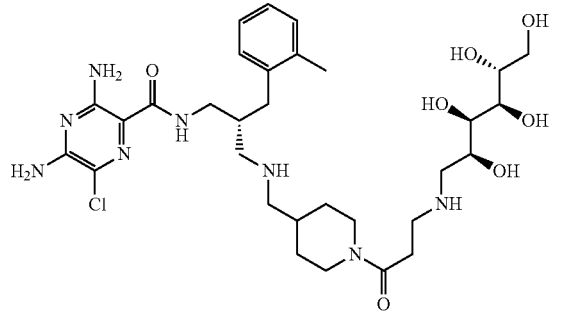 [SMILES: Cc1ccccc1C[C@H](CNCC1CCN(C(=O)CCNC[C@H](O)[C@@H](O)[C@H](O)[C@H](O)CO)CC1)CNC(=O)c1nc(Cl)c(N)nc1N]

Into a 25-mL round-bottom flask was placed 9H-fluoren-9-ylmethyl N-[(2S)-3-[(3,5-diamino-6-chloro-3,4-dihydropyrazin-2-yl)formamido]-2-[(2-methylphenyl)methyl]propyl]-N-[[1-(3-[[(2S,3R,4R,5R)-2,3,4,5,6-pentahydroxyhexyl]amino]propanoyl)piperidin-4-yl]methyl]carbamate (step 2, 180 mg, 0.20 mmol, 1.0 equiv), a diethylamine (2 mL) and N,N-dimethylformamide (4 mL). The resulting solution was stirred for 4 h at room temperature and after there was concentrated under vacuum. The crude product (150 mg) was purified by preparative HPLC using the following conditions: Column, XBridge Prep C18 OBD Column, 5 um, 19*150 mm; mobile phase, water with 0.05% TFA and ACN (16.0% ACN up to 26.0% in 15 min); Detector, MS, UV 254/220 nm. This resulted in 15.5 mg (10%) of the trifluoroacetate of the title compound as a yellow solid.
LC/MS: m/z 681.4 [M+H]+
1H NMR (300 MHz, CD3OD): 1.12-1.43 (m, 2H), 1.87-2.12 (m, 3H), 2.14 (s, 4H), 2.62-2.75 (m, 2H), 2.87-2.93 (m, 7H), 3.01-3.19 (m, 3H), 3.31-3.37 (m, 1H), 3.77-3.80 (m, 5H), 3.87-3.95 (m, 2H), 4.07-4.58 (s, 1H), 4.80-4.96 (d, 1H), 7.13-7.20 (m, 4H).

EXAMPLE 8

3,5-diamino-6-chloro-N—((R)-3-((1-(3-(hexyl((2R,3R,4R,5R)-2,3,4,5,6-pentahydroxyhexyl)amino)propanoyl)piperidin-4-yl)methylamino)-2-(2-methylbenzyl)propyl)pyrazine-2-carboxamide

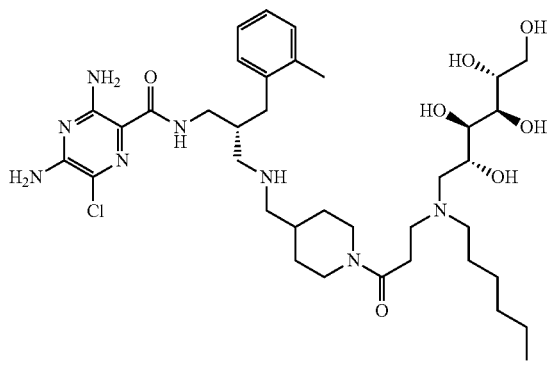

Step 1:

(9H-fluoren-9-yl)methyl (S)-3-(3,5-diamino-6-chloropyrazine-2-carboxamido)-2-(2-methylbenzyl)propyl((1-(3-(((2R,3R)-2,3-dihydroxy-3-((2R,4R,5R)-5-hydroxy-2-phenyl-1,3-dioxan-4-yl)propyl)(hexyl)amino)propanoyl)piperidin-4-yl)methyl)carbamate

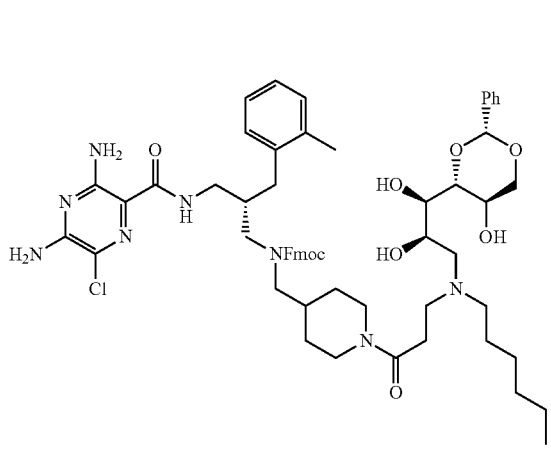

Sodium cyanoborohydride (57.0 mg, 0.91 mmol) was added portionwise to a mixture of hexanal (45.5 mg, 0.45 mmol) and (9H-fluoren-9-yl)methyl ((S)-3-(3,5-diamino-6-chloropyrazine-2-carboxamido)-2-(2-methylbenzyl)propyl) ((1-(3-(((2R,3R)-2,3-dihydroxy-3-((2R,4R,5R)-5-hydroxy- 2-phenyl-1,3-dioxan-4-yl)propyl)amino)propanoyl) piperidin-4-yl)methyl)carbamate [prepared by an analogue procedure as described for Example 7/step 1; starting instead from the acetal protected D-mannitol (2R,4aR,7S,8R,8aS)-2-phenylhexahydropyrano[3,2-d][1,3]dioxine-6,7,8-triol] (300 mg, 0.30 mmol) in MeOH (20 mL). The resulting solution was stirred at 25° C. for 4 h. The solvent was removed under reduced pressure. The residue was purified by preparative TLC (DCM:MeOH=25:1) to afford (9H-fluoren-9-yl)methyl ((S)-3-(3,5-diamino-6-chloropyrazine-2-carboxamido)-2-(2-methylbenzyl)propyl)((1-(3-(((2R,3R)-2,3-dihydroxy-3-((2R,4R,5R)-5-hydroxy-2-phenyl-1,3-dioxan-4-yl)propyl)(hexyl)amino)propanoyl)piperidin-4-yl)methyl)carbamate (270 mg, 83%) as a yellow gum.

LC/MS: m/z 1076 [M+H]+

$^1$H NMR (300 MHz, CD$_3$OD): δ 0.89-1.19 (m, 8H), 1.23-1.37 (m, 11H), 1.59-1.65 (m, 4H), 2.16-2.21 (m, 6H), 2.62-3.04 (m, 14H), 3.34-3.68 (m, 2H), 3.87-3.96 (m, 4H), 4.11-4.27 (m, 4H), 4.70-4.80 (m, 2H), 5.57 (s, 1H), 7.07-7.29 (m, 4H), 7.31-7.50 (m, 7H), 7.50-7.53 (m, 4H), 7.78 (d, 2H).

Step 2:

(9H-fluoren-9-yl)methyl (S)-3-(3,5-diamino-6-chloropyrazine-2-carboxamido)-2-(2-methylbenzyl)propyl((1-(3-(hexyl((2R,3R,4R,5R)-2,3,4,5,6-pentahydroxyhexyl)amino)propanoyl)piperidin-4-yl)methyl) carbamate

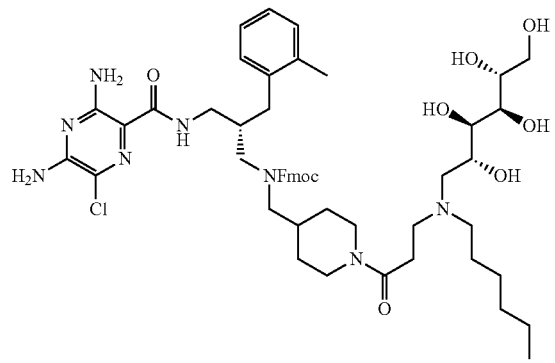

(9H-fluoren-9-yl)methyl ((S)-3-(3,5-diamino-6-chloropyrazine-2-carboxamido)-2-(2-methylbenzyl)propyl)((1-(3-(((2R,3R)-2,3-dihydroxy-3-((2R,4R,5R)-5-hydroxy-2-phenyl-1,3-dioxan-4-yl)propyl)(hexyl)amino)propanoyl)piperidin-4-yl)methyl)carbamate (270 mg, 0.25 mmol) was added to HCl (4M, aq., 15 mL) in ethanol (5 mL). After stirring at 25° C. for 2 h the mixture was concentrated under reduced pressure and afforded the title compound (200 mg, 81%) as a yellow oil.

LC/MS: m/z 987 [M+H]+

Step 3:

3,5-diamino-6-chloro-N—((R)-3-((1-(3-(hexyl((2R,3R,4R,5R)-2,3,4,5,6-pentahydroxyhexyl)amino)propanoyl)piperidin-4-yl)methylamino)-2-(2-methylbenzyl)propyl)pyrazine-2-carboxamide

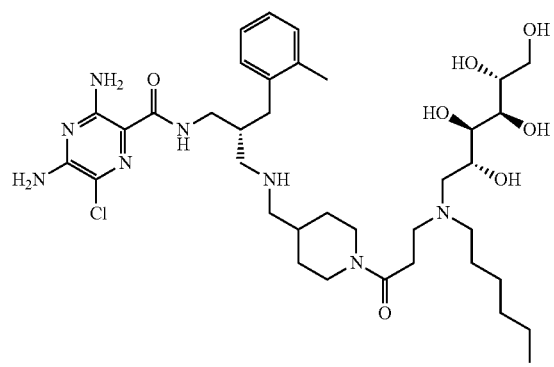

Diethylamine (3 mL) was added to (9H-fluoren-9-yl)methyl ((S)-3-(3,5-diamino-6-chloropyrazine-2-carboxamido)-2-(2-methylbenzyl)propyl)((1-(3-(hexyl((2R,3R,4R,5R)-2,3,4,5,6-pentahydroxyhexyl)amino)propanoyl) piperidin-4-yl)methyl)carbamate (step 2, 200 mg, 0.20 mmol) in DMF (6 mL). The resulting mixture was stirred at 25° C. for 2 hours. The solvent was removed under reduced pressure. The crude product was purified by preparative HPLC Column: X Bridge C18, 19*150 mm, 5 um; Mobile Phase A: Water/0.05% TFA, Mobile Phase B: ACN; Flow rate: 20 mL/min; Gradient: 30% B to 70% B in 10 min; 254 nm, as eluents. Fractions containing the desired compound were evaporated to dryness to afford 3,5-diamino-6-chloro-N—((R)-3-(((1-(3-(hexyl((2R,3R,4R,5R)-2,3,4,5,6-pentahydroxyhexyl)amino)propanoyl)piperidin-4-yl)methyl)amino)-2-(2-methylbenzyl)propyl)pyrazine-2-carboxamide (23.5 mg) as a yellow gum.

LC/MS: m/z 765.4 [M+H]+

$^1$H NMR (300 MHz, CD$_3$OD): δ 0.94 (t, 3H), 1.29-1.40 (m, 8H), 1.80-2.04 (m, 5H), 2.35 (s, 3H), 2.35 (m, 1H), 2.62-2.71 (m, 2H), 2.85-2.97 (m, 7H), 3.15-3.30 (m, 4H), 3.31-3.69 (m, 4H), 3.71-3.83 (m, 6H), 4.03-4.06 (m, 2H), 4.86-4.87 (m, 1H), 7.13-7.20 (m, 1H).

EXAMPLE 9

3,5-diamino-6-chloro-N—((R)-3-((4-((2-(hexyl((2R, 3R,4R,5R)-2,3,4,5,6-pentahydroxyhexyl)amino) ethyl)carbamoyl)benzyl)amino)-2-(2-methylbenzyl) propyl)pyrazine-2-carboxamide Dihydrochloride

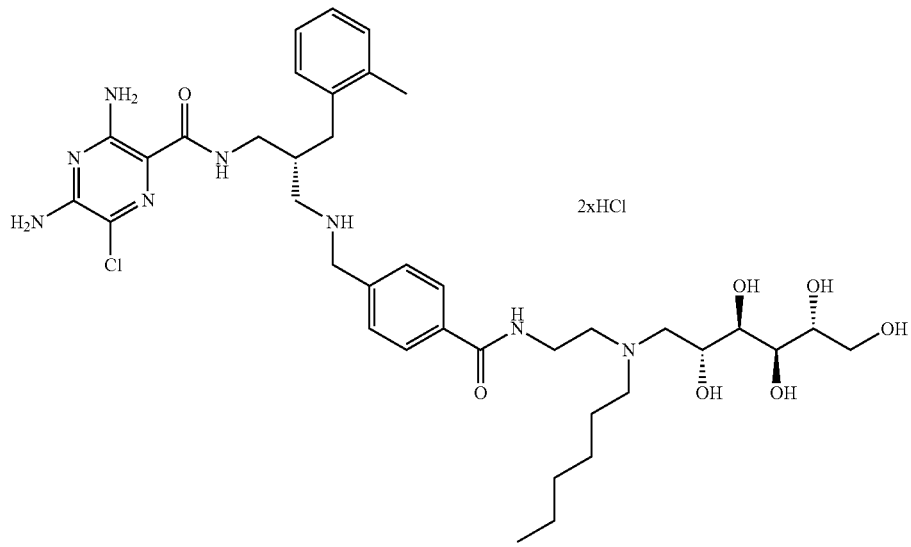 [SMILES: CCCCCCN(CCNC(=O)c1ccc(CNC[C@H](CNC(=O)c2nc(Cl)c(N)nc2N)Cc2ccccc2C)cc1)C[C@@H](O)[C@@H](O)[C@H](O)[C@H](O)CO]

Step 1

Tert-butyl ((S)-3-(3,5-diamino-6-chloropyrazine-2-carboxamido)-2-(2-methylbenzyl)propyl)(4-((2-(hexyl((2R,3R,4R,5R)-2,3,4,5,6-pentahydroxyhexyl)amino)ethyl)carbamoyl)benzyl)carbamate

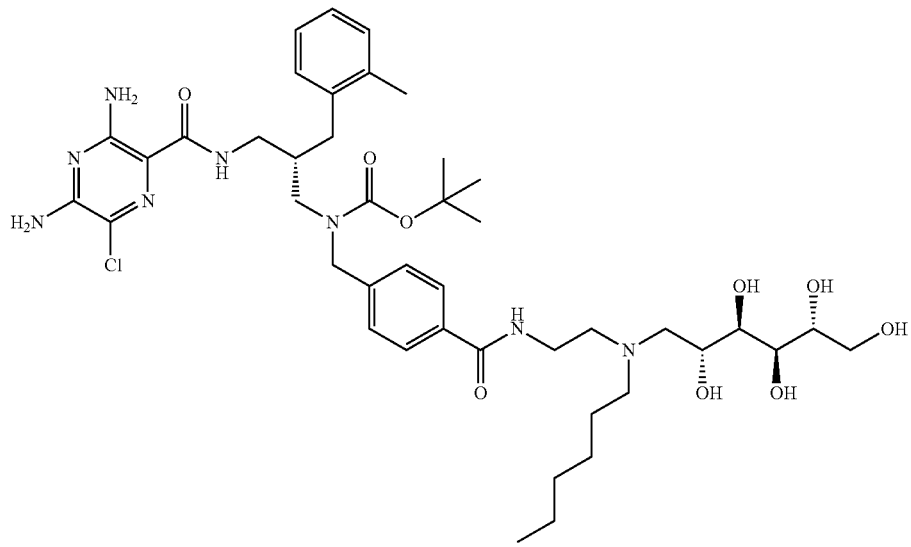 [SMILES: CCCCCCN(CCNC(=O)c1ccc(CN(C[C@H](CNC(=O)c2nc(Cl)c(N)nc2N)Cc2ccccc2C)C(=O)OC(C)(C)C)cc1)C[C@@H](O)[C@@H](O)[C@H](O)[C@H](O)CO]

(S)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate (Intermediate E, 500 mg, 0.70 mmol), (3S,4S,5S,6R)-6-(hydroxymethyl)tetrahydro-2H-pyran-2,3,4,5-tetraol (254 mg, 1.41 mmol) and DIPEA (0.123 mL, 0.70 mmol) were dissolved in MeOH (10 mL) and stirred at room temperature for 1 h. Sodium cyanoborohydride (133 mg, 2.11 mmol) and acetic acid (0.040 mL, 0.70 mmol) were added and stirring continued for 18 h and then at 50° C. for 30 h. The reaction was cooled to room temperature, quenched by addition of 3 M HCl (aq), stirred for 15 min and was then concentrated in vacuo. The residue was dissolved in EtOAc (50 mL) and 8% NaHCO$_3$ (aq) (50 mL), shaken and the phases separated. The aqueous phase was extracted with EtOAc (3×50 mL). The combined organic phases were dried with Na2SO4 (s), filtered and evaporated in vacuo. The compound was purified by preparative HPLC on a Kromasil C8 column (10 μm 250×50 ID mm) using a gradient of 20-60% acetonitrile in H2O/MeCN/AcOH 95/5/0.2 buffer over 20 minutes with a flow of 100 mL/min. The compounds were detected by UV at 268 nm.

The compound was collected and freeze-dried to yield the title compound (195 mg, 32%) as a colorless solid.

LC/MS: m/z 873.6 [M+H]+

1H NMR (500 MHz, DMSO-d6) δ 0.76-0.85 (m, 3H), 1.13-1.27 (m, 6H), 1.3-1.44 (m, 11H), 2.21 (s, 3H), 2.24-2.38 (m, 1H), 2.39-2.53 (m, 4H), 2.57-2.66 (m, 2H), 2.77 (d, 1H), 2.91-3.06 (m, 1H), 3.06-3.41 (m, 8H), 3.43-3.49 (m, 1H), 3.51 (d, 1H), 3.55-3.65 (m, 3H), 4.23-4.55 (m, 5H), 6.97 (bs, 2H), 7.04-7.18 (m, 6H), 7.72 (d, 2H), 7.78-7.99 (m, 1H), 8.27-8.37 (m, 1H).

Step 2

3,5-diamino-6-chloro-N—((R)-3-((4-((2-(hexyl((2R,3R,4R,5R)-2,3,4,5,6-pentahydroxyhexyl)amino)ethyl)carbamoyl)benzyl)amino)-2-(2-methylbenzyl)propyl)pyrazine-2-carboxamide Dihydrochloride

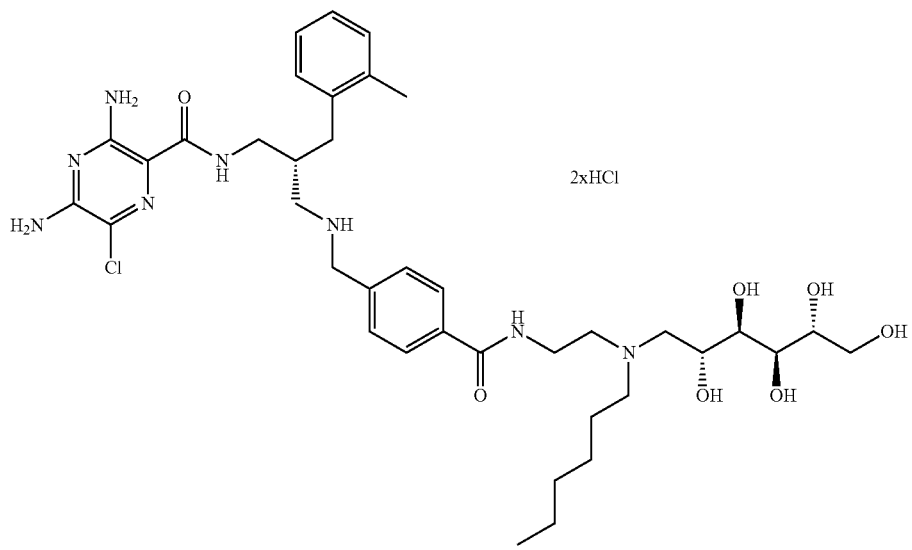 [SMILES: CCCCCCN(CCNC(=O)c1ccc(CNC[C@H](CNC(=O)c2nc(Cl)c(N)nc2N)Cc2ccccc2C)cc1)C[C@@H](O)[C@@H](O)[C@H](O)[C@H](O)CO]

To an icebath cooled vial of MeOH (5 mL, 124 mmol) was added acetyl chloride (1.42 mL, 20 mmol) dropwise. The mixture was stirred for 5 min and tert-butyl ((S)-3-(3,5-diamino-6-chloropyrazine-2-carboxamido)-2-(2-methylbenzyl)propyl)(4-((2-(hexyl((2R,3R,4R,5R)-2,3,4,5,6-pentahydroxyhexyl)amino)ethyl)carbamoyl)benzyl)carbamate (190 mg, 0.22 mmol) was then added. The reaction was stirred at room temperature for 1.5 h and was then evaporated in vacuo. The residue was dissolved in water and freeze-dried to yield the title compound (184 mg, 100%) as a pale solid.

LC/MS: m/z 773.4 [M+H]+

1H NMR (500 MHz, DMSO-d6) δ 0.81-0.89 (m, 3H), 1.2-1.33 (m, 6H), 1.62-1.77 (m, 2H), 2.26 (s, 3H), 2.3-2.41 (m, 1H), 2.6-2.73 (m, 2H), 2.75-2.84 (m, 1H), 2.86-2.97 (m, 1H), 3.11-3.27 (m, 3H), 3.27-3.45 (m, 5H), 3.45-3.52 (m, 2H), 3.52-3.76 (m, 5H), 3.89-3.99 (m, 1H), 4.03-4.48 (m, 7H), 6.88-7.23 (m, 6H), 7.63 (d, 2H), 7.93 (d, 2H), 8.26 (t, 1H), 8.93-9.02 (m, 1H), 9.13-9.34 (m, 2H), 9.55 (bs, 1H).

EXAMPLE 10

3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide

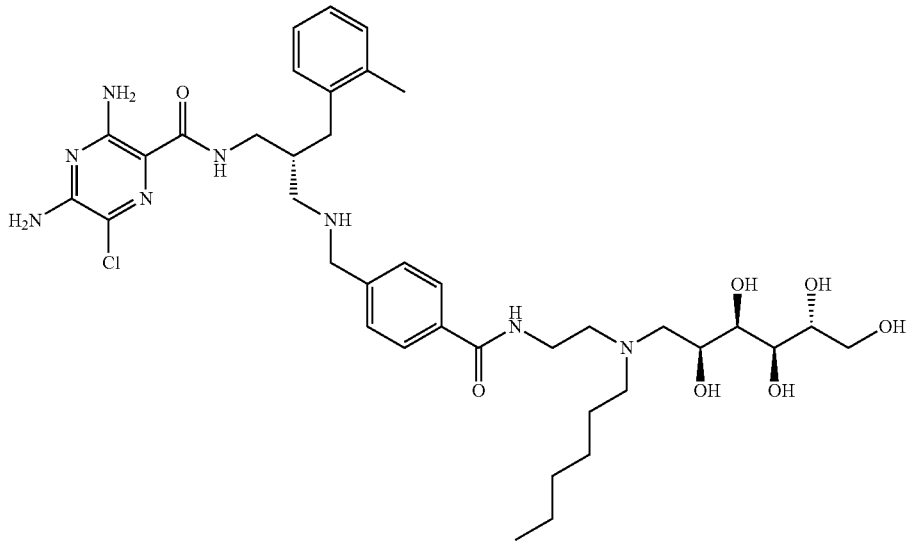 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)[C@H](O)CO]

Step 1 tert-butyl ((S)-3-(3,5-diamino-6-chloropyrazine-2-carboxamido)-2-(2-methylbenzyl)propyl)(4-((2-(hexyl((2S,3R,4R,5R)-2,3,4,5,6-pentahydroxyhexyl)amino)ethyl)carbamoyl)benzyl)carbamate

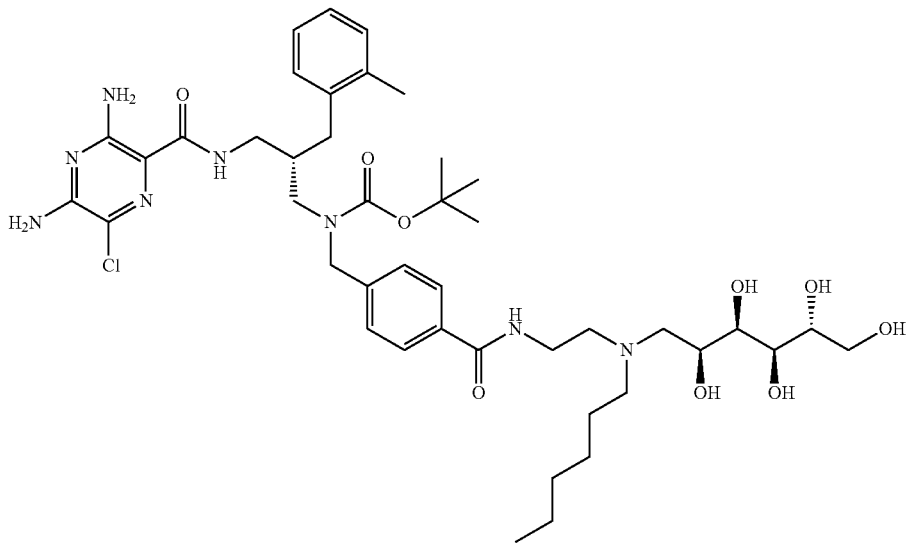 [SMILES: CCCCCCN(CCNC(=O)c1ccc(CN(C[C@H](CNC(=O)c2nc(Cl)c(N)nc2N)Cc2ccccc2C)C(=O)OC(C)(C)C)cc1)C[C@H](O)[C@@H](O)[C@H](O)[C@H](O)CO]

(S)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate (Intermediate E, 1.25 g, 1.76 mmol), (3R,4S,5S,6R)-6-(hydroxymethyl)tetrahydro-2H-pyran-2,3,4,5-tetraol (0.635 g, 3.52 mmol) and DIPEA (0.308 mL, 1.76 mmol) were dissolved in MeOH (10 mL) and stirred at room temperature for 1 h. Sodium cyanoborohydride (0.332 g, 5.29 mmol) and acetic acid (0.101 mL, 1.76 mmol) were added and stirring continued for 40 h at 50° C. The reaction was cooled to room temperature, quenched by addition of 8% NaHCO3 (aq), stirred for 30 min and concentrated in vacuo. The residue was dissolved in EtOAc (100 mL) and 8% NaHCO$_3$ (aq) (100 mL), shaken and the phases separated. The aqueous phase was extracted with EtOAc (2×100 mL). The combined organic phases were dried with Na$_2$SO$_4$ (s), filtered and evaporated in vacuo. The compound was purified by preparative HPLC on a Kromasil C8 column (10 μm 250×50 ID mm) using a gradient of 20-60% acetonitrile in H2O/MeCN/AcOH 95/5/0.2 buffer over 20 minutes with a flow of 100 mL/min. The compounds were detected by UV at 268 nm. The compound was collected and freeze-dried to yield tert-butyl ((S)-3-(3,5-diamino-6-chloropyrazine-2-carboxamido)-2-(2-methylbenzyl)propyl)(4-((2-(hexyl((2S,3R,4R,5R)-2,3,4,5,6-pentahydroxyhexyl)amino)ethyl)carbamoyl)benzyl)carbamate (1.26 g, 82%) as a white solid.

LC/MS: m/z 873.6 [M+H]$^+$

1H NMR (500 MHz, DMSO-d6) δ 0.73-0.86 (m, 3H), 1.1-1.27 (m, 6H), 1.27-1.46 (m, 11H), 2.20 (s, 3H), 2.24-2.38 (m, 1H), 2.38-2.49 (m, 3H), 2.53-2.69 (m, 3H), 2.9-3.06 (m, 1H), 3.06-3.47 (m, 10H), 3.47-3.54 (m, 1H), 3.54-3.76 (m, 3H), 4.18-4.65 (m, 6H), 6.97 (bs, 2H), 7.03-7.19 (m, 6H), 7.72 (d, 2H), 7.78-8 (m, 1H), 8.24-8.37 (m, 1H).

Step 2

3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide Dihydrochloride

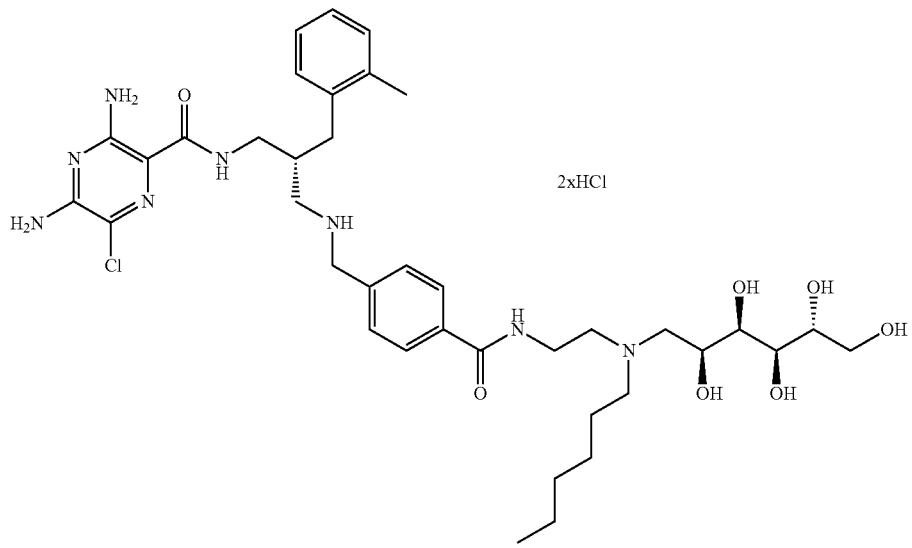 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)[C@H](O)CO]

Acetyl chloride (5.69 mL, 80.0 mmol) was added dropwise to an icebath cooled flask of MeOH (20 mL). The mixture was stirred for 5 min and tert-butyl ((S)-3-(3,5-diamino-6-chloropyrazine-2-carboxamido)-2-(2-methylbenzyl)propyl)(4-((2-(hexyl((2S,3R,4R,5R)-2,3,4,5,6-pentahydroxyhexyl)amino)ethyl)carbamoyl)benzyl)carbamate (1.26 g, 1.44 mmol) was then added. The reaction was stirred at room temperature for 1.5 h and was then evaporated in vacuo. The residue was dissolved in water and freeze-dried to yield 3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide dihydrochloride (1.29 g, 106%) as a pale solid.

LC/MS: m/z 773.4 [M+H]$^+$ $^1$H NMR (500 MHz, DMSO-d$_6$) δ 0.78-0.89 (m, 3H), 1.18-1.32 (m, 6H), 1.62-1.76 (m, 2H), 2.26 (s, 3H), 2.33-2.44 (m, 1H), 2.67 (d, 2H), 2.73-2.84 (m, 1H), 2.84-2.96 (m, 1H), 3.1-3.44 (m, 9H), 3.44-3.54 (m, 2H), 3.55-3.62 (m, 1H), 3.62-3.75 (m, 3H), 4.02-4.12 (m, 1H), 4.12-4.3 (m, 2H), 5.58 (bs, 5H), 6.91-7.21 (m, 6H), 7.64 (d, 2H), 7.94 (d, 2H), 8.25 (t, 1H), 8.97-9.06 (m, 1H), 9.28 (bs, 1H), 9.41 (bs, 1H), 9.70 (d, 1H).

Step 3

3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide

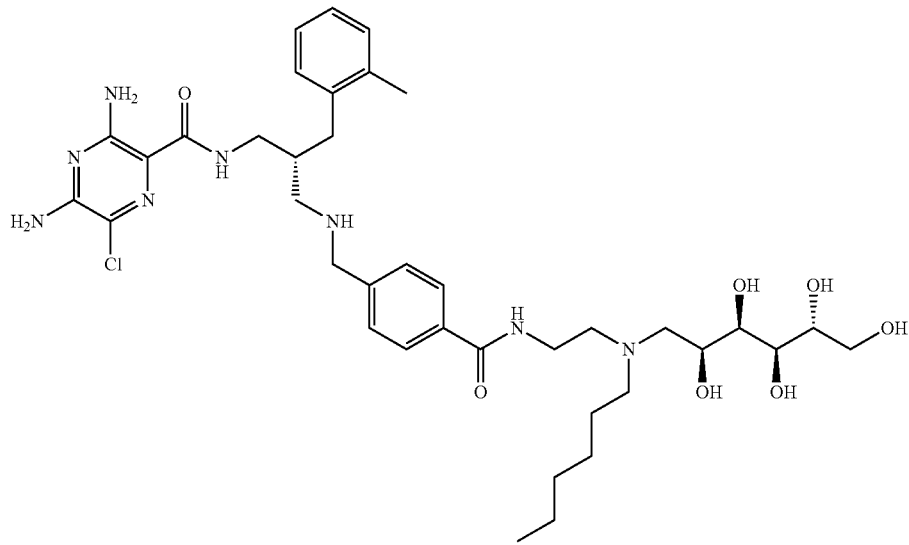 [SMILES: CCCCCCN(CCNC(=O)c1ccc(CNC[C@H](CNC(=O)c2nc(Cl)c(N)nc2N)Cc2ccccc2C)cc1)C[C@H](O)[C@@H](O)[C@H](O)[C@H](O)CO]

3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide dihydrochloride (1.23 g, 1.45 mmol) was dissolved in water (15 ml) and basified by addition of 10% Na2CO3 (aq) to pH ~11. The product was extracted with EtOAc (6×70 mL). The combined organic phases were dried with $Na_2SO_4$ (s), filtered and evaporated in vacuo to yield a semi solid/oil. The residue was dissolved in acetonitrile/water and freeze-dried to yield 3,5-diamino-6-chloro-N—((R)-3-((4-((2-(hexyl((2S,3R,4R,5R)-2,3,4,5,6-pentahydroxyhexyl)amino)ethyl)carbamoyl)benzyl)amino)-2-(2-methylbenzyl)propyl)pyrazine-2-carboxamide (1.08 g, 96%) as a pale solid.

LC/MS: m/z 773.4 [M+H]$^+$

1H NMR (500 MHz, DMSO-d6) δ 0.75-0.84 (m, 3H), 1.13-1.26 (m, 6H), 1.32-1.42 (m, 2H), 1.94-2.05 (m, 1H), 2.24 (s, 3H), 2.34-2.49 (m, 6H), 2.54-2.66 (m, 4H), 3.14-3.23 (m, 1H), 3.25-3.35 (m, 4H), 3.35-3.42 (m, 1H), 3.42-3.47 (m, 1H), 3.47-3.54 (m, 1H), 3.55-3.61 (m, 1H), 3.61-3.77 (m, 4H), 4.26-4.33 (m, 2H), 4.47 (d, 1H), 4.51 (d, 2H), 6.96 (bs, 2H), 7.04-7.14 (m, 4H), 7.40 (d, 2H), 7.74 (d, 2H), 8.26-8.37 (m, 2H).

EXAMPLE 11

4-(((R)-3-(3,5-diamino-6-chloropyrazine-2-carboxamido)-2-(2-methylbenzyl)propylamino)methyl)phenyl 2-(hexyl((2S,3R,4R,5R)-2,3,4,5,6-pentahydroxyhexyl)amino)ethylcarbamate

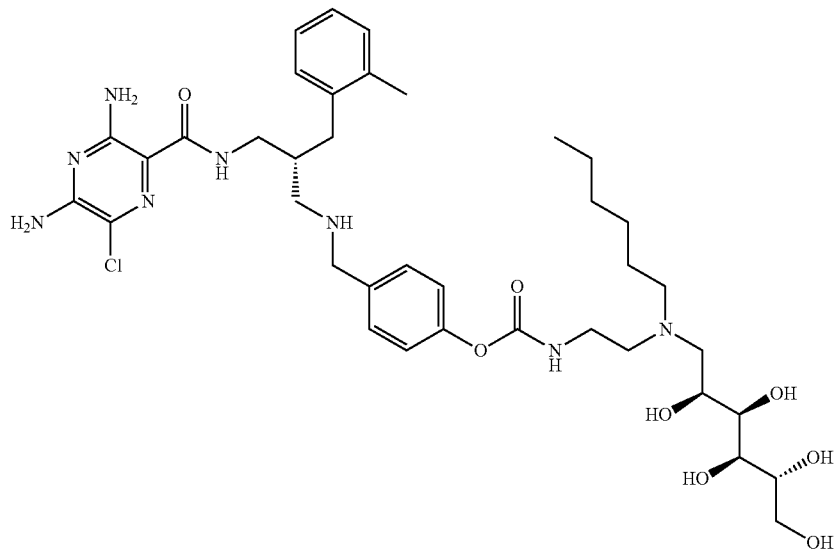 [SMILES: CCCCCCN(CCNC(=O)Oc1ccc(CNC[C@H](CNC(=O)c2nc(Cl)c(N)nc2N)Cc2ccccc2C)cc1)C[C@H](O)[C@@H](O)[C@H](O)[C@H](O)CO]

Step 1:

(R)-4-((3-(3,5-diamino-6-chloropyrazine-2-carboxamido)-2-(2-methylbenzyl)propylamino)methyl)phenyl Acetate

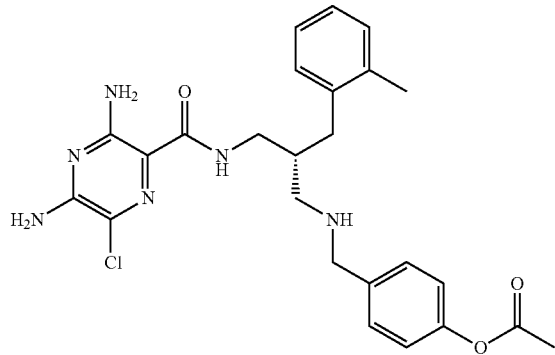 [SMILES: CC(=O)Oc1ccc(CNC[C@H](CNC(=O)c2nc(Cl)c(N)nc2N)Cc2ccccc2C)cc1]

In a 50 mL pear flask was (R)-3,5-diamino-N-(3-amino-2-(2-methylbenzyl)propyl)-6-chloropyrazine-2-carboxamide (Intermediate A, 1.6 g, 4.59 mmol) and 4-formylphenyl acetate (0.753 g, 4.59 mmol) added to DCM (30 mL) to give a yellow solution. After stirring for 1 h sodium triacetoxyborohydride (3.89 g, 18.4 mmol) was added and stirring was continued overnight. The mixture was diluted with DCM and washed with water and brine. The organic layer was dried over Na$_2$SO$_4$, filtered and evaporated in vacuo to afford crude (R)-4-(((3-(3,5-diamino-6-chloropyrazine-2-carboxamido)-2-(2-methylbenzyl)propyl)amino)methyl)phenyl acetate (1.70 g, 75%) as a yellow solid. The product was used in the next step directly without further purification.

LC/MS: m/z 467 [M+H]$^+$

Step 2:

(S)-4-((tert-butoxycarbonyl(3-(3,5-diamino-6-chloropyrazine-2-carboxamido)-2-(2-methylbenzyl)propyl)amino)methyl)phenyl Acetate

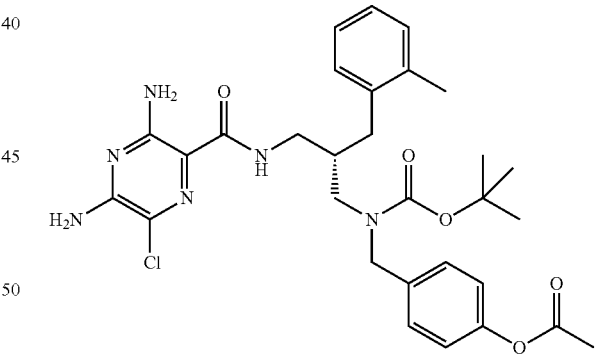

(BOC)$_2$O (1.07 mL, 4.59 mmol) was added to a mixture of (R)-4-(((3-(3,5-diamino-6-chloropyrazine-2-carboxamido)-2-(2-methylbenzyl)propyl)amino)methyl)phenyl acetate (1.9 g, 3.82 mmol) and Na$_2$CO$_3$ (0.81 g, 7.65 mmol) in the mixture solvents dioxane (25 mL)/water (8 mL) at 0° C. The mixture was allowed to reach room temperature and stirred overnight. The reaction mixture was diluted with EtOAc, and washed with saturated brine. The organic layer was dried over Na$_2$SO$_4$, filtered and evaporated in vacuo. The residue was purified by flash chromatography on silica gel using a gradient of 10 to 40% EtOAc in petroleum ether. Pure fractions were evaporated to dryness to afford the title compound (1.30 g, 57%) as a yellow solid.

LC/MS: m/z 597 [M+H]$^+$

¹H NMR (300 MHz, CD₃OD): δ 1.47 (s, 9H), 2.25-2.2.51 (m, 7H), 2.54-2.65 (m, 2H), 3.05-3.22 (m, 2H), 3.31-3.39 (m, 2H), 4.13-4.45 (m, 2H), 6.93-7.00 (m, 2H), 7.06-7.10 (m, 6H).

Step 3:

(S)-tert-butyl 3-(3,5-diamino-6-chloropyrazine-2-carboxamido)-2-(2-methylbenzyl)propyl(4-hydroxybenzyl)carbamate

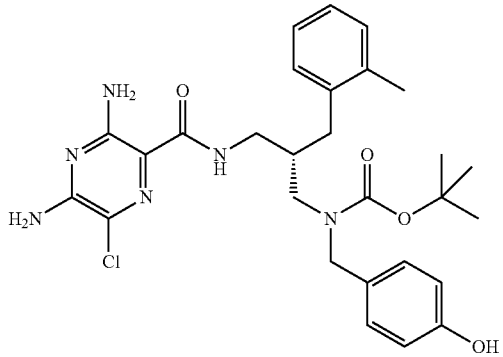 [SMILES: Cc1ccccc1C[C@@H](CNC(=O)c1nc(Cl)c(N)nc1N)CN(Cc1ccc(O)cc1)C(=O)OC(C)(C)C]

NaOH (0.174 g, 4.35 mmol) in water (8 mL) was added dropwise to a cooled solution of (S)-4-(((tert-butoxycarbonyl)(3-(3,5-diamino-6-chloropyrazine-2-carboxamido)-2-(2-methylbenzyl)propyl)amino)methyl)phenyl acetate (1.3 g, 2.18 mmol) in MeOH (20 mL). The reaction solution was stirred for 3 hours at room temperature. The reaction mixture was acidified with 2M aq. HCl. The reaction mixture was extracted with EtOAc and the organic phase was washed with water and brine, dried over Na₂SO₄, filtered and evaporated to afford the crude title compound (1.20 g, 99%) as yellow solid.

LC/MS: m/z 555 [M+H]⁺

Step 4:

(S)-4-((tert-butoxycarbonyl(3-(3,5-diamino-6-chloropyrazine-2-carboxamido)-2-(2-methylbenzyl)propyl)amino)methyl)phenyl Carbonochloridate

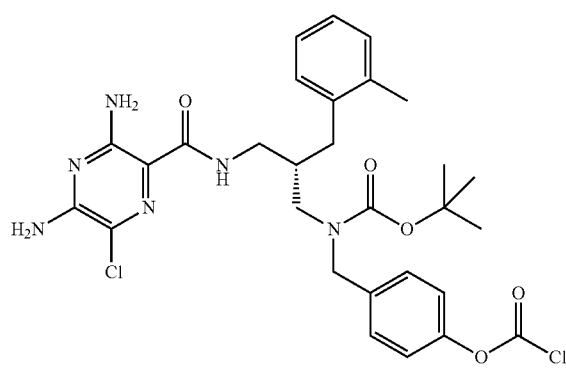 [SMILES: Cc1ccccc1C[C@@H](CNC(=O)c1nc(Cl)c(N)nc1N)CN(Cc1ccc(OC(=O)Cl)cc1)C(=O)OC(C)(C)C]

In a 50 mL round-bottomed flask was added (S)-tert-butyl (3-(3,5-diamino-6-chloropyrazine-2-carboxamido)-2-(2-methylbenzyl)propyl)(4-hydroxybenzyl)carbamate (250 mg, 0.45 mmol), DIEA (0.354 mL, 2.03 mmol) to THF (10 mL) to give a yellow solution. The mixture was cooled with an ice bath and triphosgene (200 mg, 0.68 mmol) was added. After stirring for 1 h the reaction mixture was poured into water and extracted with EtOAc (3×20 mL). The organic layer was dried over Na₂SO₄, filtered and evaporated to afford the title compound (250 mg, 90%) as yellow oil.

LC/MS: m/z 617 [M+H]⁺

Step 5:

tert-butyl ((S)-3-(3,5-diamino-6-chloropyrazine-2-carboxamido)-2-(2-methylbenzyl)propyl)(4-(((2-(((2S,3R)-2,3-dihydroxy-3-((2R,4R,5R)-5-hydroxy-2-phenyl-1,3-dioxan-4-yl)propyl)(hexyl)amino)ethyl)carbamoyl)oxy)benzyl)carbamate

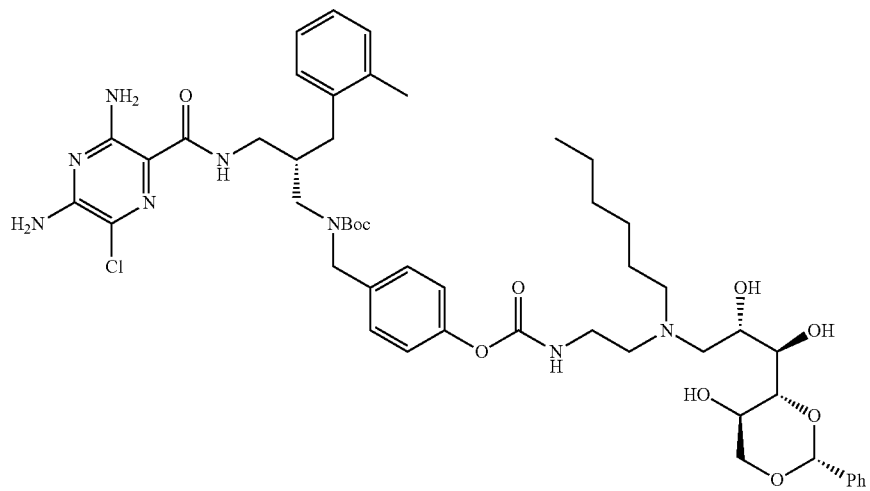 [SMILES: CCCCCCN(CCNC(=O)Oc1ccc(CN(C[C@H](CNC(=O)c2nc(Cl)c(N)nc2N)Cc2ccccc2C)C(=O)OC(C)(C)C)cc1)C[C@H](O)[C@@H](O)[C@@H]1O[C@H](c2ccccc2)OC[C@H]1O]

In a 50 mL round-bottomed flask was (1R,2S)-3-((2-aminoethyl)(hexyl)amino)-1-((2R,4R,5R)-5-hydroxy-2-phenyl-1,3-dioxan-4-yl)propane-1,2-diol (Example 3/step 2, 96 mg, 0.24 mmol) and DIEA (0.064 mL, 0.36 mmol) dissolved in THF (10 mL) resulting in a colorless solution. (S)-4-(((tert-butoxycarbonyl)(3-(3,5-diamino-6-chloropyrazine-2-carboxamido)-2-(2-methylbenzyl)propyl)amino)methyl)phenyl carbonochloridate (step 4, 150 mg, 0.24 mmol) was added at 0° C. The resulting solution was stirred at room temperature for 3 h. The reaction mixture was poured into water (20 mL) and extracted with EtOAc (3×20 mL). The organic phases were dried over Na$_2$SO$_4$, filtered and evaporated in vacuo. The residue was purified by preparative TLC (DCM:MeOH=10:1), to afford the title compound (200 mg, 84%) as a yellow solid.

LC/MS: m/z 977 [M+H]$^+$

Step 6:

4-(((R)-3-(3,5-diamino-6-chloropyrazine-2-carboxamido)-2-(2-methylbenzyl)propylamino)methyl)phenyl 2-(hexyl((2S,3R,4R,5R)-2,3,4,5,6-pentahydroxyhexyl)amino)ethylcarbamate

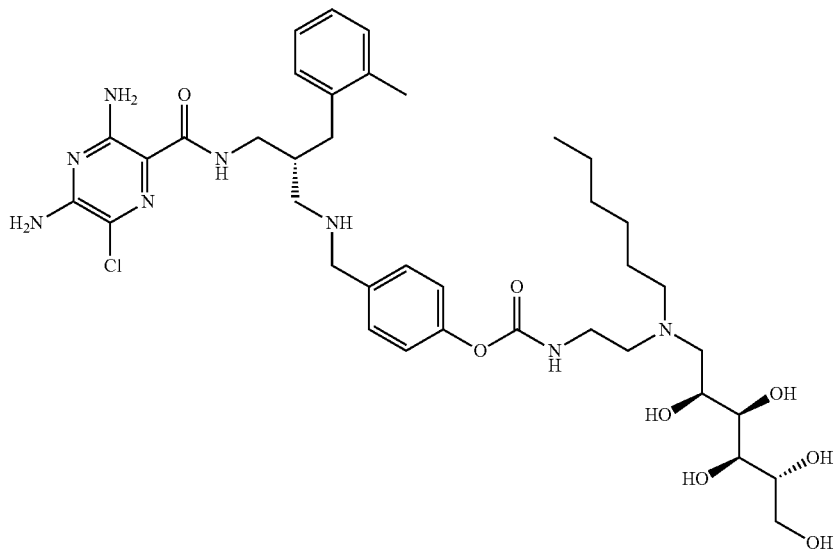 [SMILES: CCCCCCN(CCNC(=O)Oc1ccc(CNC[C@H](CNC(=O)c2nc(Cl)c(N)nc2N)Cc2ccccc2C)cc1)C[C@H](O)[C@@H](O)[C@H](O)[C@H](O)CO]

In a 25 mL round-bottomed flask was added tert-butyl ((S)-3-(3,5-diamino-6-chloropyrazine-2-carboxamido)-2-(2-methylbenzyl)propyl)(4-(((2-(((2S,3R)-2,3-dihydroxy-3-((2R,4R,5R)-5-hydroxy-2-phenyl-1,3-dioxan-4-yl)propyl)(hexyl)amino)ethyl)carbamoyl)oxy)benzyl)carbamate (step 5, 200 mg, 0.20 mmol) to EtOH (1 mL) to give a yellow solution. Aq. HCl (4M, 3 mL) was added and the resulting solution was stirred at room temperature for 12 h. The crude product was purified by preparative HPLC (Waters XBridge Prep C18 OBD column, 5μ silica, 50 mm diameter, 150 mm length), using a gradient of decreasing polarity of water (0.05% TFA) and MeCN as eluent. Fractions containing the desired compound were evaporated to dryness to afford the title compound (28.0 mg, 13%) as a yellow solid.

LC/MS: m/z 789.4 [M+H]$^+$ $^1$H NMR (300 MHz, CD$_3$OD): δ 0.79-0.99 (m, 3H), 1.25-1.55 (m, 6H), 1.69-1.91 (m, 2H), 2.25-2.45 (m, 4H), 2.51-2.84 (m, 1H), 2.81-3.01 (m, 3H), 3.28-3.31 (m, 4H), 3.34-3.82 (m, 12H), 3.86-3.92 (m, 1H), 4.09-4.37 (m, 3H), 7.03-7.35 (m, 6H), 7.453 (d, 2H).

EXAMPLE 12

3,5-diamino-6-chloro-N—((R)-3-((4-((2-(hexyl((2S,3R,4R,5R)-2,3,4,5,6-pentahydroxyhexyl)amino)ethyl)carbamoyl)phenethyl)amino)-2-(2-methylbenzyl)propyl)pyrazine-2-carboxamide Dihydrochloride

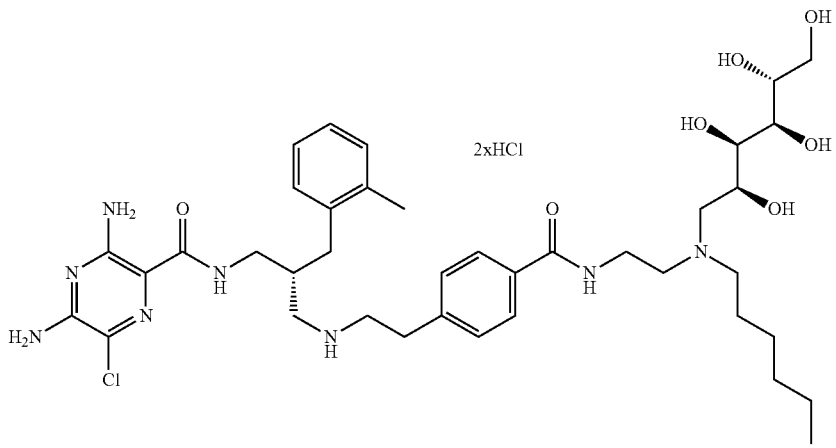 [SMILES: CCCCCCN(CCNC(=O)c1ccc(CCNC[C@H](CNC(=O)c2nc(Cl)c(N)nc2N)Cc2ccccc2C)cc1)C[C@H](O)[C@@H](O)[C@H](O)[C@H](O)CO]

Step 1
EN06927-61 tert-Butyl ((S)-3-(3,5-diamino-6-chloropyrazine-2-carboxamido)-2-(2-methylbenzyl)propyl)(4-((2-(hexyl((2S,3R,4R,5R)-2,3,4,5,6-pentahydroxyhexyl)amino)ethyl)carbamoyl)phenethyl)carbamate

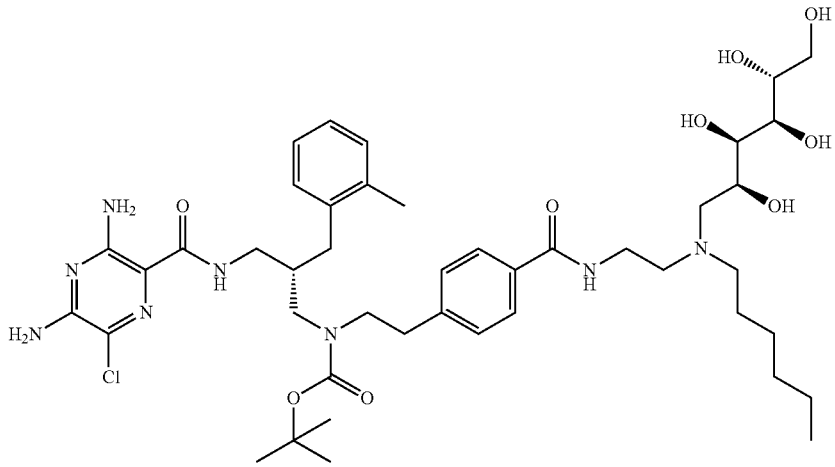 [SMILES: CCCCCCN(CCNC(=O)c1ccc(CCN(C[C@H](CNC(=O)c2nc(Cl)c(N)nc2N)Cc2ccccc2C)C(=O)OC(C)(C)C)cc1)C[C@H](O)[C@@H](O)[C@H](O)[C@H](O)CO]

(S)-tert-butyl (3-(3,5-diamino-6-chloropyrazine-2-carboxamido)-2-(2-methylbenzyl)propyl)(4-((2-(hexylamino)ethyl)carbamoyl)phenethyl)carbamate (Intermediate D, 500 mg, 0.69 mmol), (3R,4S,5S,6R)-6-(hydroxymethyl)tetrahydro-2H-pyran-2,3,4,5-tetraol (249 mg, 1.38 mmol) and DIPEA (0.121 mL, 0.69 mmol) were dissolved in MeOH (5 mL) and stirred at 50° C. for 40 min before addition of sodium cyanoborohydride (130 mg, 2.07 mmol) and acetic acid (0.044 mL, 0.76 mmol). Stirring was continued at 50° C. for 21 h and the reaction mixture was then allowed to cool to room temperature. The reaction was quenched by addition of 8% $NaHCO_3$ (aq). The mixture was diluted in EtOAc (50 mL) and 8% $NaHCO_3$ (aq) (50 mL), shaken and the phases separated. The aqueous phase was extracted with EtOAc (4×50 mL). The combined organic phases were dried with $Na_2SO_4$ (s), filtered and evaporated in vacuo. The compound was purified by preparative HPLC on a Kromasil C8 column (10 μm 250×50 ID mm) using a gradient of 20-60% acetonitrile in H2O/MeCN/AcOH 95/5/0.2 buffer over 20 minutes with a flow of 100 mL/min. The compounds were detected by UV at 265 nm. The compound was collected and freeze-dried to yield the title compound (385 mg, 63%) as a pale solid.

LC/MS: m/z 887.6 $[M+H]^+$ $^1$H NMR (500 MHz, DMSO-$d_6$) δ 0.80 (t, 3H), 1.12-1.26 (m, 6H), 1.29-1.43 (m, 11H), 2.16-2.29 (m, 4H), 2.41-2.48 (m, 2H), 2.56-2.67 (m, 2H), 2.71 (t, 2H), 2.96 (dd, 1H), 3.02-3.42 (m, 12H), 3.44 (dd, 1H), 3.47-3.54 (m, 1H), 3.55-3.74 (m, 3H), 4.18-4.79 (m, 4H), 6.96 (bs, 2H), 7.06-7.19 (m, 6H), 7.72 (d, 2H), 7.8-7.97 (m, 1H), 8.24-8.34 (m, 1H).

Step 2

3,5-diamino-6-chloro-N—((R)-3-((4-((2-(hexyl((2S,3R,4R,5R)-2,3,4,5,6-pentahydroxyhexyl)amino)ethyl)carbamoyl)phenethyl)amino)-2-(2-methylbenzyl)propyl)pyrazine-2-carboxamide Dihydrochloride

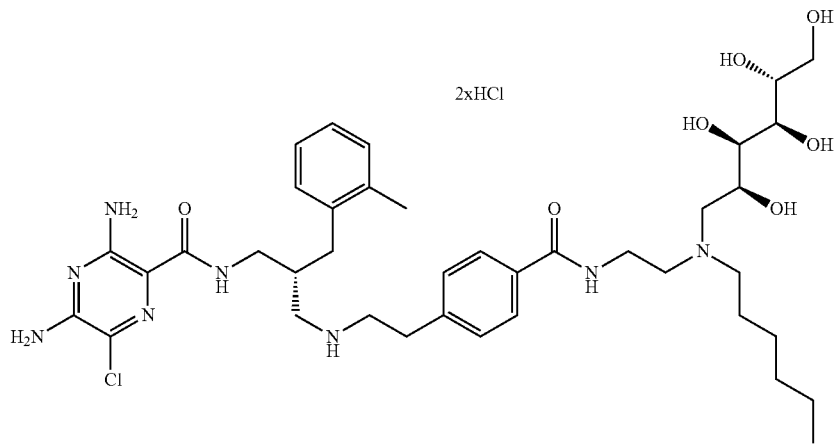 [SMILES: CCCCCCN(CCNC(=O)c1ccc(CCNC[C@H](CNC(=O)c2nc(Cl)c(N)nc2N)Cc2ccccc2C)cc1)C[C@H](O)[C@@H](O)[C@H](O)[C@H](O)CO]

Acetyl chloride (1.42 mL, 20 mmol) was added dropwise to an icebath cooled solution of MeOH (5 mL, 124 mmol). The solution was stirred for 5 min and was then added to tert-butyl ((S)-3-(3,5-diamino-6-chloropyrazine-2-carboxamido)-2-(2-methylbenzyl)propyl)(4-((2-(hexyl((2S,3R,4R,5R)-2,3,4,5,6-pentahydroxyhexyl)amino)ethyl)carbamoyl)phenethyl)carbamate (step 1, 385 mg, 0.43 mmol). The reaction was stirred at room temperature for 2.5 h and was then concentrated in vacuo. The residue was dissolved in water and freeze-dried to yield the title compound (369 mg, 99%) as a yellow solid.

LC/MS: m/z 787.4 [M+H]$^+$

1H NMR (500 MHz, DMSO-d6) δ 0.78-0.88 (m, 3H), 1.17-1.31 (m, 6H), 1.6-1.74 (m, 2H), 2.23-2.39 (m, 4H), 2.64-2.75 (m, 2H), 2.75-2.87 (m, 1H), 2.87-2.99 (m, 1H), 3.05 (t, 2H), 3.09-3.44 (m, 11H), 3.44-3.54 (m, 2H), 3.55-3.75 (m, 4H), 4-4.1 (m, 1H), 4.69 (bs, 7H), 6.88-7.2 (m, 5H), 7.23-7.3 (m, 1H), 7.36 (d, 2H), 7.88 (d, 2H), 8.24 (t, 1H), 8.85-9.16 (m, 3H), 9.63 (d, 1H).

EXAMPLE 13

3,5-diamino-6-chloro-N—((R)-3-((4-((2-(hexyl((2S,3R,4R)-2,3,4,5-tetrahydroxypentyl)amino)ethyl)carbamoyl)phenethyl)amino)-2-(2-methylbenzyl)propyl)pyrazine-2-carboxamide Dihydrochloride

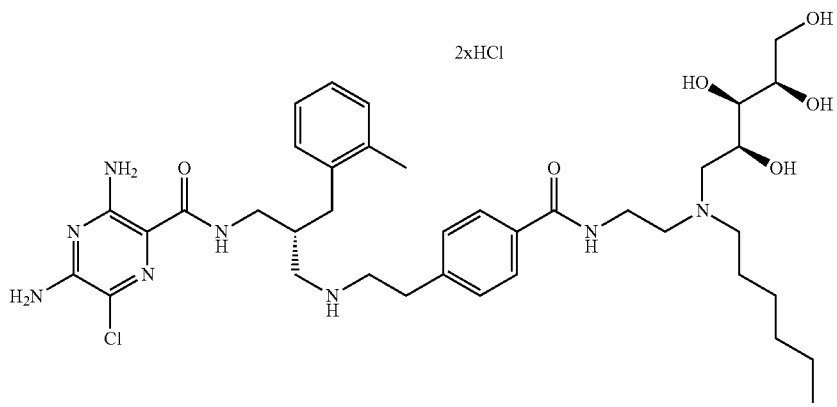 [SMILES: CCCCCCN(CCNC(=O)c1ccc(CCNC[C@H](CNC(=O)c2nc(Cl)c(N)nc2N)Cc2ccccc2C)cc1)C[C@H](O)[C@@H](O)[C@H](O)CO]

Step 1:

Tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)phenethyl)carbamate

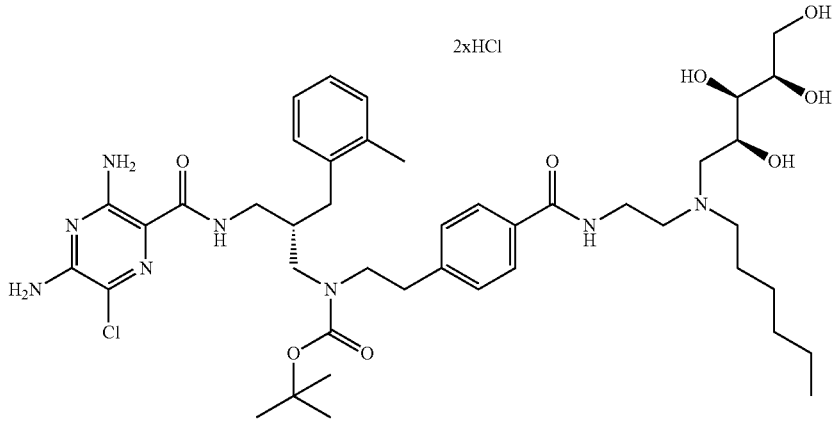 [SMILES: CCCCCCN(CCNC(=O)c1ccc(CCN(C[C@H](CNC(=O)c2nc(Cl)c(N)nc2N)Cc2ccccc2C)C(=O)OC(C)(C)C)cc1)C[C@H](O)[C@@H](O)[C@H](O)CO]

(S)-tert-butyl (3-(3,5-diamino-6-chloropyrazine-2-carboxamido)-2-(2-methylbenzyl)propyl)(4-((2-(hexylamino)ethyl)carbamoyl)phenethyl)carbamate (Intermediate D, 500 mg, 0.69 mmol), (2R,3S,4R)-2,3,4,5-tetrahydroxypentanal (208 mg, 1.38 mmol) and DIPEA (0.121 mL, 0.69 mmol) were dissolved in MeOH (5 mL) and stirred at 50° C. for 40 min before addition of sodium cyanoborohydride (130 mg, 2.07 mmol) and acetic acid (0.044 mL, 0.76 mmol). Stirring was continued at 50° C. for 21 h and was then allowed to cool to room temperature. The reaction was quenched by addition of 8% NaHCO3 (aq). The mixture was diluted in EtOAc (50 mL) and 8% NaHCO3 (aq) (50 mL), shaken and the phases separated. The aqueous phase was extracted with EtOAc (4×50 mL). The combined organic phases were dried with Na2SO4 (s), filtered and evaporated in vacuo. The compound was purified by preparative HPLC on a Kromasil C8 column (10 µm 250×50 ID mm) using a gradient of 20-60% acetonitrile in H2O/MeCN/AcOH 95/5/0.2 buffer over 20 minutes with a flow of 100 mL/min. The compounds were detected by UV at 265 nm. The compound was collected and freeze-dried to yield tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)phenethyl)carbamate (374 mg, 63%) as a pale solid.

LC/MS: m/z 857.6 [M+H]$^+$ $^1$H NMR (500 MHz, DMSO-d$_6$) δ 0.74-0.85 (m, 3H), 1.11-1.28 (m, 6H), 1.28-1.44 (m, 11H), 2.14-2.29 (m, 4H), 2.46 (dd, 2H), 2.55-2.65 (m, 2H), 2.71 (t, 2H), 2.96 (dd, 1H), 3.02-3.51 (m, 14H), 3.52-3.6 (m, 1H), 3.6-3.71 (m, 1H), 4.17-4.77 (m, 3H), 6.96 (bs, 2H), 7.05-7.2 (m, 6H), 7.72 (d, 2H), 7.8-7.97 (m, 1H), 8.23-8.34 (m, 1H).

Step 2:

3,5-diamino-6-chloro-N—((R)-3-((4-((2-(hexyl((2S,3R,4R)-2,3,4,5-tetrahydroxypentyl)amino)ethyl)carbamoyl)phenethyl)amino)-2-(2-methylbenzyl)propyl)pyrazine-2-carboxamide Dihydrochloride

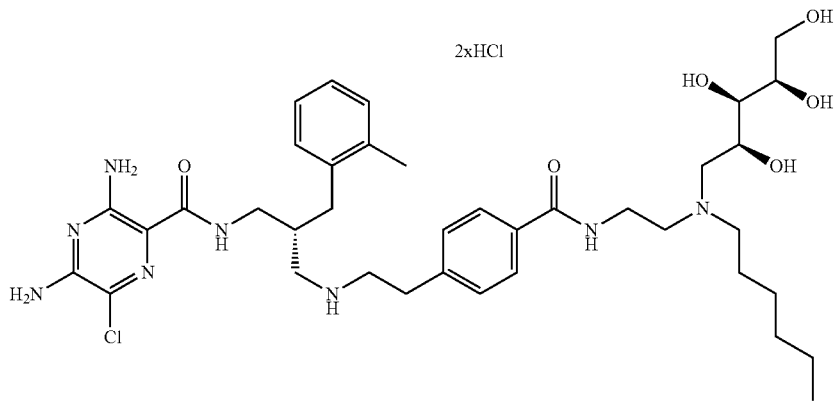 [SMILES: CCCCCCN(CCNC(=O)c1ccc(CCNC[C@H](CNC(=O)c2nc(Cl)c(N)nc2N)Cc2ccccc2C)cc1)C[C@H](O)[C@@H](O)[C@H](O)CO]

Acetyl chloride (1.42 mL, 20.0 mmol) was added dropwise to an icebath cooled solution of MeOH (5 mL, 123.59 mmol). The solution was stirred for 5 min and was then added to tert-butyl ((S)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)

phenethyl)carbamate (374 mg, 0.44 mmol). The reaction was stirred at room temperature for 2.5 h and was then concentrated in vacuo. The residue was dissolved in water and freeze-dried to yield 3,5-diamino-6-chloro-N—((R)-3-((4-((2-(hexyl((2S,3R,4R)-2,3,4,5-tetrahydroxypentyl) amino)ethyl)carbamoyl)phenethyl)amino)-2-(2-methylbenzyl)propyl)pyrazine-2-carboxamide dihydrochloride (361 mg, 100%) as a yellow solid.

LC/MS: m/z 757.4 [M+H]$^+$ $^1$H NMR (500 MHz, DMSO-d$_6$) δ 1-1.09 (m, 3H), 1.39-1.53 (m, 6H), 1.84-1.95 (m, 2H), 2.50 (s, 3H), 2.53-2.62 (m, 1H), 2.86-2.97 (m, 2H), 2.97-3.07 (m, 1H), 3.09-3.2 (m, 1H), 3.22-3.73 (m, 15H), 3.77-3.96 (m, 3H), 4.23-4.32 (m, 1H), 4.84 (bs, 6H), 7.15-7.42 (m, 5H), 7.45-7.52 (m, 1H), 7.58 (d, 2H), 8.11 (d, 2H), 8.46 (t, 1H), 9.13-9.2 (m, 1H), 9.30 (d, 2H), 9.92 (d, 1H).

EXAMPLE 14

3,5-diamino-6-chloro-N—((S)-3-((4-((2-(hexyl((2S, 3R,4R)-2,3,4,5-tetrahydroxypentyl)amino)ethyl) carbamoyl)benzyl)amino)-2-(2-methylbenzyl)propyl)pyrazine-2-carboxamide Acetic Acid

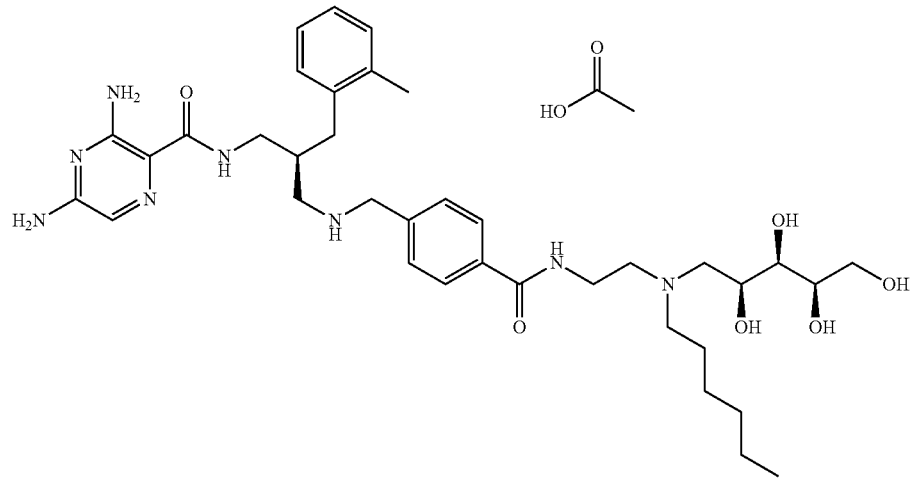

Step 1 tert-butyl ((R)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl) amino)ethyl)carbamoyl)benzyl)carbamate

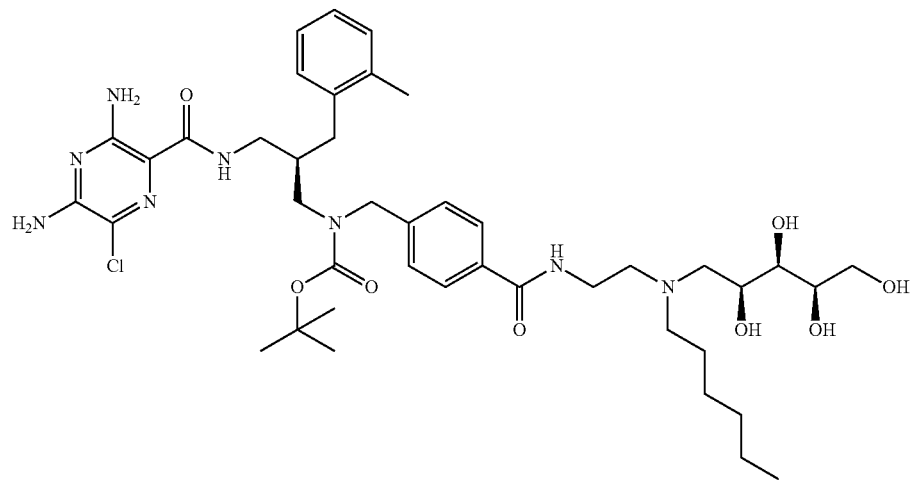 [SMILES: CCCCCCN(CCNC(=O)c1ccc(CN(C[C@@H](CNC(=O)c2nc(Cl)c(N)nc2N)Cc2ccccc2C)C(=O)OC(C)(C)C)cc1)C[C@H](O)[C@@H](O)[C@H](O)CO]

(R)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate, (Intermediate H) (163 mg, 0.23 mmol), (2R,3S,4R)-2,3,4,5-tetrahydroxypentanal (69.0 mg, 0.46 mmol) and DIPEA (0.040 mL, 0.23 mmol) were dissolved in MeOH (4 mL) and stirred at room temperature for 1 h. Sodium cyanoborohydride (14.44 mg, 0.23 mmol) and acetic acid (0.039 mL, 0.69 mmol) were added and the reaction heated to 50° C. for 20 h and was then allowed to cool to room temperature. The reaction was quenched by addition of 8% NaHCO$_3$ (aq) and stirred for 30 min. The solvent was concentrated in vacuo. The residue was dissolved in EtOAc (25 mL) and 8% NaHCO$_3$ (aq) (25 mL), shaken and the phases separated. The aqueous phase was extracted with EtOAc (2×25 mL). The combined organic phases were dried with Na$_2$SO$_4$ (s), filtered and evaporated in vacuo. The compound was purified by preparative HPLC on a Kromasil C8 column (10 μm 250×20 ID mm) using a gradient of 30-70% acetonitrile in H$_2$O/ACN/AcOH 95/5/0.2 buffer, over 20 minutes with a flow of 19 mL/min. The compounds were detected by UV at 265 nm. The product fractions were collected and freeze-dried to yield tert-butyl ((R)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)benzyl)carbamate (127 mg, 65.5%) as a solid.

$^1$H NMR (500 MHz, DMSO-d$_6$) δ 0.75-0.84 (m, 3H), 1.13-1.26 (m, 6H), 1.29-1.42 (m, 11H), 2.20 (s, 3H), 2.25-2.35 (m, 1H), 2.41-2.47 (m, 2H), 2.56-2.62 (m, 2H), 2.89-3.05 (m, 1H), 3.07-3.15 (m, 1H), 3.2-3.49 (m, 13H), 3.52-3.59 (m, 1H), 3.61-3.69 (m, 1H), 4.21-4.35 (m, 2H), 4.35-4.55 (m, 3H), 6.96 (bs, 1H), 7.04-7.19 (m, 6H), 7.71 (d, 2H), 7.77-7.98 (m, 1H), 8.24-8.32 (m, 1H).

MS ES$^+$: m/z 843.4 [M+H]$^+$

Step 2

3,5-diamino-6-chloro-N—((S)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide Acetic Acid

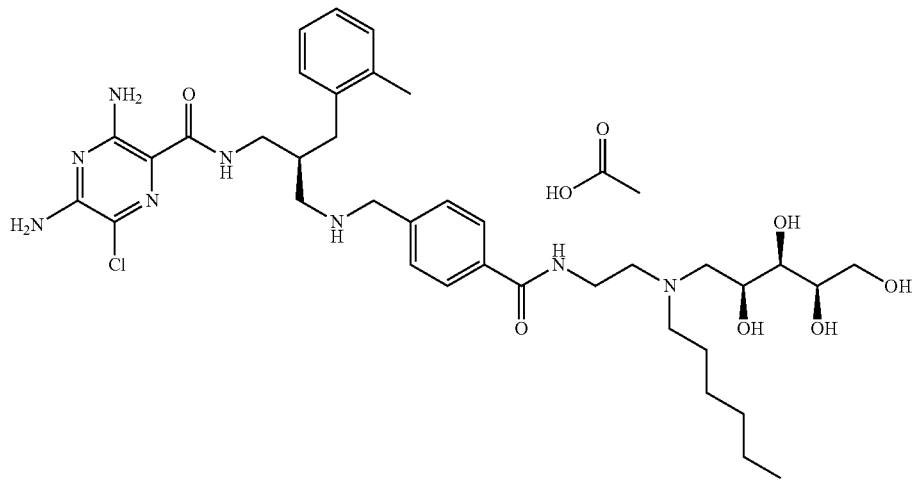

Acetyl chloride (0.711 mL, 10 mmol) was added dropwise to an icebath cooled vial of MeOH (2.5 mL, 61.79 mmol) and stirred for 5 min before addition of tert-butyl ((R)-3-(3,5-diamino-6-chloropyrazine-2-carboxamido)-2-(2-methylbenzyl)propyl)(4-((2-(hexyl((2S,3R,4R)-2,3,4,5-tetrahydroxypentyl)amino)ethyl)carbamoyl)benzyl)carbamate (127 mg, 0.15 mmol). The reaction was stirred at room temperature for 1 h and was then concentrated in vacuo. The residue was dissolved in EtOAc (25 mL) and 5% Na$_2$CO$_3$ (aq) (25 mL), shaken and the phases separated. The aqueous phase was extracted with EtOAc (5×25 mL). The combined organic phases were dried with Na$_2$SO$_4$ (s), filtered and evaporated in vacuo. The compound was purified by preparative HPLC on a Kromasil C8 column (10 μm 250×20 ID mm) using a gradient of 5-45% acetonitrile in H$_2$O/ACN/AcOH 95/5/0.2 buffer, over 20 minutes with a flow of 19 mL/min. The compounds were detected by UV at 268 nm. The product was freeze-dried to yield 3,5-diamino-6-chloro-N—((S)-3-((4-((2-(hexyl((2S,3R,4R)-2,3,4,5-tetrahydroxypentyl)amino)ethyl)carbamoyl)benzyl)amino)-2-(2-methylbenzyl)propyl)pyrazine-2-carboxamide (100 mg, 82%) as a pale solid.

$^1$H NMR (500 MHz, DMSO-d$_6$) δ 0.77-0.83 (m, 3H), 1.13-1.25 (m, 6H), 1.32-1.41 (m, 2H), 1.90 (s, 4H), 1.96-2.05 (m, 1H), 2.24 (s, 3H), 2.35-2.55 (m, 6H), 2.55-2.63 (m, 4H), 3.14-3.23 (m, 2H), 3.24-3.4 (m, 9H), 3.4-3.49 (m, 4H), 3.56 (q, 1H), 3.62-3.71 (m, 2H), 3.74 (d, 1H), 6.96 (bs, 2H), 7.04-7.14 (m, 4H), 7.40 (d, 2H), 7.74 (d, 2H), 8.28 (t, 1H), 8.33 (t, 1H).

MS ES$^+$: m/z 743.5 [M+H]$^+$

EXAMPLE 15

3,5-diamino-6-chloro-N—((S)-3-((4-((2-(hexyl((2R,3S,4S)-2,3,4,5-tetrahydroxypentyl)amino)ethyl)carbamoyl)benzyl)amino)-2-(2-methylbenzyl)propyl) pyrazine-2-carboxamide Acetic Acid

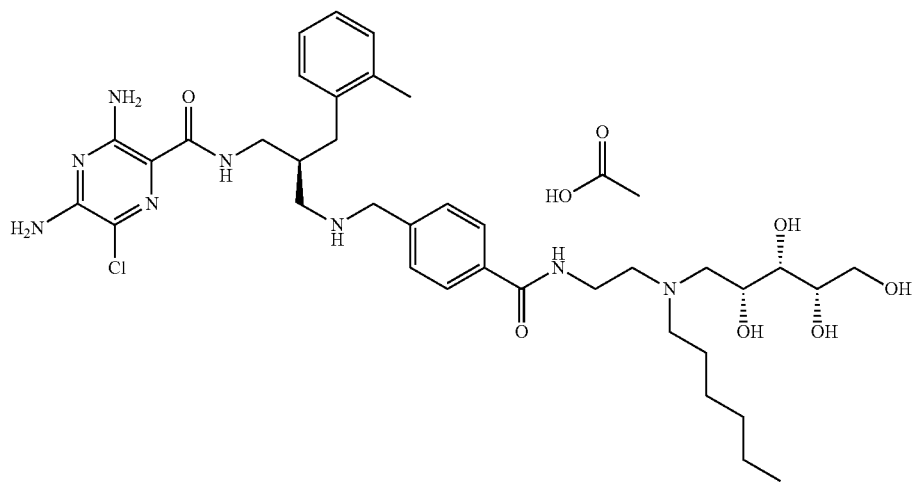

Step 1 tert-butyl ((R)-3-(3,5-diamino-6-chloropyrazine-2-carboxamido)-2-(2-methylbenzyl)propyl)(4-((2-(hexyl((2R,3S,4S)-2,3,4,5-tetrahydroxypentyl)amino)ethyl)carbamoyl)benzyl)carbamate

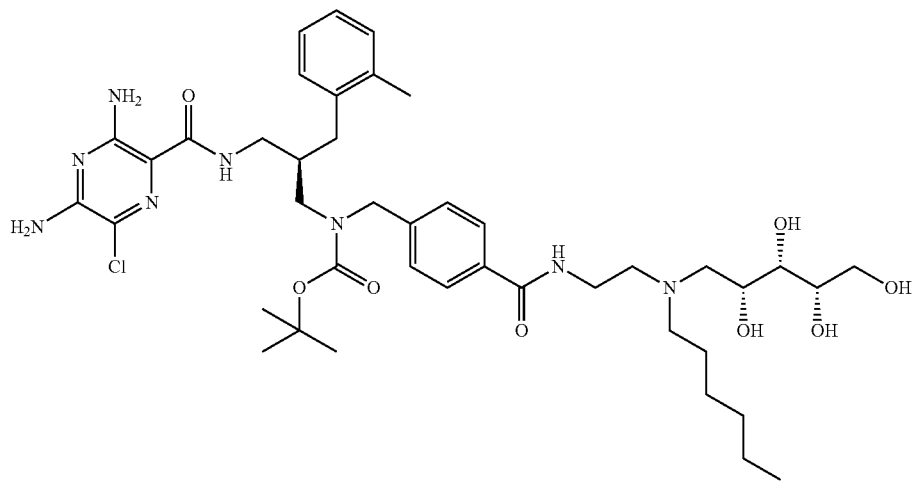 [SMILES: CCCCCCN(CCNC(=O)c1ccc(CN(C[C@@H](CNC(=O)c2nc(Cl)c(N)nc2N)Cc2ccccc2C)C(=O)OC(C)(C)C)cc1)C[C@@H](O)[C@H](O)[C@@H](O)CO]

(R)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate, (Intermediate G) (163 mg, 0.23 mmol), (2S,3R,4S)-2,3,4,5-tetrahydroxypentanal (69.0 mg, 0.46 mmol) and DIPEA (40.1 µl, 0.23 mmol) were dissolved in MeOH and stirred at room temperature for 1 h. Sodium cyanoborohydride (14.44 mg, 0.23 mmol) and acetic acid (39.5 µl, 0.69 mmol) were added and the reaction heated to 50° C. for 20 h and was then allowed to cool to room temperature. The reaction was quenched by addition of 8% NaHCO$_3$ (aq) and stirred for 30 min. The solvent was concentrated in vacuo. The residue was a dissolved in EtOAc (25 mL) and 8% NaHCO$_3$ (aq) (25 mL), shaken and the phases separated. The aqueous phase was extracted with EtOAc (5×25 mL). The combined organic phases were dried with Na$_2$SO$_4$ (s), filtered and evaporated in vacuo. The compound was purified by preparative HPLC on a Kromasil C8 column (10 µm 250×20 ID mm) using a gradient of 30-70% acetonitrile in H$_2$O/ACN/AcOH 95/5/0.2 buffer, over 20 minutes with a flow of 19 mL/min. The compounds were detected by UV at 265 nm. The product fractions were collected and freeze-dried to yield tert-butyl ((R)-3-(3,5-diamino-6-chloropyrazine-2-carboxamido)-2-(2-methylbenzyl)propyl)(4-((2-(hexyl((2R,3S,4S)-2,3,4,5-tetrahydroxypentyl)amino)ethyl)carbamoyl)benzyl)carbamate (135 mg, 69.7%) as a solid.

$^1$H NMR (500 MHz, DMSO-d$_6$) δ 0.79 (d, 3H), 1.16 (d, 6H), 1.36 (s, 11H), 2.20 (s, 3H), 2.31 (s, 1H), 2.50 (dt, 5H), 2.58 (s, 3H), 2.92-3.05 (m, 1H), 3.06-3.15 (m, 1H), 3.31 (s, 6H), 3.39-3.5 (m, 2H), 3.53-3.59 (m, 1H), 3.61-3.69 (m, 1H), 4.22-4.34 (m, 2H), 4.34-4.55 (m, 3H), 6.97 (bs, 2H), 7.04-7.18 (m, 6H), 7.71 (d, 2H), 7.78-7.97 (m, 1H), 8.25-8.32 (m, 1H).

MS ES$^+$: m/z 843.5 [M+H]$^+$

Step 2

3,5-diamino-6-chloro-N—((S)-3-((4-((2-(hexyl((2R,3S,4S)-2,3,4,5-tetrahydroxypentyl)amino)ethyl)carbamoyl)benzyl)amino)-2-(2-methylbenzyl)propyl) pyrazine-2-carboxamide Acetic Acid

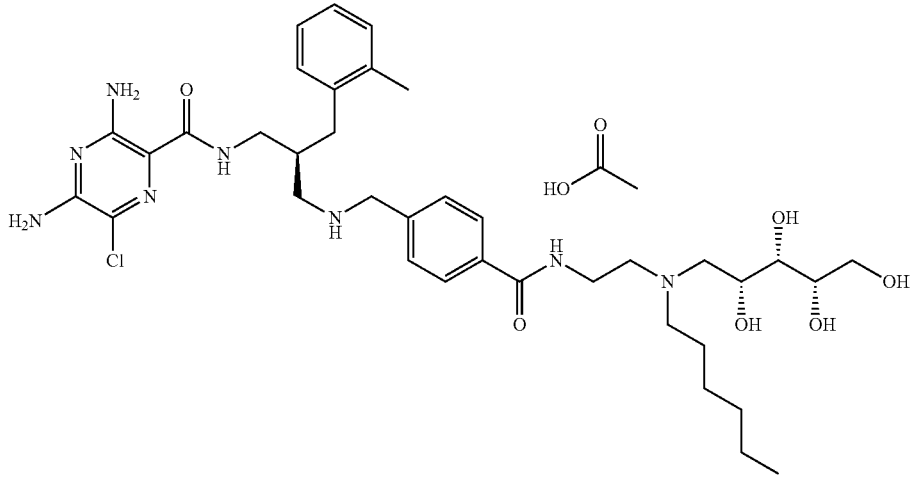

Acetyl chloride (0.711 mL, 10 mmol) was added dropwise to an icebath cooled vial of MeOH (2.5 mL, 61.79 mmol) and stirred for 5 min before addition of tert-butyl ((R)-3-(3,5-diamino-6-chloropyrazine-2-carboxamido)-2-(2-methylbenzyl)propyl)(4-((2-(hexyl((2R,3S,4S)-2,3,4,5-tetrahydroxypentyl)amino)ethyl)carbamoyl)benzyl)carbamate (135 mg, 0.16 mmol). The reaction was stirred at room temperature for 1 h and was then evaporated in vacuo. The residue was dissolved in EtOAc (25 mL) and 5% $Na_2CO_3$ (aq) (25 mL), shaken and the phases separated. The aqueous phase was extracted with EtOAc (5×25 mL). The combined organic phases were dried with $Na_2SO_4$ (s), filtered and evaporated in vacuo. The compound was purified by preparative HPLC on a Kromasil C8 column (10 μm 250×20 ID mm) using a gradient of 5-45% acetonitrile in $H_2O$/ACN/AcOH 95/5/0.2 buffer, over 20 minutes with a flow of 19 mL/min. The compounds were detected by UV at 268 nm. The product was freeze-dried to yield 3,5-diamino-6-chloro-N—((S)-3-((4-((2-(hexyl((2R,3S,4S)-2,3,4,5-tetrahydroxypentyl)amino)ethyl)carbamoyl)benzyl)amino)-2-(2-methylbenzyl)propyl)pyrazine-2-carboxamide (93 mg, 70.2%) as a pale solid.

$^1$H NMR (500 MHz, DMSO-$d_6$) δ 0.76-0.83 (m, 3H), 1.14-1.25 (m, 6H), 1.31-1.42 (m, 2H), 1.91 (s, 3H), 1.95-2.06 (m, 1H), 2.24 (s, 3H), 2.35-2.54 (m, 6H), 2.60 (dd, 4H), 3.14-3.5 (m, 11H), 3.56 (q, 1H), 3.66 (dd, 2H), 3.74 (d, 1H), 6.96 (s, 2H), 7.04-7.14 (m, 4H), 7.40 (d, 2H), 7.74 (d, 2H), 8.28 (t, 1H), 8.33 (t, 1H).

MS ES$^+$: m/z 743.4 [M+H]$^+$

EXAMPLE 16

3,5-diamino-6-chloro-N—((R)-3-(3-(2-(hexyl((2S,3R,4R,5R)-2,3,4,5,6-pentahydroxyhexyl)amino)ethylcarbamoyl)phenethylamino)-2-(2-methylbenzyl)propyl)pyrazine-2-carboxamide

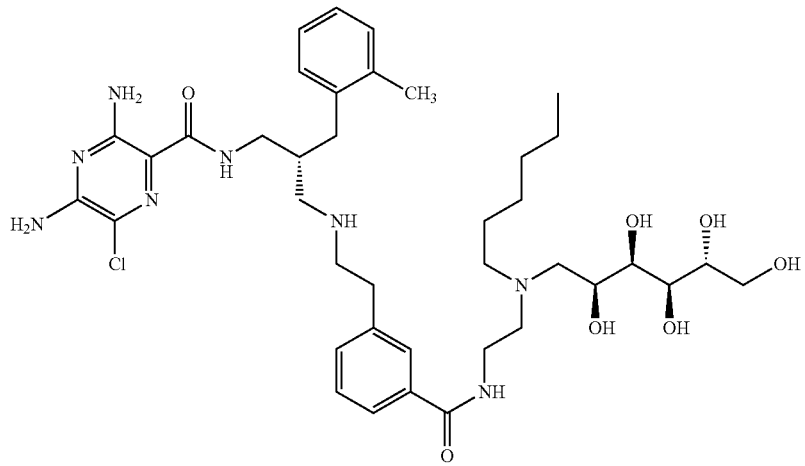 [SMILES: CCCCCCN(CCNC(=O)c1cccc(CCNC[C@H](CNC(=O)c2nc(Cl)c(N)nc2N)Cc2ccccc2C)c1)C[C@H](O)[C@@H](O)[C@H](O)[C@H](O)CO]

Step 1 tert-butyl (S)-3-(3,5-diamino-6-chloropyrazine-2-carboxamido)-2-(2-methylbenzyl)propyl(3-(2-(hexyl((2S,3R,4R,5R)-2,3,4,5,6-pentahydroxyhexyl)amino)ethylcarbamoyl)phenethyl)carbamate

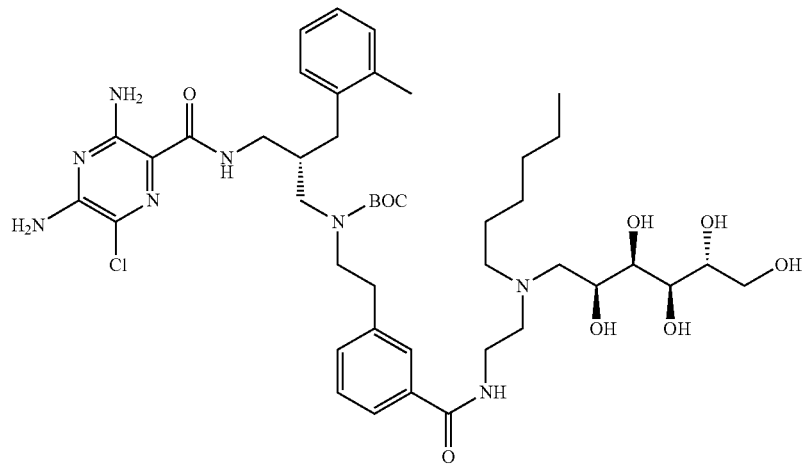 [SMILES: CCCCCCN(CCNC(=O)c1cccc(CCN(C[C@H](CNC(=O)c2nc(Cl)c(N)nc2N)Cc2ccccc2C)C(=O)OC(C)(C)C)c1)C[C@H](O)[C@@H](O)[C@H](O)[C@H](O)CO]

In a 50 mL round-bottomed flask was (S)-tert-butyl (3-(3,5-diamino-6-chloropyrazine-2-carboxamido)-2-(2-methylbenzyl)propyl)(3-((2-(hexylamino)ethyl)carbamoyl)phenethyl) carbamate (intermediate D, 370 mg, 0.51 mmol) and (3R,4S,5S,6R)-6-(hydroxymethyl)tetrahydro-2H-pyran-2,3,4,5-tetraol (138 mg, 0.77 mmol) in MeOH (15 mL) to give a yellow solution. After stirring the above mixture for 30 min NaCNBH$_3$ (32.1 mg, 0.51 mmol) was added. The resulting solution was stirred at 50° C. for 16 hours. The solvent was removed under reduced pressure to give crude product tert-butyl ((S)-3-(3,5-diamino-6-chloropyrazine-2-carboxamido)-2-(2-methylbenzyl)propyl)(3-((2-(hexyl((2S, 3R,4R,5R)-2,3,4,5,6-pentahydroxyhexyl)amino)ethyl)carbamoyl)phenethyl)carbamate (500 mg, 110%) as yellow solid. The product was used in the next step directly without further purification.

LC/MS: m/z 887 [M+H]$^+$

Step 2

3,5-diamino-6-chloro-N—((R)-3-(3-(2-(hexyl((2S,3R,4R,5R)-2,3,4,5,6-pentahydroxyhexyl)amino)ethylcarbamoyl)phenethylamino)-2-(2-methylbenzyl)propyl)pyrazine-2-carboxamide

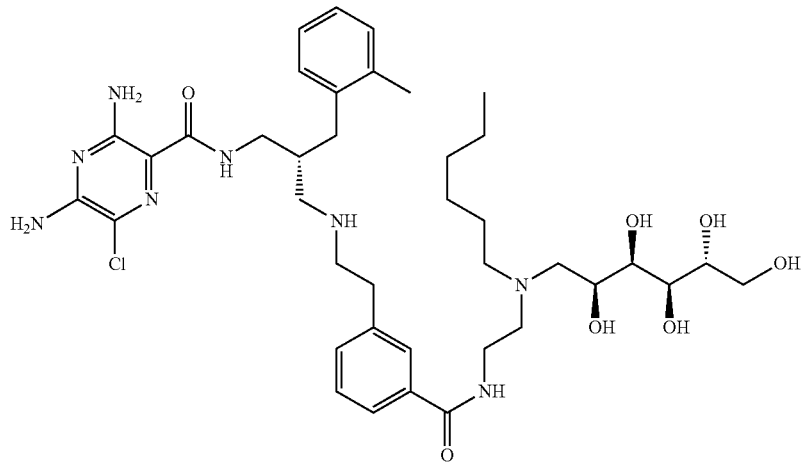 [SMILES: CCCCCCN(CCNC(=O)c1cccc(CCNC[C@H](CNC(=O)c2nc(Cl)c(N)nc2N)Cc2ccccc2C)c1)C[C@H](O)[C@@H](O)[C@H](O)[C@H](O)CO]

In a 50 mL round-bottomed flask was tert-butyl ((S)-3-(3,5-diamino-6-chloropyrazine-2-carboxamido)-2-(2-methylbenzyl)propyl)(3-((2-(hexyl((2S,3R,4R,5R)-2,3,4,5,6-pentahydroxyhexyl)amino)ethyl)carbamoyl)phenethyl)carbamate (500 mg, 0.56 mmol) in HCl/MeOH (20 mL, 0.56 mmol) to give a yellow solution. The resulting solution was stirred at rt for 2 h. The solvent was removed under reduced pressure. The crude was purified by preparative HPLC (Waters XBridge Prep C18 OBD column, 5μ silica, 50 mm diameter, 150 mm length), using decreasingly polar mixtures of water (containing 0.1% $NH_4HCO_3$) and MeCN as eluents. Fractions containing the desired compound were evaporated to dryness to afford 3,5-diamino-6-chloro-N—((R)-3-((3-((2-(hexyl((2S,3R,4R,5R)-2,3,4,5,6-pentahydroxyhexyl)amino)ethyl)carbamoyl)phenethyl)amino)-2-(2-methylbenzyl)propyl)pyrazine-2-carboxamide (87 mg, 20%) as a yellow solid.

LC/MS: m/z 788 $[M+H]^+$ $^1$H NMR (300 MHz, $CD_3OD$, 25° C.): δ 0.85-0.91 (m, 3H), 1.15-1.35 (m, 6H), 1.39-1.59 (m, 2H), 2.12-2.25 (m, 1H), 2.31 (s, 3H), 2.57-2.89 (m, 13H), 3.29-3.33 (m, 2H), 3.38-3.64 (m, 3H), 3.66-3.84 (m, 6H), 7.09-7.16 (m, 4H), 7.38 (d, 2H), 7.70-7.73 (m, 2H).

SYNTHESIS OF INTERMEDIATES

Intermediate A (R)-3,5-diamino-N-(3-amino-2-(2-methylbenzyl)propyl)-6-chloropyrazine-2-carboxamide

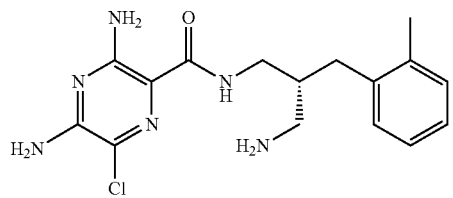 [SMILES: Cc1ccccc1C[C@H](CN)CNC(=O)c1nc(Cl)c(N)nc1N]

Step 1:

Dimethyl 2-(2-methylbenzyl)malonate

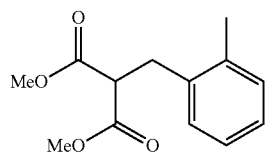 [SMILES: COC(=O)C(Cc1ccccc1C)C(=O)OC]

A reactor was charged with dimethyl malonate (6.00 kg, 45.4 mol) and methanol (21.3 L). 25% NaOMe/MeOH (10.37 L, 45.2 mol) was added over 10 minutes and then 2-methyl benzylchloride (4.26 kg, 30.3 mol) was added over 1.5 h, maintaining a reaction temperature below 30° C. Sat. $NH_4Cl$ (53.1 L) was added to the reaction, resulting in pH 8.5. The product was extracted with isopropyl acetate (3×25 L) and the combined organic layers were washed with 10% brine (10 L) and concentrated under reduced pressure to afford title compound as an oil (8.63 kg, 68 wt %, 83%). The so obtained title compound contained dialkylated malonate. Purity by HPLC: 86%.

LC/MS: m/z 237 $[M+H]^+$ $^1$H-NMR (DMSO-$d_6$, 270 MHz) δ 7.17-7.05 (4H, m), 3.60 (6 h, s), 3.82 (1H, t), 3.12 (2H, s), 2.21 (3H, s);
$^{13}$C-NMR (DMSO-$d_6$, 270 MHz) δ 169.5, 136.6, 136.3, 130.8, 129.5, 127.3, 126.4, 52.8, 52.0, 31.8, 19.4.

Step 2

2-(2-Methylbenzyl)malonamide

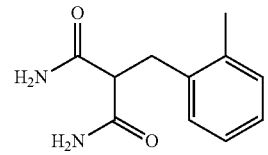

A reactor was charged with dimethyl-2-(2-methylbenzyl)malonate (step 1, 5.9 kg, 68% wt, 17.0 mol) and methanol (14.8 L). 34% Ammonium hydroxide (24 L, 36 equiv.) was added and the reaction was stirred at 25° C. until considered complete by HPLC analysis. The solids were filtered off and then MTBE (15.3 L) was added. After 30 min the solids were filtered off, washed with MTBE (2×15.3 L) and dried under reduced pressure at 60° C. to give the title compound as a white solid (3.2 kg, 91%).

LC/MS: m/z 206.9 $[M+H]^+$ $^1$H-NMR (DMSO-$d_6$, 270 MHz) δ 7.32-7.21 (2H, br s), 7.15-7.00 (6H, m), 3.33 (1H, t), 2.96 (2H, d), 2.28 (3H, s);
$^{13}$C-NMR (DMSO-$d_6$, 270 MHz) δ 171.0, 137.5, 136.0, 129.9, 128.9, 126.1, 125.6, 53.2, 32.5, 19.1.

Step 3

2-(2-Methylbenzyl)propane-1,3-diamine

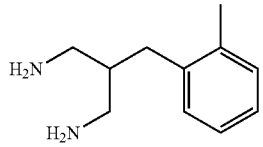

A reactor was charged with 2-(2-methylbenzyl)malonamide (1.32 kg, 6.40 mol) and THF (5.4 L). The viscous mixture was cooled to 0° C. and 1M borane-THF (25.6 L, 25.6 mol) was added during 2 h, maintaining a reaction temperature below 2° C. The reaction was warmed to 15° C. and then stirred at 50° C. over night. When HPLC analysis indicated less than 8% of starting material remained, the reaction mixture was quenched into 4M KOH (8 L), maintaining a temperature below 30° C. The organic layer was concentrated under reduced pressure and the aqueous layer was extracted twice with MTBE (2×10 L). The combined MTBE extracts was added to the concentrated organic layer and the combined organic layers were then charged to a solution of 6M HCl (10 L), maintaining a temperature below 30° C. The aqueous phase was washed with MTBE (10 L) and then basified with 6M KOH (12 L). The aqueous phase was extracted twice with THF (10 L and then 5 L) and the combined organic phase was concentrated under reduced pressure. Toluene (5 L) was added and then azeotroped distilled off to remove any residual water. The mixture was triturated with toluene (5 L) and the solids were filtered off and washed with toluene (3 L). The filtrate was concentrated under reduced pressure affording the title compound as the free amine (1.13 kg, 70% yield). Purity by HPLC: 91%.
LC/MS: m/z 179.0 [M+H]$^+$
$^1$H-NMR (CDCl$_3$, 270 MHz) δ 7.12-7.00 (4H, m), 2.72-2.59 (4H, m), 2.52 (2H, d), 2.27 (3H, s), 1.64 (1H, m), 1.48-1.25 (4H, br s); $^{13}$C-NMR (CDCl$_3$, 270 MHz) δ 139.0, 136.3, 130.5, 129.9, 126.2, 125.9, 44.7, 43.8, 34.3, 19.6.

Step 4

2-(2-Methylbenzyl)propane-1,3-diamine L-tartrate

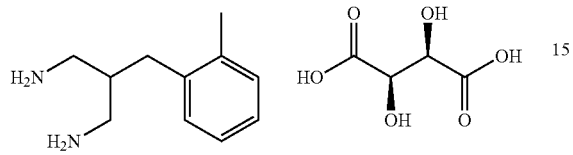

To crude diamine (from step 3) (1.62 kg, 9.1 mol) was added ethanol (4 L). A solution of L-tartaric acid (1.62 kg, 10.8 mol) dissolved in ethanol (11 L) was added, keeping the temperature below 40° C. The mixture was stirred at 25° C. for 3 d and then the solids were filtered off, washed with ethanol (2×2 L) and dried under reduced pressure at 50° C. to give the title compound as its mono-L-tartrate salt (3.21 kg, quantitative yield). Purity by HPLC: 92.2%.
LC/MS: m/z 179.0 [M+H]$^+$
$^1$H-NMR (D$_2$O, 270 MHz) δ 7.30-7.15 (4H, m), 4.27 (2H, s), 3.20-3.07 (2H, dd), 3.04-2.94 (2H, dd), 2.79 (2H, d), 2.41 (1H, m), 2.27 (3H, s); $^{13}$C-NMR (D$_2$O, 270 MHz) δ 178.4, 137.2, 135.7, 131.0, 130.0, 127.6, 126.7, 73.9, 40.5, 35.9, 32.8, 18.7.

Step 5

(R)-Allyl (3-amino-2-(2-methylbenzyl)propyl)carbamate (1-(R))

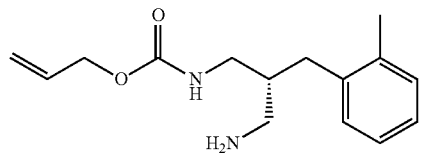

A reactor was charged with 2-(2-methylbenzyl)propane-1,3-diamine L-tartrate salt (3.57 kg, 10.9 mol) and water (17 L). 10M NaOH (17 L, 170 mol) was added, maintaining a reaction temperature below 25° C. The mixture was stirred for 30 min at 25° C. for 3 d and then 2-MeTHF (14 L) was added. The layers were separated and the aqueous phase was extracted with 2-MeTHF (14 L). The combined organic phase was dried (sodium sulfate), filtered and concentrated under reduced pressure affording the free diamine. A reactor was charged with the free diamine, 2-MeTHF (37.4 L) and diallyl carbonate (1.80 kg, 12.6 mol). Immobilized lipase Amano PS IM (5.61 kg, 3 wt equivalents) was added in portions over 30 min and the temperature was set at 30° C. After 4 days, $^1$H NMR indicated less than 5% starting material left and the reaction mixture was clear filtered through Celite and concentrated under reduced pressure to afford the title compound (2.68 kg, 82% ee, 100% yield). Purity by HPLC: 84.7%.
LC/MS: m/z 263.1 [M+H]$^+$
$^1$H-NMR (CDCl$_3$, 270 MHz) δ 7.15-7.05 (4H, m), 5.99-5.81 (1H, m), 5.80-5.60 (1H, br s), 5.35-5.15 (2H, m), 4.54 (2H, d), 3.40-3.14 (2H, m), 2.85-2.52 (4H, m), 2.29 (3H, s), 1.90-1.77 (1H, m), 1.50-1.10 (2H, br s); $^{13}$C-NMR (CDCl$_3$, 270 MHz) δ 156.6, 138.1, 136.1, 133.0, 130.5, 129.7, 126.3, 125.9, 117.5, 65.4, 44.0, 43.4, 41.6, 34.2, 19.5.

Step 6

(R)-Allyl (3-amino-2-(2-methylbenzyl)propyl)carbamate (1-(R)) D-tartrate Salt

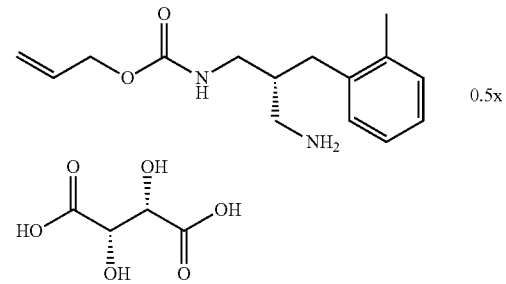

Crude (R)-allyl (3-amino-2-(2-methylbenzyl)propyl)carbamate (2.68 kg, 10.2 mol) was added to EtOH (7.1 L). A solution of D-tartaric acid (1.53 kg, 10.2 mol) in EtOH (8 L) was added keeping the temperature below 25° C. After approximately 1 h a precipitate began to form and the mixture was allowed to stir over night. MeCN (5 L) was added at 25° C. and the solids were filtered off, washed with MeCN (2×5 L) and dried under reduced pressure at 40° C. to afford 2.94 kg of the title compound ((R) D-tartrate salt, 100% yield) in a stoichiometric ratio base/di-acid=2:1. Purity by HPLC: 91.6%.
LC/MS: m/z 263.1 [M+H]$^+$
$^1$H-NMR (DMSO-d$_6$, 270 MHz) δ 7.50 (1H, t), 7.22-7.05 (4H, m), 5.98-5.85 (1H, m), 5.35-5.12 (2H, m), 4.48 (2H, d), 3.95 (2H, s), 3.13-2.99 (2H, m), 2.90-2.79 (1H, m), 2.75-2.58 (2H, m), 2.26 (3H, s), 2.08 (1H, m); $^{13}$C-NMR (DMSO-d$_6$, 270 MHz) δ 174.6, 156.6, 137.4, 136.1, 133.7, 130.3, 129.7, 126.3, 125.8, 117.0, 71.8, 64.4, 65.5, 37.6, 32.7, 19.1, 18.9.
Chiral HPLC (method A): 88.3% ee; r.t.=11.14 min (S), 14.57 min (R).

Step 7

(R)-allyl (3-amino-2-(2-methylbenzyl)propyl)carbamate

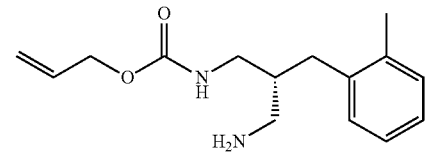 [SMILES: C=CCOC(=O)NC[C@@H](CN)Cc1ccccc1C]

To a 50 L vessel under nitrogen was added water (14.7 L) and MTBE (14.7 L), this was followed by the addition of the (R)-Allyl (3-amino-2-(2-methylbenzyl)propyl)carbamate (1-(R)) D-tartrate salt (step 6, 2940 g). 10M NaOH (14.7 L) was added to the mixture and the temperature was maintained below 30° C. The mixture was stirred for 30 mins, the organics were separated and the aqueous re-extracted with MTBE (14.7 L). A portion of the organics were concentrated in vacuo (1 L) to give an extrapolated yield of 1779 g, 95%.

LC/MS: m/z 263.1 [M+H]$^+$ $^1$H NMR (CDCl$_3$, 270 MHz) δ 7.05-7.15 (4H, m), 5.80-5.99 (1H, m), 5.32-5.14 (m, 2H), 4.52 (d, 2H), 3.15-3.38 (m, 2H), 2.55-2.81 (m, 2H), 2.54 (d, 2H), 2.29 (s, 3H), 1.76-1.87 (m, 1H).

Step 8

(S)-allyl tert-butyl (2-(2-methylbenzyl)propane-1,3-diyl)dicarbamate

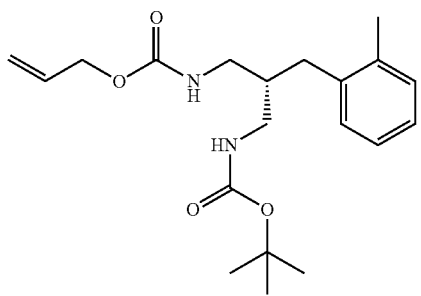 [SMILES: C=CCOC(=O)NC[C@@H](CNC(=O)OC(C)(C)C)Cc1ccccc1C]

To a 50 L vessel under nitrogen was added (R)-Allyl (3-amino-2-(2-methylbenzyl)propyl) carbamate (1740 g) dissolved in MTBE (29.4 L). This was followed by the addition of triethylamine (922 mL). The mixture was cooled to 0° C. and treated with BOC-anhydride (1600 mL, 1518 g) dissolved in MTBE (3.48 L). The reaction was warmed to 20° C. and stirred for 2 h. The reaction was judged complete by $^1$H NMR. The reaction was charged with water (8.7 L) and stirred for 15 min. The organics were separated and washed with 5% citric acid (8.7 L) and brine (8.7 L) before drying over magnesium sulphate, filtering and concentrating in vacuo affording the title compound (2320 g, 94%). $^1$H NMR indicated a purity of >90%.

$^1$H NMR (CDCl$_3$, 270 MHz) δ 7.02-7.10 (m, 4H), 5.82-5.99 (m, 1H), 5.55 (t, 1H), 5.32-5.15 (m, 2H), 5.02 (t, 1H), 4.52 (d, 2H), 3.17-3.30 (m, 2H), 2.95-3.15 (m, 2H), 2.51 (d, 2H), 2.28 (s, 3H0, 1.87-1.95 (m, 1H), 1.43 (s, 9H).

Step 9

(S)-tert-butyl (3-amino-2-(2-methylbenzyl)propyl) carbamate

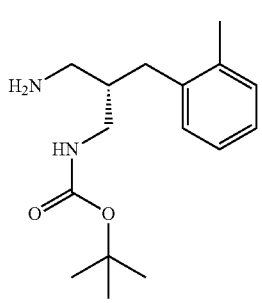 [SMILES: Cc1ccccc1C[C@@H](CN)CNC(=O)OC(C)(C)C]

To a 50 L vessel under nitrogen was added (S)-allyl tert-butyl (2-(2-methylbenzyl)propane-1,3-diyl)dicarbamate (2330 g) dissolved in DCM (12.9 L) and MeOH (10.3 L), this was followed by the addition of Pd(PPh$_3$)$_4$ (148.4 g).

The reaction mixture was cooled to 5° C. and charged with NaBH$_4$ (729 g) in portions over a period of 2 h. The reaction was warmed to 20° C. and stirred for 2 h, The reaction mixture was carefully quenched into water (46.6 L) and then stirred for 20 min. The organics were separated and the aqueous re-extracted with DCM (23.6 L). The combined organics were dried over magnesium sulfate, filtered and concentrated in vacuo to give the title compound (1679 g, 100% yield (~80% pure by $^1$H NMR).

$^1$H NMR (CDCl$_3$, 270 MHz) δ 7.02-7.15 (m, 4H), 5.22 (br s, 1H), 3.10-3.28 (m, 2H), 2.62-2.80 (m, 2H), 2.52 (d, 2H), 2.29 (s, 3H), 1.75-1.82 (m, 1H), 1.92 (s, 9H), 1.30 (br s, 2H).

Step 10

(S)-tert-butyl (3-(3,5-diamino-6-chloropyrazine-2-carboxamido)-2-(2-methylbenzyl)propyl) carbamate

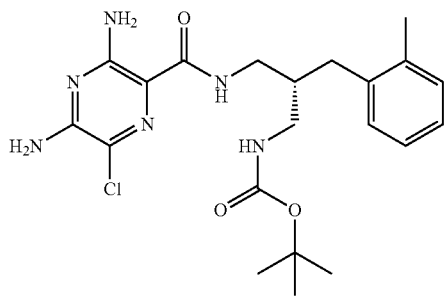 [SMILES: Cc1ccccc1C[C@H](CNC(=O)OC(C)(C)C)CNC(=O)c1nc(Cl)c(N)nc1N]

To a 5 L vessel under nitrogen was added 3,5-diamino-6-chloropyrazine-2-carboxylic acid (100 g), HBTU (202.8 g), THF (1200 mL) and DIPEA (111 mL). The reaction was allowed to stir for 24 h at room temperature. To the reaction was added (S)-tert-butyl (3-amino-2-(2-methylbenzyl)propyl)carbamate (step 9, 148.6 g) dissolved in THF (1.49 L). It should be noted that the reaction exothermed by 10° C. during the addition. The reaction was allowed to stir for 24 h at room temperature, LCMS indicated 5% adduct remaining. The mixture was heated to 35° C. for 4 h. LC/MS indicated 2% adduct remaining. The reaction was stirred for a further 1 h before being cooled to room temperature and concentrated in vacuo. The residue was taken up in ethyl acetate (1.5 L) and MTBE (1.5 L) and washed with saturated NaHCO$_3$ (1 L), 5% citric acid (700 mL) and brine (700 mL). The organics were dried over magnesium sulfate, filtered and concentrated in vacuo. The residue was taken up in MTBE (1 L) and re-concentrated before being taken up in MTBE (500 mL) and diethyl ether (500 mL) and filtered to remove DIPEA salts. The filtrate was concentrated and analysis indicated some DIPEA salts remaining. The residue was re-triturated with MTBE (750 mL) and diethyl ether (750 mL) and again filtered. The filtrate was concentrated to give the title compound (225 g, 94% (accounting for solvent and TMU).

LC/MS: m/z 349.2 [M+H]$^+$ $^1$H NMR (CDCl$_3$, 270 MHz) δ 7.46 (t, 1H), 7.13 (m, 4H), 5.52 (t, 1H), 5.22 (br s, 2H), 3.62-3.75 (m, 1H), 3.00-3.40 (m, 5H), 2.80 (s, 3H), 2.49-2.75 (m, 2H), 1.95-2.02 (m, 1H), 1.42 (s, 9H).

Step 11

3,5-Diamino-N-[(2R)-3-amino-2-(2-methylbenzyl)propyl]-6-chloropyrazine-2-carboxamide

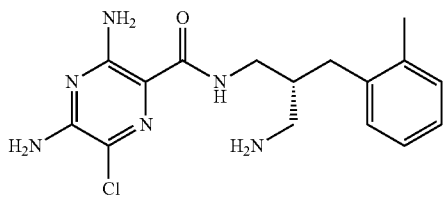 [SMILES: Cc1ccccc1C[C@H](CN)CNC(=O)c1nc(Cl)c(N)nc1N]

To a 20 L flange flask under nitrogen was added (S)-tert-butyl (3-(3,5-diamino-6-chloropyrazine-2-carboxamido)-2-(2-methylbenzyl)propyl) carbamate (step 10, 2215 g) in dioxane (6 L). The mixture was stirred for 20 min until complete dissolution. To the reaction was then added 4M HCl in dioxane (10 L). The reaction evolved a considerable amount of gas and the temperature rose to 35° C. before cooling was applied. A viscous oily precipitate was observed in the reaction. LC/MS of the reaction mixture after 1 h indicated complete reaction. The supernatant liquor were decanted off and concentrated in vacuo. The oily viscous solid was dissolved in water (6 L) and combined with the concentrated supernatant dissolved in water (2 L). The aqueous was washed with MTBE (5 L). The aqueous was then basified with 10 M NaOH (2 L) and extracted with 2-Me-THF (4×10 L). The organics were dried, filtered and concentrated in vacuo. The residue was then concentrated from MTBE (2×4 L) to remove residual 2-MeTHF. The solid was triturated with MTBE:heptane (9 L:1.8 L) and allowed to stir over the weekend. The solid was filtered and dried in the oven at 40° C. affording the title compound (1657 g, 96%).

$^1$H NMR (CDCl$_3$, 270 MHz) δ 7.60 (t, 1H), 7.08-7.15 (m, 4H), 5.75 (br s, 2H), 5.12 (b s, 2H), 3.38-3.45 (m, 2H), 2.52-2.82 (m, 4H), 2.30 (s, 3H), 1.80-1.98 (m, 2H), 1.20-1.28 (m, 2H).

Step 12

(R)-3,5-diamino-N-(3-amino-2-(2-methylbenzyl)propyl)-6-chloropyrazine-2-carboxamide (2R,3S)-2-benzoyl-3-(benzoyloxy)succinate

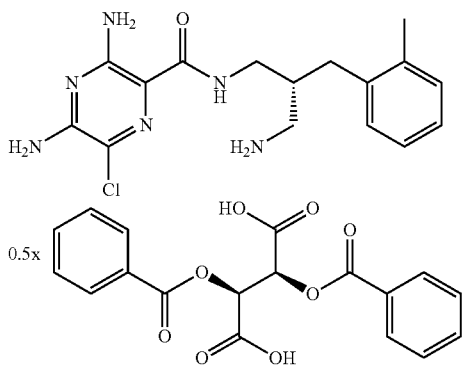

To a 5 L vessel under nitrogen was added 3,5-Diamino-N-[(2R)-3-amino-2-(2-methylbenzyl)propyl]-6-chloropyra-zine-2-carboxamide (127.4 g) and methanol (892 mL). The mixture was gently heated to 30° C. until all the solid had dissolved. The reaction was cooled to room temperature and (+)-dibenzoyl-D-tartaric acid (65.5 g) in methanol (458 mL) was added. The reaction was allowed to stir, after ~2 h solid began to precipitate. The reaction was allowed to stir over the weekend. Isopropyl acetate (1.5 L) was added to the mixture and and stirring was continued for 4 h. The precipitate was then filtered off and washed with isopropyl acetate (2×1 L). The solid was then dried in the oven for 3 d at 40° C. A total of 147.5 g (74%) was obtained in the stöchiometric ratio base/di-acid=2:1.

$^1$H NMR (CDCl$_3$, 270 MHz): δ 7.60 (t, 1H), 7.08-7.15 (m, 4H), 5.75 (br s, 2H), 5.12 (b s, 2H), 3.38-3.45 (m, 2H), 2.52-2.82 (m, 4H), 2.30 (s, 3H), 1.80-1.98 (m, 2H), 1.20-1.28 (m, 2H).

Chiral HPLC (method A): 98.7% ee, Rt=11.93 min (R), 14.24 min (S).

Step 13

(R)-3,5-diamino-N-(3-amino-2-(2-methylbenzyl)propyl)-6-chloropyrazine-2-carboxamide

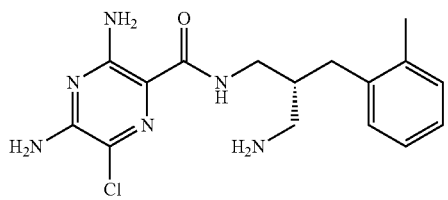 [SMILES: Cc1ccccc1C[C@H](CN)CNC(=O)c1nc(Cl)c(N)nc1N]

(R)-3,5-diamino-N-(3-amino-2-(2-methylbenzyl)propyl)-6-chloropyrazine-2-carboxamide (2R, 3S)-2-benzoyl-3-(benzoyloxy)succinate (20 g, 38.46 mmol) was suspended in 2-methyl-THF (200 mL) and water (200 mL) and cooled with an icebath. Sodium hydroxide, 1 M (42.3 mL, 42.31 mmol) was added slowly and the mixture was then stirred at 40° C. until all material had dissolved. The mixture was cooled to room temperature and the phases were separated. The aqueous phase was extracted with 2-methyl-THF (2×200 mL). The combined organic phases were washed with brine (200 mL), dried with a phase separator and evaporated in vacuo to yield (R)-3,5-diamino-N-(3-amino-2-(2-methylbenzyl)propyl)-6-chloropyrazine-2-carboxamide (13.3 g, 99%) as a pale solid.

LC/MS: m/z: 349.3 [M+H]$^+$.

1H NMR (500 MHz, DMSO-d6) δ 1.50 (bs, 2H), 1.76-1.87 (m, 1H), 2.26 (s, 3H), 2.4-2.49 (m, 2H), 2.52-2.62 (m, 2H), 3.18-3.28 (m, 2H), 6.95 (bs, 2H), 7.04-7.17 (m, 4H), 8.14 (t, 1H).

Chiral HPLC (method B): 99.3% ee, Rt=11.55 min (S), 13.28 min (R).

$[α]_D^{20}$: +11.8 (c 1.0, MeCN).

Intermediate B (S)-(9H-fluoren-9-yl)methyl 3-(3,5-diamino-6-chloropyrazine-2-carboxamido)-2-(2-methylbenzyl)propyl(piperidin-4-ylmethyl)carbamate

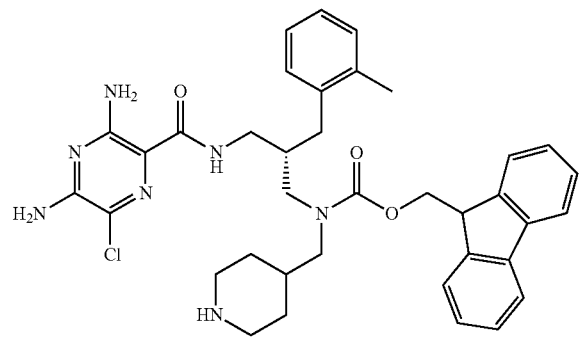 [SMILES: Cc1ccccc1C[C@@H](CNC(=O)c1nc(Cl)c(N)nc1N)CN(CC1CCNCC1)C(=O)OCC1c2ccccc2-c2ccccc21]

Step 1:

(R)-tert-butyl 4-((3-(3,5-diamino-6-chloropyrazine-2-carboxamido)-2-(2-methylbenzyl)propylamino)methyl)piperidine-1-carboxylate

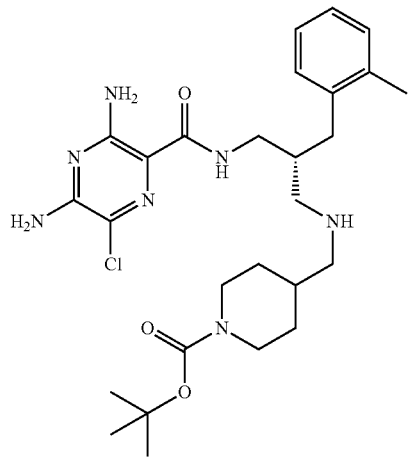 [SMILES: Cc1ccccc1C[C@H](CNCC1CCN(C(=O)OC(C)(C)C)CC1)CNC(=O)c1nc(Cl)c(N)nc1N]

Into a 50-mL round-bottom flask, was placed a mixture of tert-butyl 4-formylpiperidine-1-carboxylate (122 mg, 0.57 mmol, 1.00 equiv) and 3,5-diamino-N-[(2R)-3-amino-2-[(2-methylphenyl)methyl]propyl]-6-chloropyrazine-2-carboxamide (Intermediate A, 200 mg, 0.57 mmol, 1.0 equiv) in dichloromethane (5 mL), the mixture was stirred for 1 h. Then sodium triacetoxyborohydride (486 mg, 2.29 mmol, 4.00 equiv) was added. The resulting solution was stirred overnight at room temperature. The resulting mixture was washed with 3×10 mL of water, dried over anhydrous sodium sulfate and concentrated under vacuum. This resulted in 250 mg (80%) of the title compound as a yellow solid.

LC/MS: m/z: 546 [M+H]$^+$.

Step 2:

(S)-tert-butyl 4-(((((9H-fluoren-9-yl)methoxy)carbonyl)(3-(3,5-diamino-6-chloropyrazine-2-carboxamido)-2-(2-methylbenzyl)propyl)amino)methyl)piperidine-1-carboxylate

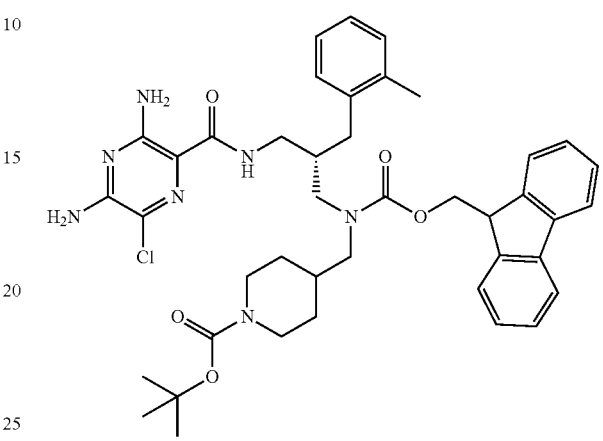

FMOC-chloride (19 mg, 0.07 mmol, 1.00 equiv) in dioxane (2.0 mL) was added dropwise to a mixture of (R)-tert-butyl 4-((3-(3,5-diamino-6-chloropyrazine-2-carboxamido)-2-(2-methylbenzyl)propylamino)methyl)piperidine-1-carboxylate (step 1, 40 mg, 0.07 mmol, 1.0 equiv) and Na$_2$CO$_3$ (12 mg, 0.11 mmol, 1.5 equiv) in water/dioxane (1:2, 3 mL). The resulting solution was stirred for 2 h at room temperature, extracted with 3×5 mL of ethyl acetate. The combined organic phases were dried over anhydrous sodium sulfate. After removal of the solvents in vacuo 42 mg (75%) of the title compound was obtained as a yellow solid.

LC/MS: m/z: 768 [M+H]$^+$

Step 3:

(S)-(9H-fluoren-9-yl)methyl 3-(3,5-diamino-6-chloropyrazine-2-carboxamido)-2-(2-methylbenzyl)propyl(piperidin-4-ylmethyl)carbamate

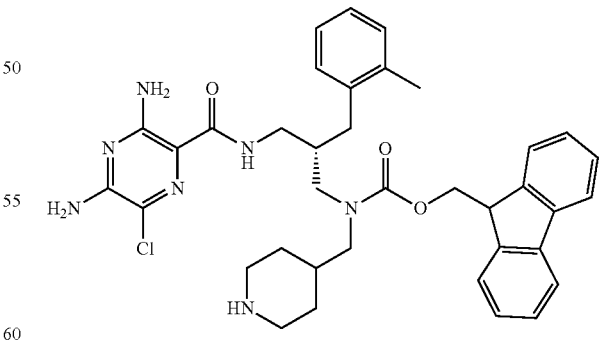

Into a 25-mL round-bottom flask was placed a solution of (S)-tert-butyl 4-(((((9H-fluoren-9-yl)methoxy)carbonyl)(3-(3,5-diamino-6-chloropyrazine-2-carboxamido)-2-(2-methylbenzyl)propyl)amino)methyl)piperidine-1-carboxylate (step 2, 20 mg, 0.03 mmol, 1.0 equiv) in HCl/MeOH (4M, 3 mL). The resulting solution was stirred for 1 h at room temperature. The resulting mixture was concentrated under vacuum. This resulted in 15 mg (86%) of 9H-fluoren-9-ylmethyl N-[(2S)-3-[(3,5-diamino-6-chloropyrazin-2-yl)formamido]-2-[(2-methylphenyl)methyl]propyl]-N-(piperidin-4-ylmethyl)carbamate as a yellow solid.

LC/MS: m/z: 668 [M+H]+

Intermediate C (9H-fluoren-9-yl)methyl (2-aminoethyl)(hexyl)carbamate Hydrochloride

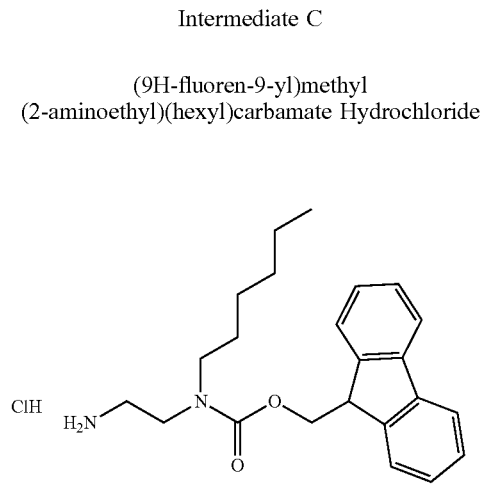

Step 1 tert-butyl (2-(benzyl(hexyl)amino)ethyl)carbamate

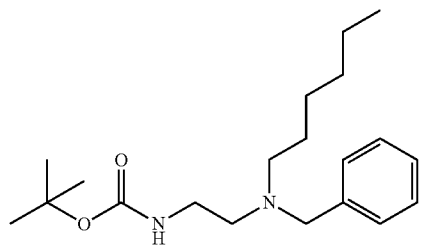 [SMILES: CCCCCCN(CCNC(=O)OC(C)(C)C)Cc1ccccc1]

N-benzylhexan-1-amine (2.69 g, 14.1 mmol), tert-butyl (2-oxoethyl)carbamate (4.48 g, 28.1 mmol) and DIPEA (2.46 mL, 14.1 mmol) was dissolved in MeOH (20 mL) and stirred at room temperature for 45 min. Sodium cyanoborohydride (1.77 g, 28.1 mmol) and acetic acid (0.806 mL, 14.1 mmol) were added and stirring continued for 18 h. The reaction was quenched by addition of 8% NaHCO$_3$ (aq) and stirred at room temperature for 1 h. The solvent was concentrated in vacuo. The residue was diluted with water and extracted with EtOAc (2×100 mL). The combined organic phases were dried with Na2SO4 (s), filtered and evaporated in vacuo. The residue was purified by automated flash chromatography on two Biotage® KP-SIL 100 g columns. A gradient from 5-50% of EtOAc in heptane over 12 CV was used as mobile phase. The product was collected and evaporated in vacuo to yield tert-butyl (2-(benzyl(hexyl)amino)ethyl)carbamate (3.19 g, 68%) as a colorless oil.

LC/MS: m/z: 335.6 [M+H]+

1H NMR (500 MHz, CDCl$_3$) δ 0.84-0.92 (m, 3H), 1.19-1.35 (m, 6H), 1.38-1.66 (m, 11H), 2.43 (t, 2H), 2.52 (t, 2H), 3.09-3.21 (m, 2H), 3.56 (s, 2H), 4.83-4.93 (m, 1H), 7.22-7.37 (m, 5H).

Step 2 tert-butyl (2-(hexylamino)ethyl)carbamate

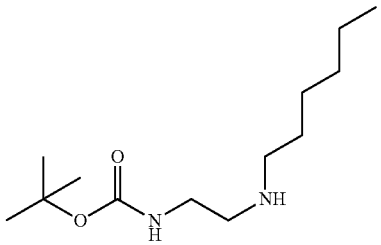 [SMILES: CCCCCCNCCNC(=O)OC(C)(C)C]

tert-butyl (2-(benzyl(hexyl)amino)ethyl)carbamate (3.19 g, 9.54 mmol) was dissolved in MeOH (25 mL) and 20% Pd(OH)$_2$/C (0.201 g, 0.29 mmol) added. The reaction was hydrogenated in a Buchi hydrogenator at 4 bar and room temperature for 18 h. The reaction had stopped. More 20% Pd(OH)$_2$/C (200 mg, 0.28 mmol) was added and hydrogenation continued for 6 h, hydrogenation had stopped. The catalyst was filtered off, washed with MeOH and the filtrate concentrated in vacuo. The residue was dissolved in MeOH (15 mL), 20% Pd(OH)$_2$/C (250 mg, 0.36 mmol) was added and hydrogenation continued at 4 bar and room temperature for 16 h. The catalyst was filtered off, washed with MeOH and the filtrate evaporated in vacuo. The reaction was once again dissolved in MeOH, 20% Pd(OH)$_2$/C (250 mg, 0.36) added and hydrogenation continued for 3 days. The catalyst was filtered off, washed with MeOH and the filtrate evaporated in vacuo to yield tert-butyl (2-(hexylamino)ethyl)carbamate (2.38 g, 102%) as a colorless oil.

$^1$H NMR (500 MHz, CDCl$_3$) δ 0.89 (t, 3H), 1.22-1.36 (m, 6H), 1.41-1.53 (m, 11H), 2.61 (t, 2H), 2.75 (t, 2H), 3.19-3.28 (m, 2H), 4.97 (bs, 1H).

Step 3

(9H-fluoren-9-yl)methyl (2-((tert-butoxycarbonyl)amino)ethyl)(hexyl)carbamate

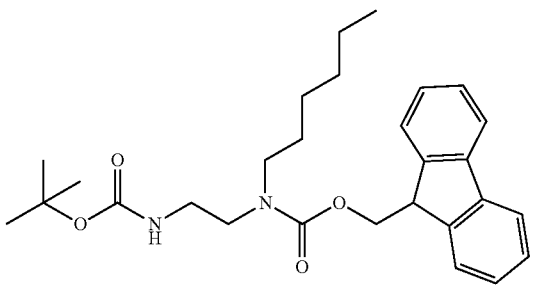 [SMILES: CCCCCCN(CCNC(=O)OC(C)(C)C)C(=O)OCC1c2ccccc2-c2ccccc21]

To an icebath cooled solution of tert-butyl (2-(hexylamino)ethyl)carbamate (2.38 g, 9.74 mmol) in DCM (40 mL) were added DIPEA (1.79 mL, 10.2 mmol) and (9H-fluoren-9-yl)methyl carbonochloridate (2.65 g, 10.2 mmol). The reaction was stirred with cooling for 10 min and then at room temperature for 1 h. Water (20 mL) was added, shaken and the phases separated. The aqueous phase was extracted with DCM (2×20 mL). The combined organic phases were dried with a phase separator and evaporated in vacuo. The residue was purified by automated flash chromatography on a Biotage® KP-SIL 100 g column. A gradient from 5-30% of EtOAc in heptane over 9 CV followed by 30% EtOAc in heptane over 3 CV were used as mobile phase. The product was collected using the wavelength 264 nm. The collected fractions were evaporated in vacuo to yield (9H-fluoren-9-yl)methyl (2-((tert-butoxycarbonyl)amino)ethyl)(hexyl)carbamate (3.70 g, 81%) as a colorless oil.

LC/MS: m/z: 467.4 [M+H]+

$^1$H NMR (500 MHz, CDCl$_3$) δ 0.89 (t, 3H), 1.06-1.36 (m, 8H), 1.43 (s, 9H), 2.78-2.87 (m, 1H), 2.95-3.08 (m, 2H), 3.11-3.36 (m, 3H), 4.18-4.26 (m, 1H), 4.49-4.63 (m, 2H), 4.89 (bs, 1H), 7.3-7.36 (m, 2H), 7.41 (t, 2H), 7.59 (d, 2H), 7.77 (d, 2H).

Step 4

(9H-fluoren-9-yl)methyl (2-aminoethyl)(hexyl)carbamate Hydrochloride

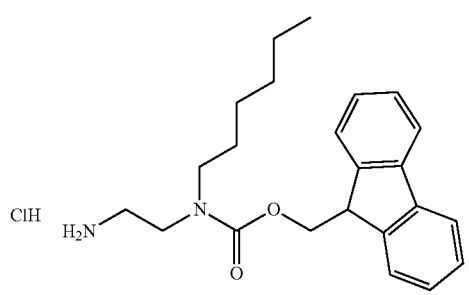 [SMILES: Cl ; CCCCCCN(CCN)C(=O)OCC1c2ccccc2-c2ccccc21]

Acetyl chloride (2.84 mL, 40.0 mmol) was added dropwise to an icebath cooled vial of MeOH (10 mL, 247 mmol) and stirred for 5 min. This solution was then added to (9H-fluoren-9-yl)methyl (2-((tert-butoxycarbonyl)amino)ethyl)(hexyl)carbamate (3.7 g, 7.93 mmol) and the reaction stirred at room temperature for 2.5 h. The solvent was concentrated in vacuo to yield (9H-fluoren-9-yl)methyl (2-aminoethyl)(hexyl)carbamate hydrochloride (2.92 g, 91%) as a white solid.

LC/MS: m/z: 367.3 [M+H]+

1H NMR (400 MHz, DMSO-d6) δ 0.82-0.97 (m, 4H), 0.99-1.51 (m, 7H), 2.68-2.88 (m, 3H), 3.23-3.39 (m, 3H), 4.23-4.4 (m, 2H), 4.52 (d, 1H), 7.29-7.37 (m, 2H), 7.37-7.46 (m, 2H), 7.64 (d, 2H), 7.83-8.09 (m, 5H).

Intermediate D (S)-tert-butyl (3-(3,5-diamino-6-chloropyrazine-2-carboxamido)-2-(2-methylbenzyl)propyl)(4-((2-(hexylamino)ethyl)carbamoyl)phenethyl)carbamate

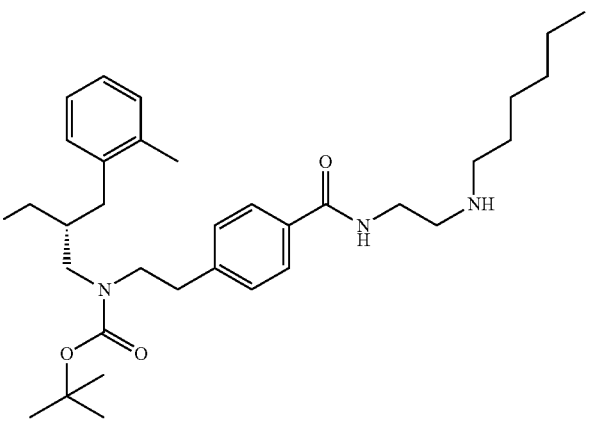

Step 1

Methyl 4-(2-hydroxyethyl)benzoate

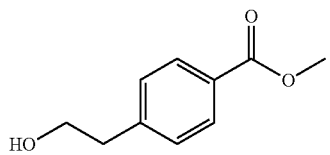

4-(2-Hydroxyethyl)benzoic acid (2.41 g, 14.5 mmol) was dissolved in MeOH (5 mL) and H$_2$SO$_4$ (0.06 mL, 1.13 mmol) added. The reaction was heated in a microwave at 120° C. for 1 h and was then evaporated in vacuo. The residue was dissolved in EtOAc (150 mL), washed with 8% NaHCO3 (aq) (150 mL), brine (50 mL), dried with a phase separator and evaporated in vacuo to yield methyl 4-(2-hydroxyethyl)benzoate (2.41 g, 92%) as a pale oil.

LC/MS: m/z: 181.0 [M+H]+

1H NMR (500 MHz, CDCl$_3$) δ 2.94 (t, 2H), 3.88-3.94 (m, 5H), 7.32 (d, 2H), 7.97-8.02 (m, 2H).

Step 2

Methyl 4-(2-oxoethyl)benzoate

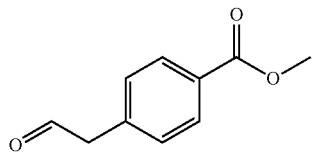

Methyl 4-(2-hydroxyethyl)benzoate (2.41 g, 13.37 mmol) was dissolved in DCM (50 mL) and Dess-Martin Periodinane (6.24 g, 14.7 mmol) added. The reaction was stirred at room temperature for 2 h and was then quenched by addition of 15% Na2S2O3/NaHCO3 3:2 (aq) (50 mL) and stirred vigorously for 30 min. The phases were separated and the aqueous phase extracted with DCM (2×50 mL). The combined organic phases were dried with a phase separator and evaporated in vacuo. The residue was purified by automated flash chromatography on a Biotage® KP-SIL 100 g column. A gradient from 5-40% of EtOAc in heptane over 9 CV followed by 50% EtOAc in heptane over 3 CV were used as mobile phase. The product was collected using the wavelength 245 nm. The product was collected and evaporated in vacuo to yield methyl 4-(2-oxoethyl)benzoate (0.880 g, 36.9%) as a yellow solid.

1H NMR (500 MHz, CDCl$_3$) δ 3.78 (d, 2H), 3.93 (s, 3H), 7.29-7.34 (m, 2H), 8.03-8.09 (m, 2H), 9.79 (t, 1H).

Step 3

(S)-Methyl 4-(2-((tert-butoxycarbonyl)(3-(3,5-diamino-6-chloropyrazine-2-carboxamido)-2-(2-methylbenzyl)propyl)amino)ethyl)benzoate

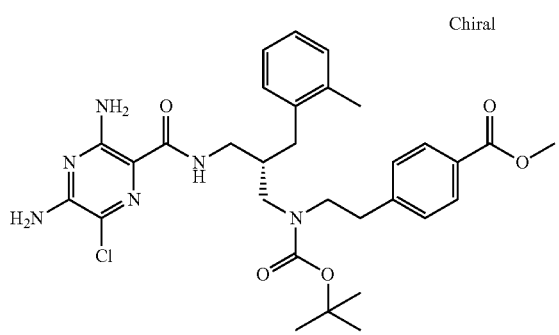 [SMILES: COC(=O)c1ccc(CCN(C[C@H](CNC(=O)c2nc(Cl)c(N)nc2N)Cc2ccccc2C)C(=O)OC(C)(C)C)cc1]

(R)-3,5-Diamino-N-(3-amino-2-(2-methylbenzyl)propyl)-6-chloropyrazine-2-carboxamide (Intermediate A, 2.00 g, 5.56 mmol), methyl 4-(2-oxoethyl)benzoate (1.09 g, 6.12 mmol) and DIPEA (0.971 mL, 5.56 mmol) were dissolved in MeOH (4 mL) and stirred at room temperature for 30 min. Sodium cyanoborohydride (1.05 g, 16.7 mmol) and acetic acid (0.318 mL, 5.56 mmol) were then added and the reaction stirred at room temperature for 3 h. The reaction was quenched by addition of 8% NaHCO$_3$ (aq). The reaction was diluted with EtOAc (100 mL), stirred for 30 min and the phases separated. The aqueous phase was extracted with EtOAc (100 mL). The combined organic phases were washed with brine (50 mL), dried with a phase separator and evaporated in vacuo. The residue was dissolved in DCM (20 mL) and BOC$_2$O (1.290 mL, 5.56 mmol) added. The mixture was stirred at room temperature for 5.5 h and was then concentrated in vacuo. The residue was purified by automated flash chromatography on a Biotage® KP-SIL 100 g column. A gradient from 10-80% of EtOAc in heptane over 10 CV was used as mobile phase. The product was collected using the wavelength 270 nm. The product peak were collected and evaporated in vacuo to yield (S)-methyl 4-(2-((tert-butoxycarbonyl)(3-(3,5-diamino-6-chloropyrazine-2-carboxamido)-2-(2-methylbenzyl)propyl)amino)ethyl)benzoate (1.84 g, 54%) as a pale solid.

LC/MS: m/z: 611.4 [M+H]$^+$ $^1$H NMR (500 MHz, DMSO-d$_6$) δ 1.36 (d, 9H), 2.15-2.26 (m, 4H), 2.45-2.49 (m, 2H), 2.75 (t, 2H), 2.93 (dd, 1H), 3.01-3.4 (m, 5H), 3.84 (s, 3H), 6.97 (bs, 2H), 7.05-7.17 (m, 4H), 7.21 (d, 2H), 7.82 (d, 2H), 7.85-7.94 (m, 1H).

Step 4

(S)-4-(2-((tert-butoxycarbonyl)(3-(3,5-diamino-6-chloropyrazine-2-carboxamido)-2-(2-methylbenzyl)propyl)amino)ethyl)benzoic Acid

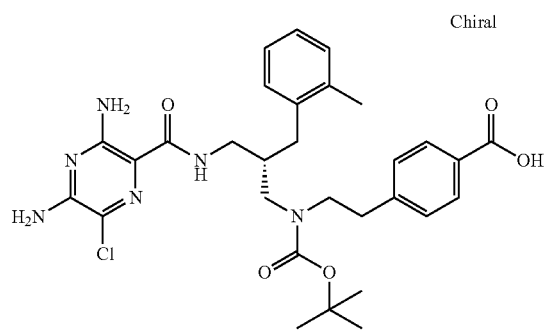 [SMILES: Cc1ccccc1C[C@@H](CNC(=O)c1nc(Cl)c(N)nc1N)CN(CCc1ccc(C(=O)O)cc1)C(=O)OC(C)(C)C]

(S)-Methyl 4-(2-((tert-butoxycarbonyl)(3-(3,5-diamino-6-chloropyrazine-2-carboxamido)-2-(2-methylbenzyl)propyl)amino)ethyl)benzoate (1.84 g, 2.56 mmol) was dissolved in MeOH (20 mL) and sodium hydroxide (3.37 mL, 12.8 mmol) added. The reaction was stirred at room temperature for 3 days. The solvent (MeOH) was then concentrated in vacuo. Water (50 mL) and MeTHF (50 mL) were added and the pH adjusted to ~2 with 3 M HCl (aq). The phases were separated and the aqueous phase extracted with L-MeTHF (50 mL). The combined organic phases were dried with Na2SO4 (s), filtered and evaporated in vacuo to yield (S)-4-(2-((tert-butoxycarbonyl)(3-(3,5-diamino-6-chloropyrazine-2-carboxamido)-2-(2-methylbenzyl)propyl)amino)ethyl)benzoic acid (1.53 g, 100%) as a pale solid.

LC/MS: m/z: 597.4 [M+H]$^+$

1H NMR (400 MHz, DMSO-d6) δ 1.33 (s, 9H), 2.21 (d, 4H), 2.38-2.49 (m, 2H), 2.73 (t, 2H), 2.83-3.43 (m, 6H), 6.84-7.26 (m, 8H), 7.78-7.98 (m, 3H), 12.80 (bs, 1H).

Step 5

(S)-tert-Butyl 4-((2-((((9H-fluoren-9-yl)methoxy)carbonyl)(hexyl)amino)ethyl)carbamoyl)phenethyl (3-(3,5-diamino-6-chloropyrazine-2-carboxamido)-2-(2-methylbenzyl)propyl)carbamate

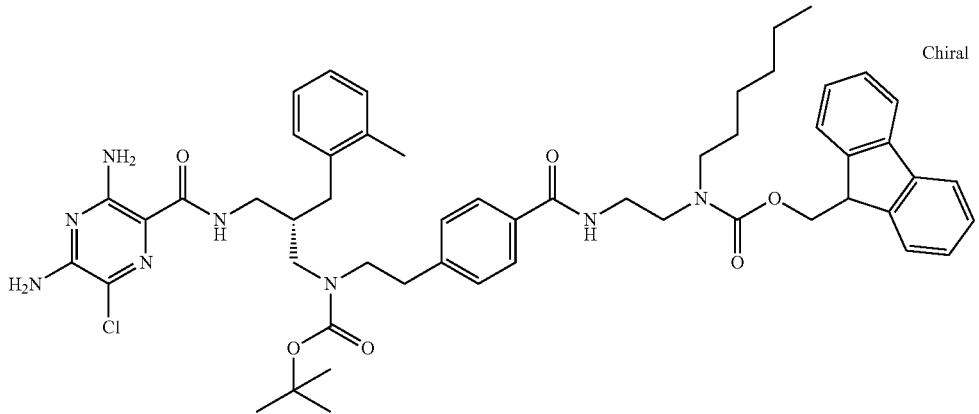 [SMILES: CCCCCCN(CCNC(=O)c1ccc(CCN(C[C@H](CNC(=O)c2nc(Cl)c(N)nc2N)Cc2ccccc2C)C(=O)OC(C)(C)C)cc1)C(=O)OCC1c2ccccc2-c2ccccc21]

(S)-4-(2-((tert-Butoxycarbonyl)(3-(3,5-diamino-6-chloropyrazine-2-carboxamido)-2-(2-methylbenzyl)propyl)amino)ethyl)benzoic acid (1.24 g, 1.77 mmol), 2-(1H-benzo[d][1,2,3]triazol-1-yl)-1,1,3,3-tetramethylisouronium tetrafluoroborate (0.623 g, 1.94 mmol) and DIPEA (1.54 mL, 8.83 mmol) were dissolved in DCM (30 mL) and stirred at room temperature for 5 min before addition of (9H-fluoren-9-yl)methyl (2-aminoethyl)(hexyl)carbamate hydrochloride (Intermediate C, 0.95 g, 2.12 mmol). The reaction was stirred for 2.5 h. The reaction was washed with 8% NaHCO3 (aq) (150 mL). The aqueous phase was extracted with DCM (150 mL). The combined organic phases were dried with a phase separator and evaporated in vacuo. The residue was purified by automated flash chromatography on a Biotage® KP-SIL 100 g column. A gradient from 20-80% of EtOAc in heptane over 9 CV followed by 80% EtOAc in heptane over 3 CV were used as mobile phase. The product was collected and evaporated in vacuo to yield (S)-tert-butyl 4-((2-((((9H-fluoren-9-yl)methoxy)carbonyl)(hexyl)amino)ethyl)carbamoyl)phenethyl(3-(3,5-diamino-6-chloropyrazine-2-carboxamido)-2-(2-methylbenzyl)propyl)carbamate (1.56 g, 93%) as a pale solid.

LC/MS: m/z: 945.6 [M+H]+

$^1$H NMR (500 MHz, DMSO-d$_6$) δ 0.82 (t, 3H), 0.87-0.97 (m, 2H), 1-1.27 (m, 5H), 1.33 (s, 9H), 1.38-1.47 (m, 1H), 2.15-2.27 (m, 4H), 2.45 (dd, 1H), 2.69 (s, 2H), 2.81-2.89 (m, 1H), 2.9-3 (m, 1H), 3.01-3.41 (m, 11H), 4.15-4.27 (m, 2H), 4.48 (d, 1H), 6.96 (bs, 2H), 7.05-7.18 (m, 6H), 7.30 (t, 2H), 7.39 (t, 2H), 7.55-7.65 (m, 2H), 7.71 (dd, 2H), 7.8-7.97 (m, 3H), 8.37-8.51 (m, 1H).

Step 6

(S)-tert-butyl (3-(3,5-diamino-6-chloropyrazine-2-carboxamido)-2-(2-methylbenzyl)propyl)(4-((2-(hexylamino)ethyl)carbamoyl)phenethyl)carbamate

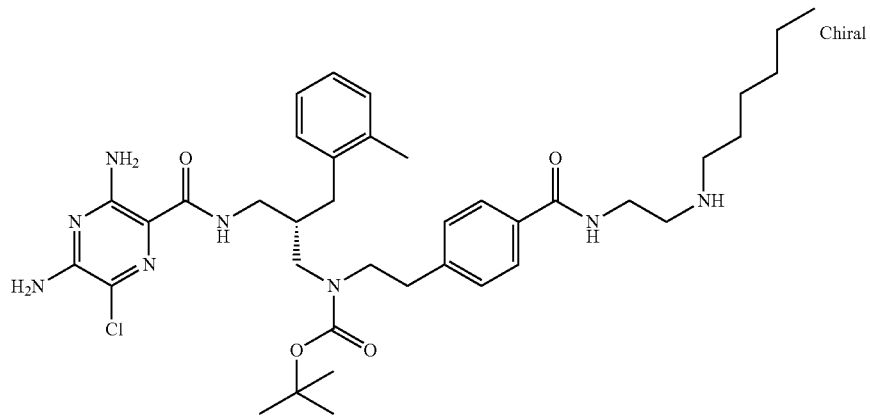 [SMILES: CCCCCCNCCNC(=O)c1ccc(CCN(C[C@H](CNC(=O)c2nc(Cl)c(N)nc2N)Cc2ccccc2C)C(=O)OC(C)(C)C)cc1]

(S)-tert-butyl 4-((2-((((9H-fluoren-9-yl)methoxy)carbonyl)(hexyl)amino)ethyl)carbamoyl)phenethyl(3-(3,5-diamino-6-chloropyrazine-2-carboxamido)-2-(2-methylbenzyl)propyl)carbamate (1.59 g, 1.68 mmol) was dissolved in THF (15 mL) and piperidine (1.67 mL, 16.8 mmol) added. The reaction was stirred at room temperature for 3 h and was then concentrated in vacuo. The residue was purified by automated flash chromatography on a Biotage® KP-SIL 100 g column. A gradient from 4-8% of (2 M ammonia in MeOH) in DCM over 5 CV followed by 8% of (2 M ammonia in MeOH) in DCM over 10 CV were used as mobile phase. The product was collected and evaporated in vacuo to yield (S)-tert-butyl (3-(3,5-diamino-6-chloropyrazine-2-carboxamido)-2-(2-methylbenzyl)propyl) (4-((2-(hexylamino)ethyl)carbamoyl)phenethyl)carbamate (1.03 g, 85%) as a pale solid.

LC/MS: m/z: 723.6 [M+H]+

1H NMR (500 MHz, DMSO-d6) δ 0.84 (t, 3H), 1.19-1.44 (m, 17H), 2.15-2.29 (m, 4H), 2.45 (dd, 1H), 2.54 (t, 2H), 2.65-2.75 (m, 4H), 2.94 (dd, 1H), 3.02-3.18 (m, 2H), 3.18-3.3 (m, 3H), 3.3-3.4 (m, 4H), 6.97 (bs, 2H), 7.05-7.2 (m, 7H), 7.73 (d, 2H), 7.79-7.97 (m, 1H), 8.32 (t, 1H).

Intermediate E (S)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate

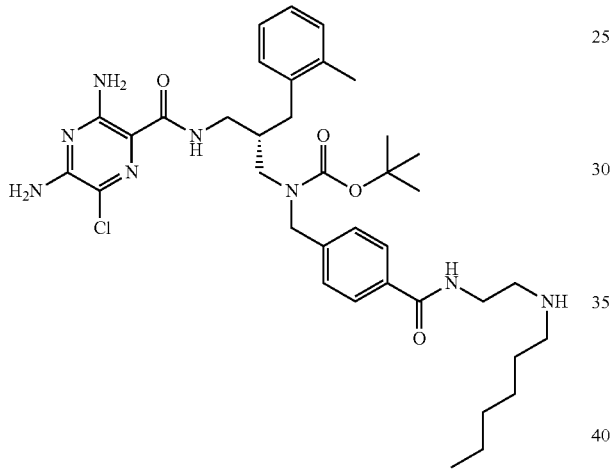

Step 1

(S)-methyl 4-(((tert-butoxycarbonyl)(3-(3,5-diamino-6-chloropyrazine-2-carboxamido)-2-(2-methylbenzyl)propyl)amino)methyl)benzoate

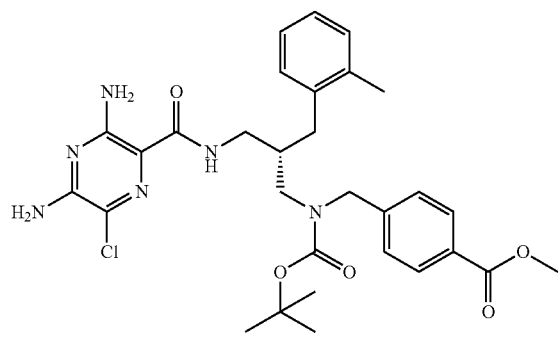 [SMILES: COC(=O)c1ccc(CN(C[C@H](CNC(=O)c2nc(Cl)c(N)nc2N)Cc2ccccc2C)C(=O)OC(C)(C)C)cc1]

(R)-3,5-diamino-N-(3-amino-2-(2-methylbenzyl)propyl)-6-chloropyrazine-2-carboxamide (Intermediate A, 2.17 g, 6.22 mmol), methyl 4-formylbenzoate (1.12 g, 6.84 mmol) and DIPEA (1.09 mL, 6.22 mmol) were dissolved in MeOH (15 mL) and stirred at room temperature for 1 h. Sodium cyanoborohydride (0.782 g, 12.4 mmol) and acetic acid (0.392 mL, 6.84 mmol) were then added and the reaction stirred at room temperature for 3 h. When monitoring by LCMS analysis showed uncomplete conversion, methyl 4-formylbenzoate (200 mg, 1.22 mmol) was added and stirring was continued for 3 h. Then again methyl 4-formylbenzoate (200 mg, 1.22 mmol) and sodium cyanoborohydride (200 mg, 3.18 mmol) were added and stirring was continued for 18 h. The reaction was quenched by addition of 8% NaHCO3 (aq). The solvent was concentrated in vacuo. The residue was dissolved in EtOAc (250 mL) and 8% NaHCO₃ (aq) 250 mL), shaken and the phases separated. The aqueous phase was extracted with EtOAc (250 mL). The combined organic phases were dried with Na2SO4 (s), filtered and evaporated in vacuo. The residue was dissolved in DCM (50 mL), BOC₂O (1.63 g, 7.46 mmol) added and the reaction stirred at room temperature for 2 h. The mixture was concentrated in vacuo and was then purified by automated flash chromatography on a Biotage® KP-SIL 100 g column. A gradient from 20-80% of EtOAc in heptane over 12 CV was used as mobile phase. The product was collected using the wavelength 265 nm. The product peak was evaporated in vacuo to yield (S)-methyl 4-(((tert-butoxycarbonyl)(3-(3,5-diamino-6-chloropyrazine-2-carboxamido)-2-(2-methylbenzyl)propyl)amino)methyl)benzoate (2.85 g, 77%) as a solid.

LC/MS: m/z: 597.5 [M+H]+

1H NMR (500 MHz, DMSO-d6) δ 1.36 (d, 9H), 2.21 (s, 3H), 2.24-2.38 (m, 1H), 2.45-2.57 (m, 2H), 2.95-3.3 (m, 4H), 3.83 (s, 3H), 4.33-4.51 (m, 2H), 6.97 (bs, 2H), 7.04-7.17 (m, 4H), 7.22 (d, 2H), 7.76-7.96 (m, 3H).

Step 2

(S)-4-(((tert-butoxycarbonyl)(3-(3,5-diamino-6-chloropyrazine-2-carboxamido)-2-(2-methylbenzyl)propyl)amino)methyl)benzoic Acid

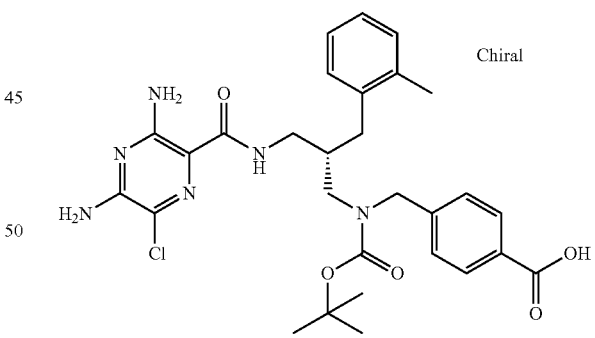

(S)-methyl 4-(((tert-butoxycarbonyl)(3-(3,5-diamino-6-chloropyrazine-2-carboxamido)-2-(2-methylbenzyl)propyl)amino)methyl)benzoate (2.85 g, 4.77 mmol) was dissolved MeOH (40 mL) and sodium hydroxide, 3.8 M (6.28 mL, 23.9 mmol) added. The reaction was stirred at room temperature for 24 h and the solvent (MeOH) was then concentrated in vacuo. Water (75 mL) and MeTHF (75 mL) were added and the pH adjusted to ~2 with 3 M HCl (aq). The phases were separated and the aqueous phase extracted with MeTHF (75 mL). The combined organic phases were dried with a phase separator and evaporated in vacuo to yield (S)-4-(((tert-butoxycarbonyl)(3-(3,5-diamino-6-chloropyrazine-2-carboxamido)-2-(2-methylbenzyl)propyl)amino)
methyl)benzoic acid (2.75 g, 99%) as a solid.

LC/MS: m/z: 583.4 [M+H]+

1H NMR (500 MHz, DMSO-d6) δ 1.32-1.42 (m, 9H), 2.20 (s, 3H), 2.24-2.38 (m, 1H), 2.5-2.55 (m, 2H), 2.92-3.36 (m, 4H), 4.27-4.54 (m, 2H), 6.97 (bs, 2H), 7.03-7.17 (m, 4H), 7.19 (d, 2H), 7.78-8 (m, 3H), 12.85 (bs, 1H).

Step 3

(S)-tert-butyl 4-((2-((((9H-fluoren-9-yl)methoxy)carbonyl)(hexyl)amino)ethyl)carbamoyl)benzyl(3-(3,5-diamino-6-chloropyrazine-2-carboxamido)-2-(2-methylbenzyl)propyl)carbamate

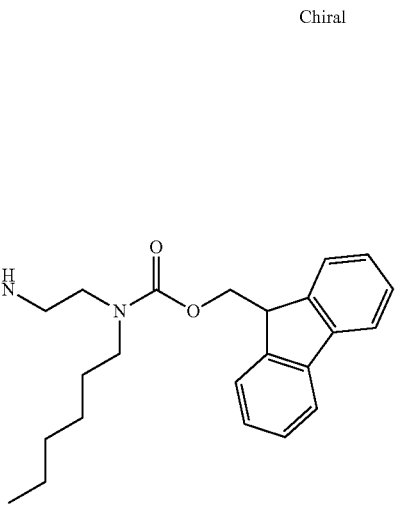

(S)-4-(((tert-butoxycarbonyl)(3-(3,5-diamino-6-chloropyrazine-2-carboxamido)-2-(2-methylbenzyl)propyl)amino)methyl)benzoic acid (1.61 g, 2.76 mmol), 2-(1H-benzo[d][1,2,3]triazol-1-yl)-1,1,3,3-tetramethylisouronium tetrafluoroborate (0.975 g, 3.04 mmol) and DIPEA (2.41 mL, 13.8 mmol) were dissolved in DCM (150 mL) and stirred at room temperature for 5 min before addition of (9H-fluoren-9-yl)methyl (2-aminoethyl)(hexyl)carbamate hydrochloride (Intermediate C, 1.48 g, 3.31 mmol). The reaction was stirred for 1.5 h. The reaction was washed with 8% NaHCO3 (aq) (100 mL). The aqueous phase was extracted with DCM (100 mL). The combined organic phases were dried with a phase separator and evaporated in vacuo. The residue was purified by automated flash chromatography on a Biotage® KP-SIL 100 g column. A gradient from 20-80% of EtOAc in heptane over 12 CV followed by 80% EtOAc in heptane over 3 CV were used as mobile phase. The product was collected and evaporated in vacuo to yield (S)-tert-butyl 4-((2-((((9H-fluoren-9-yl) methoxy)carbonyl)(hexyl)amino)ethyl)carbamoyl)benzyl (3-(3,5-diamino-6-chloropyrazine-2-carboxamido)-2-(2-methylbenzyl)propyl)carbamate (2.38 g, 93%) as a pale solid.

LC/MS: m/z: 931.5 [M+H]+

1H NMR (500 MHz, DMSO-d6) δ 0.82 (t, 3H), 0.86-0.96 (m, 1H), 0.99-1.27 (m, 6H), 1.27-1.48 (m, 10H), 2.19 (s, 3H), 2.23-2.35 (m, 1H), 2.45-2.54 (m, 2H), 2.8-2.9 (m, 1H), 2.9-3.05 (m, 1H), 3.05-3.38 (m, 8H), 4.16-4.32 (m, 3H), 4.39-4.56 (m, 2H), 6.97 (bs, 2H), 7.02-7.18 (m, 6H), 7.30 (t, 2H), 7.39 (t, 2H), 7.60 (t, 2H), 7.64-7.76 (m, 2H), 7.78-7.99 (m, 3H), 8.37-8.52 (m, 1H).

Step 4

(S)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate

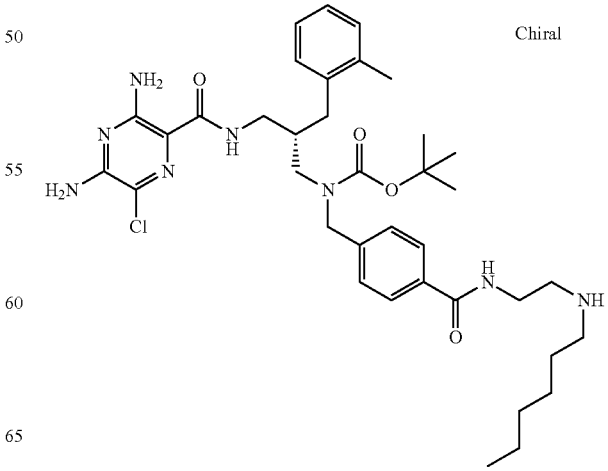

(S)-tert-butyl 4-((2-((((9H-fluoren-9-yl)methoxy)carbonyl)(hexyl)amino)ethyl)carbamoyl)benzyl(3-(3,5-diamino-6-chloropyrazine-2-carboxamido)-2-(2-methylbenzyl)propyl)carbamate (2.38 g, 2.55 mmol) was dissolved in THF (25 mL) and piperidine (2.53 mL, 25.6 mmol) added. The reaction was stirred at room temperature for 20 h. The solvent was evaporated in vacuo. The residue was purified by automated flash chromatography on a Biotage® KP-SIL 100 g column. A gradient from 2.5-8% of (2 M ammonia in MeOH) in DCM over 9 CV followed by 8% of (2 M ammonia in MeOH) in DCM over 3 CV were used as mobile phase. The product was collected and evaporated in vacuo to yield (S)-tert-butyl (3-(3,5-diamino-6-chloropyrazine-2-carboxamido)-2-(2-methylbenzyl)propyl) (4-((2-(hexylamino)ethyl)carbamoyl)benzyl)carbamate (1.60 g, 88%) as a pale solid.

LC/MS: m/z: 709.5 [M+H]$^+$

1H NMR (500 MHz, DMSO-d6) δ 0.84 (t, 3H), 1.17-1.31 (m, 6H), 1.31-1.45 (m, 11H), 2.20 (s, 3H), 2.24-2.37 (m, 1H), 2.51-2.57 (m, 3H), 2.68 (t, 2H), 2.91-3.06 (m, 1H), 3.06-3.4 (m, 6H), 4.23-4.36 (m, 1H), 4.4-4.53 (m, 1H), 6.97 (bs, 2H), 7.04-7.19 (m, 6H), 7.72 (d, 2H), 7.79-7.98 (m, 1H), 8.28-8.35 (m, 1H).

Intermediate F 9H-fluoren-9-yl)methyl (3-(4-formylpiperidin-1-yl)-3-oxopropyl)carbamate

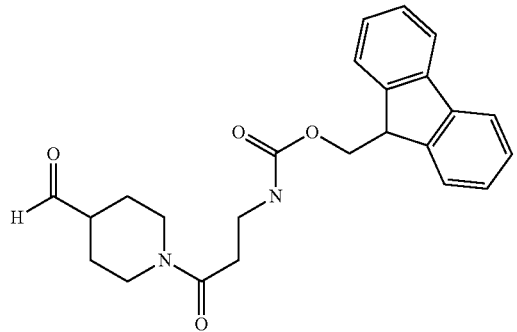 [SMILES: O=CC1CCN(C(=O)CCNC(=O)OCC2c3ccccc3-c3ccccc32)CC1]

Step 1:

(9H-fluoren-9-yl)methyl 3-(4-(hydroxymethyl)piperidin-1-yl)-3-oxopropylcarbamate

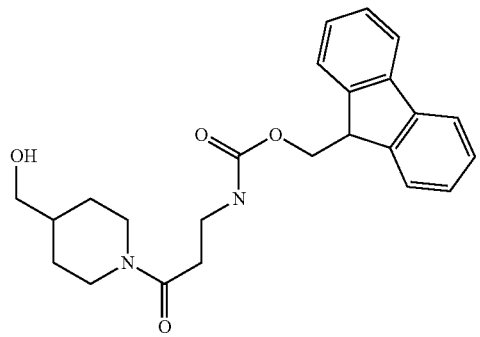 [SMILES: O=C(NCCC(=O)N1CCC(CO)CC1)OCC1c2ccccc2-c2ccccc21]

To a stirred solution of piperidin-4-ylmethanol (200 mg, 1.74 mmol), 3-(((9H-fluoren-9-yl)methoxy)carbonylamino)propanoic acid (541 mg, 1.74 mmol) and HATU (660 mg, 1.74 mmol) in dry DMF (5 mL) was added DIPEA (0.910 mL, 5.21 mmol). The yellow mixture was stirred at ambient temperature over night. The reaction mixture was diluted with EtOAc (50 mL) and washed with 15% aq NaCl solution (50 mL) and 30% aq NaCl solution (50 mL). Solvents were evaporated and the residue was purified by preparative HPLC. After freezedrying the residue was redissolved in DCM and Heptane was added. Evaporation afforded the title compound as a colourless solid (378 mg, 53%).

LC/MS: m/z: 409 [M+H]$^+$

1H NMR (500 MHz, DMSO) d 0.88-1.09 (m, 2H), 1.51-1.73 (m, 3H), 2.44 (t, 2H), 2.47-2.52 (m, 1H+DMSO peak), 2.93 (t, 1H), 3.18 (dd, 2H), 3.23 (d, 2H), 3.80 (d, 1H), 4.20 (t, 1H), 4.29 (d, 2H), 4.37 (d, 1H), 7.21 (t, 1H), 7.33 (dt, 2H), 7.41 (t, 2H), 7.68 (d, 2H), 7.89 (d, 2H).

Step 2

(9H-fluoren-9-yl)methyl (3-(4-formylpiperidin-1-yl)-3-oxopropyl)carbamate

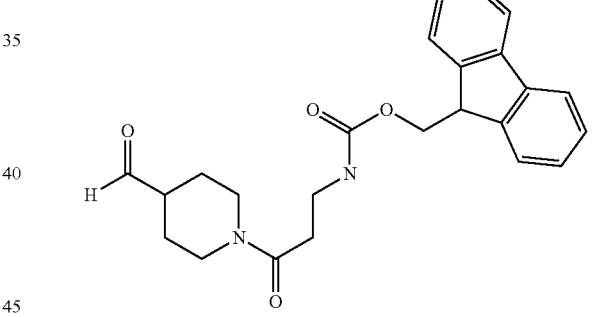

To a solution of (9H-fluoren-9-yl)methyl 3-(4-(hydroxymethyl)piperidin-1-yl)-3-oxopropylcarbamate (362 mg, 0.89 mmol) in DCM (5 mL) was added solid Dess-Martin Periodinane (413 mg, 0.97 mmol). The resulting suspension was stirred at ambient temperature for 2.5 h. To the reaction mixture was added 10% Na$_2$S$_2$O$_3$ (3 mL), 10% NaHCO$_3$ (3 mL) and DCM (2 mL), the mixture was stirred vigorously for 10 min and allowed to settle. The layers were separated and the water phase containing unsoluble salts was extracted repeatedly with DCM. The combined organic phases were dried over MgSO$_4$, filtered and the solvents were evaporated to leave crude product (440 mg) which was used without further purification.

LC/MS: m/z: 407 [M+H]$^+$

Intermediate G (R)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate

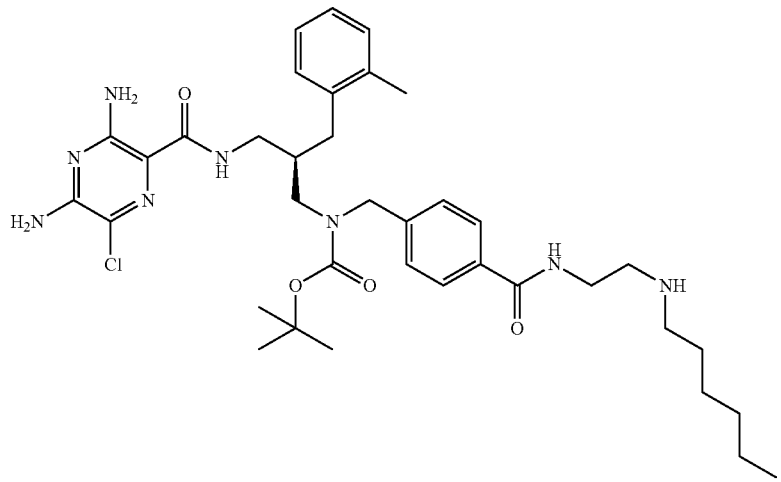 [SMILES: CCCCCCNCCNC(=O)c1ccc(CN(C[C@@H](CNC(=O)c2nc(Cl)c(N)nc2N)Cc2ccccc2C)C(=O)OC(C)(C)C)cc1]

$^1$H NMR (500 MHz, DMSO-$d_6$) δ 1.9-2.02 (m, 1H), 2.23 (s, 3H), 2.41-2.55 (m, 2H), 2.91-3.09 (m, 2H), 3.12-3.23 (m, 2H), 4.48 (d, 2H), 5.17 (d, 1H), 5.24-5.32 (m, 1H), 5.85-5.96 (m, 1H), 6.97 (bs, 2H), 7.04-7.15 (m, 3H), 7.21-7.25 (m, 1H), 7.28 (t, 1H), 8.00 (t, 1H).

LC/MS: m/z 433.3 [M+H]$^+$

Step 1

(R)-allyl (3-(3,5-diamino-6-chloropyrazine-2-carboxamido)-2-(2-methylbenzyl)propyl)carbamate

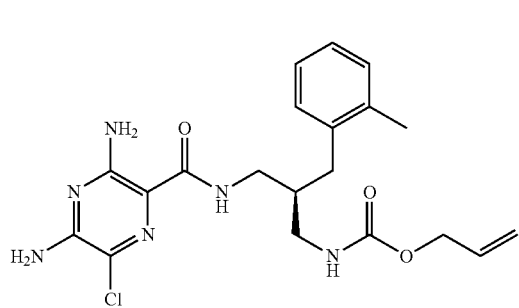 [SMILES: C=CCOC(=O)NC[C@@H](CNC(=O)c1nc(Cl)c(N)nc1N)Cc1ccccc1C]

(3,5-diamino-6-chloropyrazin-2-yl)(1H-imidazol-1-yl)methanone, (858 mg, 3.59 mmol) and (R)-allyl (3-amino-2-(2-methylbenzyl)propyl)carbamate (Intermediate A, Step 5) (990 mg, 3.77 mmol) were suspended in NMP (15 mL) and heated to 100° C. for 4 h. The reaction mixture was allowed to cool to room temperature. EtOAc (50 mL) and water (50 mL) were added, shaken and the phases separated. The aqueous phase was extracted with EtOAc (2×50 mL). The combined organic phases were washed with 0.1 M HCl (aq) (50 mL), water (2×50 mL), brine (50 mL), dried with a phase separator and evaporated in vacuo. The residue was purified by automated flash chromatography on a Biotage® KP-SIL 100 g column. A gradient from 20-80% of EtOAc in heptane over 9 CV was used as mobile phase. The product was collected using the wavelength 270 nm. The collected fractions were pooled and evaporated in vacuo to yield (R)-allyl (3-(3,5-diamino-6-chloropyrazine-2-carboxamido)-2-(2-methylbenzyl)propyl)carbamate (714 mg, 45.9%) as a pale solid.

Step 2

(S)-3,5-diamino-N-(3-amino-2-(2-methylbenzyl)propyl)-6-chloropyrazine-2-carboxamide

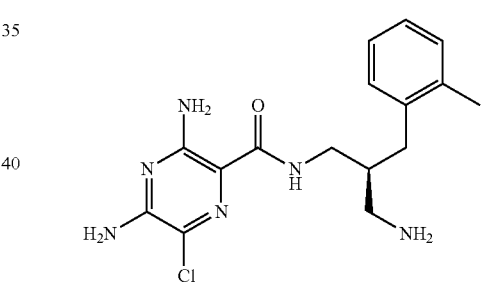

(R)-allyl (3-(3,5-diamino-6-chloropyrazine-2-carboxamido)-2-(2-methylbenzyl)propyl)carbamate (694 mg, 1.60 mmol), 1,3-dimethylpyrimidine-2,4,6(1H,3H,5H)-trione (688 mg, 4.41 mmol), palladium (II) acetate (14.4 mg, 0.06 mmol) and triphenylphosphine (50.5 mg, 0.19 mmol) were dissolved in DCM (7 mL) and heated to 35° C. for 1.5 h. A suspension was formed. DCM (50 mL) and 5% Na$_2$CO$_3$ (aq) (50 ml) were added and the mixture stirred for 15 min. The phases were separated and the aqueous phase extracted with DCM (50 mL). The combined organic phases were dried with a phase separator and evaporated in vacuo. The compound was purified by preparative HPLC on a Kromasil C8 column (10 μm 250×50 ID mm) using a gradient of 5-45% acetonitrile in H$_2$O/MeCN/AcOH 95/5/0.2 buffer over 20 minutes with a flow of 100 mL/min. The compounds were detected by UV at 270 nm. The product fractions were collected and freeze-dried to yield 586 mg of the acetic acid salt. The salt was stirred in EtOAc (50 mL) and 5% Na$_2$CO$_3$ (aq) for 15 min and the phases were then separated. The aqueous phase was extracted with EtOAc (3×50 mL). The combined organic phases were dried with Na$_2$SO$_4$ (s), filtered and evaporated in vacuo to yield (S)-3,5-diamino-N-

(3-amino-2-(2-methylbenzyl)propyl)-6-chloropyrazine-2-carboxamide (411 mg, 73.5%) as a light yellow solid. Chiral purity: 60% ee, determined with chiral SFC column: ChiralPak IC (150×4.6 mm), 3 μm particle size, mobile phase: 20% MeOH/DEA 100:0.5 in $CO_2$, 120 bar, flow rate 4 mL/min.

$^1$H NMR (500 MHz, DMSO-$d_6$) δ 1.73 (bs, 2H), 2.01-2.12 (m, 1H), 2.50 (s, 3H), 2.64-2.73 (m, 2H), 2.76-2.86 (m, 2H), 3.4-3.53 (m, 2H), 7.19 (bs, 2H), 7.28-7.41 (m, 4H), 8.39 (t, 1H).

LC/MS: m/z 349.2 [M+H]$^+$

Step 3

(R)-tert-butyl (3-(3,5-diamino-6-chloropyrazine-2-carboxamido)-2-(2-methylbenzyl)propyl)carbamate

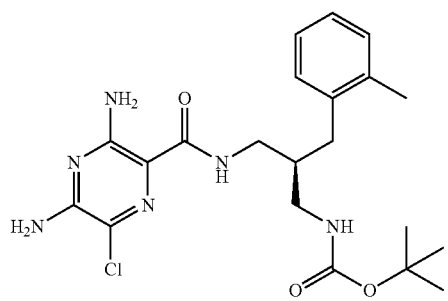 [SMILES: Cc1ccccc1C[C@@H](CNC(=O)OC(C)(C)C)CNC(=O)c1nc(Cl)c(N)nc1N]

(S)-3,5-diamino-N-(3-amino-2-(2-methylbenzyl)propyl)-6-chloropyrazine-2-carboxamide (1.19 g, 3.41 mmol), $BOC_2O$ (0.871 mL, 3.75 mmol) and DIPEA (0.596 mL, 3.41 mmol) were dissolved in DCM (100 mL) and stirred at room temperature for 18 h. The reaction mixture was washed with 0.1 M HCl (aq), dried with a phase separator and evaporated in vacuo. The residue was purified by automated flash chromatography on a Biotage® KP-SIL 100 g column. A gradient from 30-70% of EtOAc in heptane over 9 CV followed by 70% EtOAc in heptane over 3 CV were used as mobile phase. The product was collected using the wavelength 268 nm. The product was evaporated in vacuo to yield (1.150 g, 75%) as a pale solid.

The enantiomer was purified using chiral preparative HPLC (Column: ChiralPak AY (250×20 mm), 20 μm particle size, mobile phase: heptane/EtOH/TEA 20/80:0.1, flow rate 120 m/min). The first eluting compound was collected to yield 866 mg, chiral purity: 98.6% ee. Optical rotation $[\alpha]_D^{20}$=−6 (acetonitrile, c=1).

$^1$H NMR (500 MHz, DMSO-$d_6$) δ 1.38 (d, 9H), 1.88-2 (m, 1H), 2.23 (s, 3H), 2.39-2.49 (m, 2H), 2.83-2.93 (m, 1H), 2.93-3.03 (m, 1H), 3.09-3.23 (m, 2H), 6.89 (t, 1H), 6.97 (bs, 2H), 7.04-7.15 (m, 3H), 7.22 (d, 1H), 8.01 (t, 1H).

LC/MS: m/z 449.2 [M+H]$^+$

Step 4

(S)-3,5-diamino-N-(3-amino-2-(2-methylbenzyl)propyl)-6-chloropyrazine-2-carboxamide

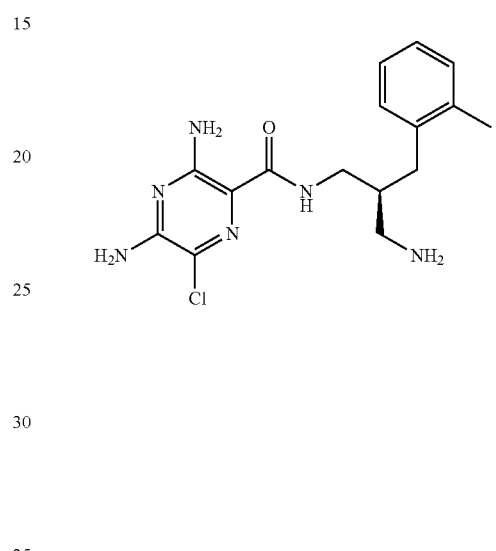

Acetyl chloride (1.422 mL, 20 mmol) was added dropwise to an icebath cooled flask of MeOH (5 mL, 123.59 mmol). The mixture was stirred for 5 min and was then added to a flask of (R)-tert-butyl (3-(3,5-diamino-6-chloropyrazine-2-carboxamido)-2-(2-methylbenzyl)propyl)carbamate (866 mg, 1.93 mmol). The reaction was stirred at room temperature for 45 min and was then evaporated in vacuo. The residue was stirred in EtOAc (125 mL) and 8% $NaHCO_3$ (aq) (125 mL) for 15 min. The phases were separated and the aqueous phase extracted with EtOAc (3×125 mL). The combined organic phases were dried with $Na_2SO_4$ (s), filtered and evaporated in vacuo to yield (S)-3,5-diamino-N-(3-amino-2-(2-methylbenzyl)propyl)-6-chloropyrazine-2-carboxamide (459 mg, 68.2%) as a pale solid. Chiral purity: 99% ee, determined with chiral SFC column: Lux C4 (150×4.6 mm), 3 μm particle size, mobile phase: 35% EtOH/$NH_3$ 100:0.5 in $CO_2$, 120 bar, flow rate 4 mL/min. Optical rotation $[\alpha]_D^{20}$=−45.9 ($CHCl_3$, c=1).

$^1$H NMR (500 MHz, DMSO-$d_6$) δ 1.57 (bs, 2H), 1.78-1.88 (m, 1H), 2.26 (s, 3H), 2.39-2.48 (m, 2H), 2.52-2.62 (m, 2H), 3.18-3.28 (m, 2H), 6.95 (bs, 2H), 7.04-7.17 (m, 4H), 8.14 (t, 1H).

LC/MS: m/z 349.2 [M+H]$^+$

Step 5

(R)-(9H-fluoren-9-yl)methyl (2-(4-(((tert-butoxycarbonyl)(3-(3,5-diamino-6-chloropyrazine-2-carboxamido)-2-(2-methylbenzyl)propyl)amino)methyl)benzamido)ethyl)(hexyl)carbamate

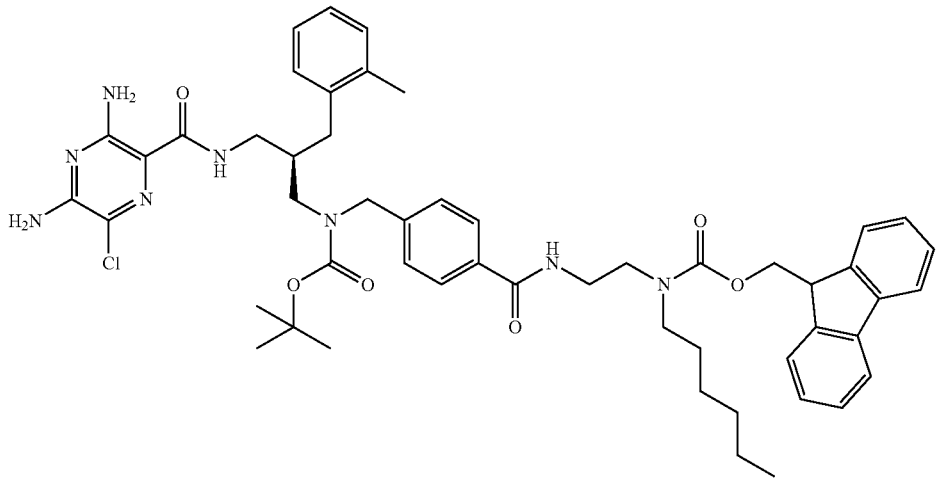 [SMILES: CCCCCCN(CCNC(=O)c1ccc(CN(C[C@@H](CNC(=O)c2nc(Cl)c(N)nc2N)Cc2ccccc2C)C(=O)OC(C)(C)C)cc1)C(=O)OCC1c2ccccc2-c2ccccc21]

(S)-3,5-diamino-N-(3-amino-2-(2-methylbenzyl)propyl)-6-chloropyrazine-2-carboxamide (215 mg, 0.62 mmol), (9H-fluoren-9-yl)methyl (2-(4-formylbenzamido)ethyl)(hexyl)carbamate (Intermediate H) (293 mg, 0.59 mmol) and DIPEA (0.103 mL, 0.59 mmol) were dissolved in MeOH (5 mL) and stirred at room temperature for 1.5 h. Sodium cyanoborohydride (38.8 mg, 0.62 mmol) and acetic acid (0.101 mL, 1.76 mmol) were then added and stirring continued for 3 h. The reaction was quenched by addition of 8% NaHCO₃ (aq). DCM (25 mL) and 8% NaHCO₃ (aq) (25 mL) were added, shaken and the phases separated. The aqueous phase was extracted with DCM (25 mL). The combined organic phases were dried with a phase separator and evaporated in vacuo.

The residue and BOC₂O (0.150 mL, 0.65 mmol) were dissolved in DCM (5 mL) and stirred at room temperature for 18 h. The reaction mixture was concentrated in vacuo. The product was purified by automated flash chromatography on a Biotage® KP-SIL 50 g column. A gradient from 50-100% of EtOAc in heptane over 9 CV was used as mobile phase. The product was collected using the wavelength 265 nm. The product fractions were evaporated in vacuo to yield (R)-(9H-fluoren-9-yl)methyl (2-(4-(((tert-butoxycarbonyl)(3-(3,5-diamino-6-chloropyrazine-2-carboxamido)-2-(2-methylbenzyl)propyl)amino)methyl)benzamido)ethyl)(hexyl)carbamate (511 mg, 93%) as a colorless film.

¹H NMR (500 MHz, DMSO-d₆) δ 0.82 (t, 3H), 0.87-0.96 (m, 1H), 0.99-1.26 (m, 6H), 1.27-1.5 (m, 10H), 2.19 (s, 3H), 2.23-2.35 (m, 1H), 2.8-2.9 (m, 1H), 2.9-3.04 (m, 1H), 3.05-3.39 (m, 10H), 4.16-4.32 (m, 3H), 4.39-4.57 (m, 2H), 6.88-7.18 (m, 8H), 7.30 (t, 2H), 7.39 (t, 2H), 7.55-7.76 (m, 4H), 7.77-7.99 (m, 3H), 8.37-8.52 (m, 1H).

LC/MS: m/z 931.4 [M+H]⁺

Step 6

(R)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate

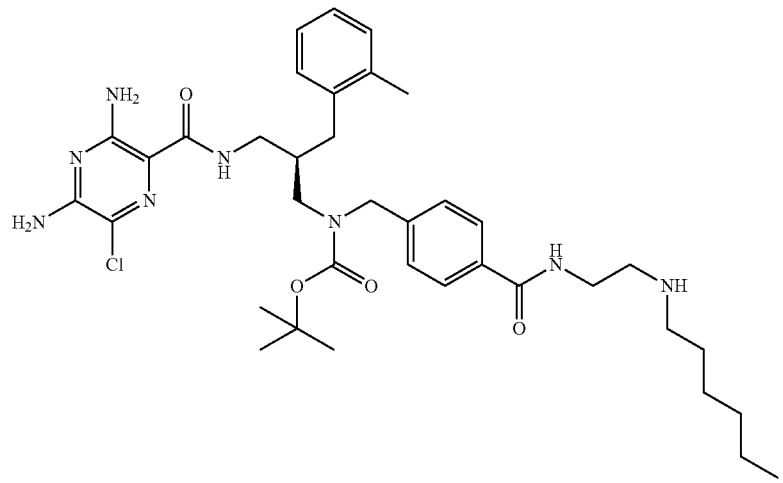 [SMILES: CCCCCCNCCNC(=O)c1ccc(CN(C[C@@H](CNC(=O)c2nc(Cl)c(N)nc2N)Cc2ccccc2C)C(=O)OC(C)(C)C)cc1]

(R)-(9H-fluoren-9-yl)methyl (2-(4-(((tert-butoxycarbonyl)(3-(3,5-diamino-6-chloropyrazine-2-carboxamido)-2-(2-methylbenzyl)propyl)amino)methyl)benzamido)ethyl)(hexyl)carbamate (511 mg, 0.55 mmol) was dissolved in THF (5 mL) and piperidine (0.543 mL, 5.49 mmol) added. The reaction was stirred at room temperature for 18 h. The solvent was evaporated in vacuo. The residue was purified by automated flash chromatography on a Biotage® KP-SIL 50 g column. A gradient from 2.5-8% of (2 M ammonia in MeOH) in DCM over 9 CV followed by 8% of (2 M ammonia in MeOH) in DCM over 3 CV were used as mobile phase. The product was collected and evaporated in vacuo to yield (R)-tert-butyl (3-(3,5-diamino-6-chloropyrazine-2-carboxamido)-2-(2-methylbenzyl)propyl)(4-((2-(hexylamino)ethyl)carbamoyl)benzyl)carbamate (326 mg, 84%) as a pale solid.

$^1$H NMR (500 MHz, DMSO-d$_6$) δ 0.84 (t, 3H), 1.12-1.45 (m, 17H), 2.20 (s, 3H), 2.24-2.36 (m, 1H), 2.51-2.58 (m, 2H), 2.69 (t, 2H), 2.92-3.05 (m, 1H), 3.05-3.4 (m, 7H), 4.22-4.37 (m, 1H), 4.38-4.54 (m, 1H), 6.97 (bs, 2H), 7.03-7.18 (m, 6H), 7.72 (d, 2H), 7.79-7.98 (m, 1H), 8.28-8.35 (m, 1H).

LC/MS: m/z 709.4 [M+H]$^+$

Intermediate H (9H-fluoren-9-yl)methyl (2-(4-formylbenzamido)ethyl)(hexyl)carbamate

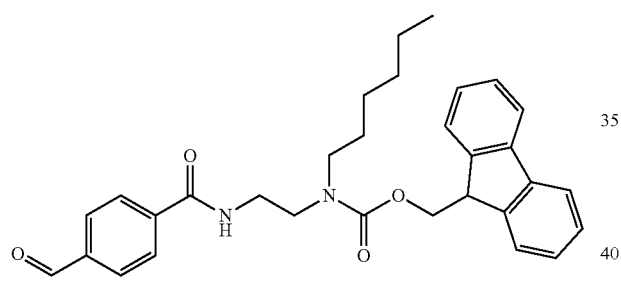

4-formylbenzoic acid (0.81 g, 5.40 mmol) and 4-methylmorpholine (1.424 mL, 12.95 mmol) were dissolved in THF (10 mL) and cooled with an icebath. Isobutyl carbonochloridate (0.700 mL, 5.40 mmol) was added dropwise, the mixture stirred for 30 min and (9H-fluoren-9-yl)methyl (2-aminoethyl)(hexyl)carbamate hydrochloride (Intermediate C) (1.739 g, 4.32 mmol) added. The reaction was stirred at room temperature for 2.5 h. The resulting suspension was extracted between EtOAc (50 mL) and water (50 mL). The organic phase was washed with 5% citric acid (2×50 mL), 10% Na$_2$CO$_3$ (aq) (50 mL), brine (50 mL), dried with Na$_2$SO$_4$ (s), filtered and evaporated in vacuo. The residue was purified by automated flash chromatography on a Biotage® KP-SIL 100 g column. A gradient from 20-80% of EtOAc in heptane over 9 CV followed by 80% EtOAc in heptane over 3 CV were used as mobile phase. The product was collected using the wavelength 260 nm. The product peaks were evaporated in vacuo to yield (9H-fluoren-9-yl)methyl (2-(4-formylbenzamido)ethyl)(hexyl)carbamate (1.690 g, 79%) as a white solid.

$^1$H NMR (500 MHz, CDCl$_3$) δ 0.82-0.95 (m, 3H), 1.08-1.46 (m, 8H), 3.02-3.21 (m, 3H), 3.48-3.64 (m, 3H), 4.16-4.25 (m, 1H), 4.51-4.74 (m, 2H), 7.2-7.42 (m, 5H), 7.5-7.67 (m, 3H), 7.75 (d, 2H), 7.93 (q, 3H), 10.06 (s, 1H).

LC/MS: m/z 499.5 [M+H]$^+$

Intermediate I 4-formyl-N-(2-(hexyl((2S,3R,4R)-2,3,4,5-tetrahydroxypentyl)amino)ethyl)benzamide

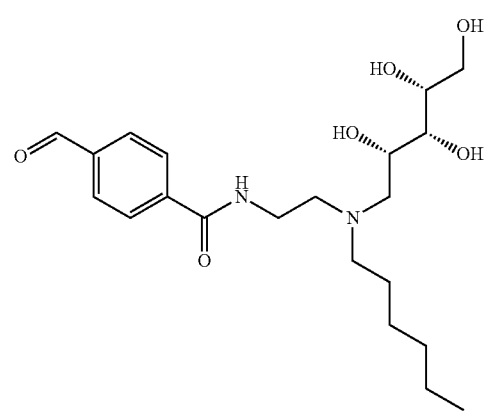 [SMILES: CCCCCCN(CCNC(=O)c1ccc(C=O)cc1)C[C@H](O)[C@@H](O)[C@H](O)CO]

Step 1 tert-butyl 2-(hexylamino)ethylcarbamate

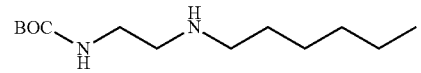 [SMILES: CCCCCCNCCNC(=O)OC(C)(C)C]

To a 10 L flange flask was charged hexylamine (1020 mL, 7.76 mol), Na$_2$CO$_3$ (206 g, 1.94 mol) and MeCN (2560 mL). The mixture was heated to 70° C. over 1 h. To the mixture was charged a solution of tert-butyl 2-bromoethylcarbamate (371.3 g, 289.6 g active, 1.29 mol) in MeCN (740 ml) slowly, over 1½ h. The reaction was stirred at 70° C. overnight. The reaction was cooled to 50° C. and concentrated in vacuo. To the stirred residue was charged water (2100 mL) and EtOAc (4200 ml). The layers were separated and the organic phases were washed with water (3×2100 ml). The organic phases were concentrated in vacuo and azeotroped sequentially with water (3×870 ml) and EtOH (3×870 ml) to provide 368.6 g (315.8 g active, quantitative yield) of stage 1 as a clear oil.

1H-NMR (270 MHz, CDCl$_3$) δ 4.95 (1H, br s), 3.29-3.19 (m, 2H), 2.71 (t, 2H), 2.58 (t, 2H), 1.50-1.40 (br. m, 11H), 1.35-1.23 (m, 6H), 0.89 (t, 3H).

LC/MS: m/z 245 [M+H]$^+$

Step 2 tert-butyl 2-(hexyl((2S,3R,4R)-2,3,4,5-tetrahydroxypentyl)amino)ethylcarbamate

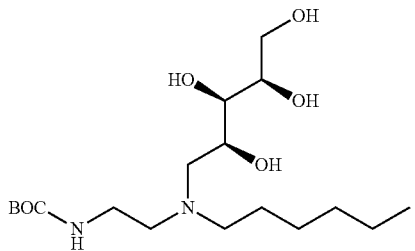 [SMILES: CCCCCCN(CCNC(=O)OC(C)(C)C)C[C@H](O)[C@@H](O)[C@H](O)CO]

To a 10 L flange flask was charged D-xylose (124.3 g, 0.83 mol), tert-butyl 2-(hexylamino)ethylcarbamate (step 1, 181.8 g, 155.8 g active, 0.49 mol), EtOH (5000 ml) and DIPEA (110.8 ml, 0.64 mol). The mixture was heated to 35° C. for 1 h, until dissolved. To the solution was charged AcOH (36.5 mL, 0.64 mol) and the resulting mixture stirred at 35° C. for 15 min. To this was charged NaCNBH$_3$ (56.1 g, 0.89 mol), portionwise over 5 min at 35° C. No exotherm or gas evolution noted. The reaction was stirred at 35° C. overnight. To this was charged NaCNBH$_3$ (8.0 g, 0.13 mol) and stirred at 35° C. for 3 h. The reaction was allowed to cool to room temperature overnight. To the mixture was charged sat. aq. NaHCO$_3$ (1600 mL) over 10 min, a slightly exothermic reaction was observed. The mixture was stirred at room temperature over the weekend. The EtOH was removed in vacuo and combined with a second batch of the same scale (181.8 g stage 1) for work-up. To the mixture was charged NaCl (311 g). The organic phases were extracted with 10% MeOH/DCM (3×3000 ml) and the combined organic phases were concentrated in vacuo. The resulting residue was purified via chromatography (SiO$_2$, 7 kg), packed, loaded and eluted with 5% MeOH/DCM+0.2% 7 N NH$_3$ in MeOH (35 L), 50% MeOH/DCM+0.2% 7 N NH$_3$ in MeOH (75 L), then flushing with 65% MeOH/DCM+0.2% 7 N NH$_3$ in MeOH (20 L). Product containing fractions were combined, evaporated in vacuo and azeotroped with MeOH (2×500 mL) to provide 387 g (366 g active, 76%) of the subtitle compound as a yellow gum.

1H-NMR (270 MHz, DMSO-d6) δ 6.80 (br.s, 1H), 4.80-4.30 (br. m, 3H), 4.22-4.05 (br. m, 1H), 3.74-3.60 (br. m, 1H), 3.59-3.48 (m, 1H), 3.47-3.20 (m, 6H), 3.08-2.87 (br. m, 2H), 2.70-2.45 (br. m, 3H), 1.51-1.35 (m, 10H), 1.32-1.16 (m, 7H), 0.85 (t, 3H).

LC/MS: m/z 401 [M+H]$^+$

Step 3

(2R,3R,4S)-5-((2-aminoethyl)(hexyl)amino)pentane-1,2,3,4-tetraol

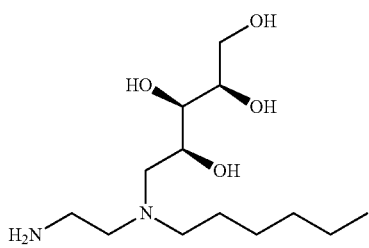

To a solution of tert-butyl 2-(hexyl((2S,3R,4R)-2,3,4,5-tetrahydroxypentyl)amino)ethylcarbamate (step 2, 365 g, 345 g active, 0.91 mol) in MeOH (520 ml) at room temperature was charged 4 M HCl in dioxane (1710 ml, 6.84 mol) over 30 min, maintaining a temperature <31° C. The reaction was stirred at room temperature for 1.5 h. The reaction mixture was concentrated in vacuo to provide 485.1 g (306 g active, 95%) of the subtitle compound as a purple black tar.

1H-NMR (270 MHz, DMSO-d6) δ 8.41 (br. s, 3H), 4.20-3.00 (br. m, 16H), 1.77-1.62 (br. m, 2H), 1.37-1.17 (br. m, 6H), 0.87 (br. t, 3H).

MS ES: m/z 279 [M+H]$^+$

Step 4

4-formyl-N-(2-(hexyl((2S,3R,4R)-2,3,4,5-tetrahydroxypentyl)amino)ethyl)benzamide

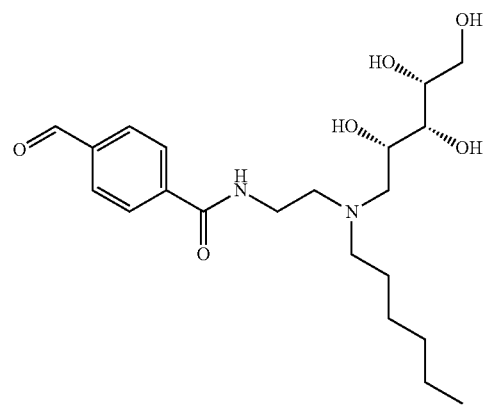 [SMILES: CCCCCCN(CCNC(=O)c1ccc(C=O)cc1)C[C@H](O)[C@@H](O)[C@H](O)CO]

To a 5 L flange flask was charged 4-formylbenzoic acid (107.6 g, 0.72 mol) and DMF (1400 ml) at room temperature. To this was charged 4-methylmorpholine (255.5 ml, 2.3 mol). The mixture was cooled to −15° C. over 5 min. To this was charged isobutyl chloroformate (93.4 ml, 0.71 mol) over 15 min, maintaining a reaction temperature <−10° C. The reaction was stirred at −10° C. to −15° C. for 1 h. In a separate flask, (2R,3R,4S)-5-((2-aminoethyl)(hexyl)amino)pentane-1,2,3,4-tetraol (step 3, 383.9 g, 245.7 g active, 0.71 mol) was dissolved in DMF (1400 ml) and 4-methylmorpholine (123 ml, 1.1 mol) at 45° C. over 1 h. To the mixed anhydride mixture was charged the step 3 containing mixture over 15 min, maintaining a reaction temperature <−5° C. The resulting mixture was allowed to warm to room temperature overnight. To the reaction mixture was charged sat. aq. NaHCO$_3$ (2500 ml) slowly, over 30 min. The resulting mixture was concentrated in vacuo. To the residue was charged sat. aq. NaHCO$_3$ (1200 ml) and stirred with DCM (4900 ml) for 10 min at RT. The layer were separated and the aqueous was extracted with 13% MeOH/DCM (2870 ml). The combined organic phases were washed with sat. aq. NaHCO$_3$ (1200 ml) and concentrated in vacuo to provide 395.3 g. The residue was combined with 10 g crude material recovered from an intermediate scale reaction and purified via chromatography [SiO$_2$, 3 kg; loaded and packed with 5% MeOH/DCM; eluted with 5% MeOH/DCM (30 L), 10% MeOH/DCM (20 L), 20% MeOH/DCM (10 L), 30% MeOH/DCM (30 L), 40% MeOH/DCM (20 L) and 100% MeOH (80 L)]. Product fractions were combined (100 L) and concentrated in vacuo to provide 138.4 g (112 g active, 39% yield) of the subtitle compound. $^1$H NMR indicated 81.4 w/w % activity with ca. 5.5% remaining formylbenzamide impurity. HPLC-MS analysis indicated 97.4% purity. Mixed fractions (20 L) were combined and concentrated in vacuo to provide 46 g of material with a purity of 74.5% by HPLC. This was re-purified via chromatography (SiO$_2$, 600 g), eluting with 10%-30% MeOH/DCM (18 L). Product fractions were combined and concentrated in vacuo to provide additional 21.0 g (20.3 g active, 44%) of the subtitle compound.

1H-NMR (270 MHz, DMSO-d6): δ 10.08 (s, 1H), 8.60 (t, 1H), 8.02 (d, 2H), 7.97 (d, 2H), 4.70-4.20 (br. m, 4H), 3.66-3.52 (m, 2H), 3.46-3.34 (m, 8H), 2.65-2.58 (m, 2H), 2.51-2.44 (m, 2H), 1.40-1.28 (br. m, 2H), 1.19-1.08 (m, 6H), 0.79 (t, 3H).

LC/MS: m/z 411 [M+H]$^+$

Enzymatic Desymmetrisation of 2-(2-methylbenzyl)propane-1,3-diamine

The enzymatic desymmetrisation of 2-(2-methylbenzyl)propane-1,3-diamine was investigated using diallylcarbonate and a range of immobilized lipases.

Immobilised Lipase Screen:

To a solution of 2-(2-methylbenzyl)propane-1,3-diamine (0.60 g, 3.37 mmol) in 1,4-dioxan (30 mL) was added diallylcarbonate (0.507 mL, 3.53 mmol). 1.0 mL aliquots of this solution were added to 10 mL screw cap test tubes containing the enzymes (0.02 g) described in Table 1. The tubes were shaken at 500 rpm/30° C. for 3 days. Each tube was sampled and analysed by Reverse Phase HPLC (4.6×50 mm Thermoquest Hypercarb, UV detection at 260 nm) and Chiral HPLC (4.6×250 mm Chiralpak IC3, UV detection at 260 nm).

Six of the screened lipases showed more than 20% conversion after 3 days (Table 1).

Solvent Screen with Amano Lipase PS-IM:

A solvent screen with Amano Lipase PS-IM was carried out in 20 relative volumes of the solvents with 1.1 equivalents diallylcarbonate, 1 mass equivalent Amano PS-IM and 0.1 g of 2-(2-methylbenzyl)propane-1,3-diamine. After 6 days at 30° C. the experiments were sampled using the same methods as described for the lipase screen (Table 2). 2-(2-Methylbenzyl)propane-1,3-diamine was not very soluble in non-polar solvents, such as methyl t-butyl ether, heptanes and cyclohexane. Addition of THF to each of the solvents did, however, allow the diamine to dissolve and the above 1:1 solvent mixtures were tested. The results suggested that 2-MeTHF gave the best enantioselectivity, despite some background reaction. In order to minimize the background carboxylation in 2-MeTHF, a gram scale experiment was carried out at 30° C. with excess of Amano lipase PS-IM (3 mass equivalents immobilized lipase, 1.2 equivalents diallylcarbonate, 20 vol 2-MeTHF). The reaction proceeded to completion within 3 days and after workup, crude (R)-monoallylcarbamate 1-(R) was isolated with 85% ee. Converting the crude product into the corresponding D-tartarate salt in ethanol increased the enantiomeric excess to 91.0% (58% overall yield from the diamine).

TABLE 2

| Solvent | Conversion[1] | R/S ratio[2] |
|---|---|---|
| TBME:THF (1:1) | 72.8 | 6.25 |
| Heptane:THF (1:1) | 88.4 | 5.45 |
| Cyclohexane:THF (1:1) | 89.8 | 6.81 |
| Toluene | 52.5 | 6.63 |
| THF | 36.8 | 4.91 |
| MeTHF | 86.2 | 7.06 |
| MeTHF (No enzyme) | 24.8 | — |

[1]Conversion to mono-allyl carbamate are indicated in % area from HPLC.
[2]R/S ratios are indicated in % area R enantiomer divided with % area S enantiomer from chiral HPLC.

Sodium Channel ENaC Ussing Chamber Test

Human primary bronchial epithelial cells differentiated at air-liquid interface (ALI) on snapwell permeable supports (MatTek Corporation, MA, USA, cat no AIR-100-SNP) were maintained at ALI culture in a humidified incubator at 37° C. and 5% CO$_2$. Basolateral medium (MatTek Corporation, MA, USA cat no AIR-100-MM-ASY) was changed every second day. Mucus or liquid formed on the apical side was gently aspirated every second day to maintain viability and performance of the cells.

The transepithelial voltage between the luminal/apical and basolateral membrane were measured in the ussing chamber consisted of vertical, in-house manufactured ussing chambers, DVC-1000 V/C clamps with preamplifiers (World Precision Instruments), electrode kits (EK1, World Precision Instruments), Power Lab with Chart5 software, water bath with external circulation and carbogen gas distribution and regulation system. Electrodes used in the set up were casted manually using 4% agarose in 0.9% sterile NaCl according to the manufacturer's recommendation.

The ussing chambers were assembled with an empty snapwell membrane (Costar 3407) and electrodes contained in Kreb's buffer (SIGMA-ALDRICH cat no K3753) for one hour at 37° C. in presence of 95% oxygen and 5% carbon

TABLE 1

| Enzyme | Conversion[1] | R/S ratio[2] |
|---|---|---|
| IMM CALB (*Candida Antartica Lipase B*) | 33.2 | 0.87 |
| IMM CALBY (*Candida Antartica Lipase B*) | 52.8 | 0.81 |
| Novozym 435 (*Candida Antarctica Lipase B*) | 75.8 | 1.76 |
| Amano Lipase PS-C1 (*Pseudomonas Cepacia Lipase*) | 31.4 | 9.8 |
| Amano Lipase PS-IM (*Pseudomonas Cepacia Lipase*) | 21.2 | 5.0 |
| Amano Lipase PS-D (*Pseudomonas Cepacia Lipase*) | 33.4 | 12.3 |
| No enzyme (Control) | — | — |

[1]Conversion to mono-allyl carbamate are indicated in % area from HPLC.
[2]R/S ratios are indicated in % area R enantiomer divided with % area S enantiomer from chiral HPLC.

dioxide. After this equilibration step the system was compensated for fluid resistance and input offset.

Prior to experiment the ALI cultures were assessed for Trans Epithelial Electric Resistance (TEER) with the EndOhm device (World Precision Instruments), cells exhibiting a resistance between 400-600 Ohms were used.

The equilibrated chambers were reassembled with a snapwell containing ALI cells and after 20 minutes stabilisation cumulative doses of the compounds were added to the apical side of the membrane. After the final dose 10 µM Benzamil was added to reach maximum.

All test compounds, including the reference compound, were diluted from 10 mM stocks in 100% DMSO and added to opaque 96-well plates (Greiner, Cat No. 651201). Dilution series of 12 doses were prepared in DMSO, starting with 3 µM followed by 10 times dilution steps.

Chart5 for Windows software was used to measure the value of the short circuit current after each compound addition. The data was transferred into Excel and analysed using IDBS XLfit® 5.2 (ID Business Solutions Ltd). The molar concentration of test or reference compound producing 50% inhibition (curve IC50) was derived by fitting data to a 4-parameter logistic function of the form:

$$y=(A+((B-A)/(1+(((10^C)/x)^D))))$$

A The bottom plateau of the curve, i.e. the final minimum y value
B The top of the plateau of the curve i.e. the final maximum y value
C The $\log_{10}$ x value at a y value of 50%.
D The Hill slope factor.
x The known x values.
Table 1 shows the $pIC_{50}$ values for Examples 1 to 14.

TABLE 1

| Example No. | pIC$_{50}$ |
|---|---|
| 1 | 9.5 |
| 2 | 8.6 |
| 3 | 10.1 |
| 4 | 9.2 |
| 5 | 9.0 |
| 6 | 9.5 |
| 7 | 8.9 |
| 8 | 9.5 |
| 9 | 8.6 |
| 10 | 8.6 |
| 11 | 8.8 |
| 12 | 9.6 |
| 13 | 10.1 |
| 14 | 7.5 |

Estimated Intestinal Mucosal Permeation Using Caco-2 Cell Monolayer

Caco-2 cells are grown in Dulbecco's Modified Eagle's medium (DMEM) on 96-well transwell polycarbonate membrane inserts for 15 days until confluence and differentiation is reached. After integrity assessment by measurement of electrical resistance across the monolayer cells are washed two times with HBSS (25 mM HEPES, pH 7.4) and incubated at 37° C. for 30 min.

Stock solutions of test compounds in DMSO are diluted with HBSS (containing 100 µM Lucifer Yellow) to reach the final concentration of 10 µM; all incubations are performed in duplicate. To determine the rate of drug transport in apical to basolateral direction (A to B) 100 µL of test compound solutions are added to the apical compartment of the Transwell insert. The basolateral compartment is filled with 300 µL of HBSS.

For determination of basolateral to apical transport (B to A) the basolateral compartment is filled with 300 µL of test compound solution and 100 µL of HBSS are added to the apical compartment.

After incubation of the plate at 37° C. for 2 h 50 µL from each compartment are removed and transferred to 96 well plates for measurement of fluorescence in a suitable plate reader at 485 nm excitation and 530 nm emission to monitor monolayer integrity. For the test compound permeability analysis 3 volumes of cold methanol are added to each buffer sample and the samples are centrifuged at 4 C for 15 minutes. An aliquot of 5 µL of the supernatant is used for LC/MS/MS analysis.

The apparent permeability (Papp, in units of cm/s) can be calculated using the following equation $$P_{app} = \frac{V_A}{Area \times time} \times \frac{[drug]_{acceptor}}{[drug]_{initial, donor}}$$

where $V_A$ is the volume (in mL) in the acceptor well (0.3 mL for apial to basolateral), Area is the surface area of the membrane (0.143 cm2 for HTS Transwell-96 Well Permeable Supports) and time is total transport time in s.

The apparent permeability in the apical to basolateral direction (Median A to B Papp, 1E-6.cm/s) was measured for each of Examples 1 to 16. No apparent permeability could be detected for any of the Examples in the apical to basolateral direction. Compounds which exhibit low permeability may be more desirable for delivery of ENaC inhibitors via inhaled administration.

The above description of illustrative embodiments is intended only to acquaint others skilled in the art with Applicant's invention, its principles, and its practical application so that others skilled in the art may readily adapt and apply the invention in its numerous forms, as they may be best suited to the requirements of a particular use. This description and its specific examples, while indicating embodiments of this invention, are intended for purposes of illustration only. This invention, therefore, is not limited to the illustrative embodiments described in this specification, and may be variously modified. In addition, it is to be appreciated that various features of the invention that are, for clarity reasons, described in the context of separate embodiments, also may be combined to form a single embodiment. Conversely, various features of the invention that are, for brevity reasons, described in the context of a single embodiment, also may be combined to form sub-combinations thereof.

The invention claimed is:

1. A method of treating an epithelial sodium channel (ENaC) mediated disease state in a mammal suffering from, or at risk of, said disease, which comprises administering to the mammal in need of such treatment a therapeutically effective amount of a compound which is 3,5-diamino-6-chloro-N—((R)-3-((4-((2-(hexyl((2S,3R,4R)-2,3,4,5-tetra-hydroxypentyl)amino)ethyl) carbamoyl)benzyl)amino)-2-(2-methylbenzyl)propyl)pyrazine-2-carboxamide having the below formula:

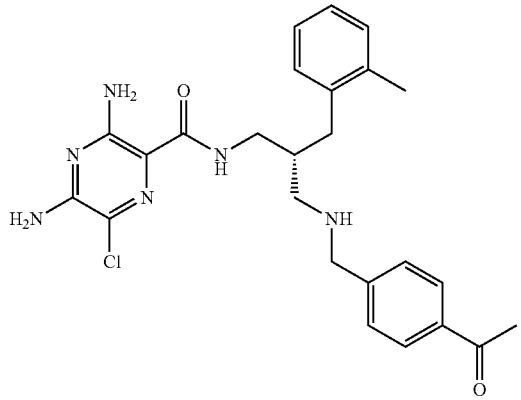

-continued

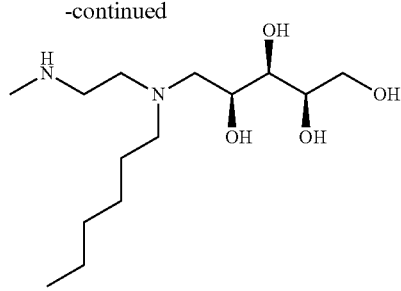

or a pharmaceutically acceptable salt thereof.

2. The method according to claim 1, wherein the ENaC mediated disease state is selected from chronic obstructive pulmonary disease (COPD), cystic fibrosis, asthma, chronic bronchitis and bronchiectasis.

3. The method according to claim 1, wherein the ENaC mediated disease state is chronic obstructive pulmonary disease (COPD) or cystic fibrosis.

* * * * *

SEQUENCE LISTING

<160> NUMBER OF SEQ ID NOS: 1

<210> SEQ ID NO 1
<211> LENGTH: 22

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgaacgttc gaagatgatg at                                              22
```